United States Patent
Yoo et al.

(10) Patent No.: US 11,641,776 B2
(45) Date of Patent: May 2, 2023

(54) ORGANIC COMPOUND, ORGANIC LIGHT EMITTING DIODE AND ORGANIC LIGHT EMITTING DEVICE HAVING THE COMPOUND

(71) Applicant: LG Display Co., Ltd., Seoul (KR)

(72) Inventors: Mi-Sang Yoo, Paju-si (KR); Hyo-Jin Noh, Paju-si (KR); Jeong-Eun Baek, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 549 days.

(21) Appl. No.: 16/702,204

(22) Filed: Dec. 3, 2019

(65) Prior Publication Data

US 2020/0185621 A1 Jun. 11, 2020

(30) Foreign Application Priority Data

Dec. 5, 2018 (KR) ........................ 10-2018-0155232

(51) Int. Cl.
*H01L 51/00* (2006.01)
*C07D 209/94* (2006.01)
*C07D 401/10* (2006.01)
*C09K 11/06* (2006.01)

(52) U.S. Cl.
CPC ....... *H10K 85/6572* (2023.02); *C07D 209/94* (2013.01); *C07D 401/10* (2013.01); *C09K 11/06* (2013.01); *H10K 85/654* (2023.02); *C09K 2211/1018* (2013.01); *H10K 50/11* (2023.02); *H10K 50/13* (2023.02); *H10K 2101/10* (2023.02)

(58) Field of Classification Search
CPC ............. H01L 51/0072; H01L 51/0067; H01L 51/5016; H01L 51/504; H01L 51/5012; H01L 51/5028; H01L 51/0052; H01L 51/5024; C07D 209/94; C07D 401/10; C07D 401/04; C07D 209/82; C09K 11/06; C09K 2211/1018; C09K 2211/1007; C09K 2211/1011; C09K 2211/1029; C07B 2200/05
USPC ........................................................ 428/690
See application file for complete search history.

(56) References Cited

U.S. PATENT DOCUMENTS

| 2014/0160398 A1* | 6/2014 | Yoon ................... H01L 51/0058 585/27 |
| 2016/0111650 A1* | 4/2016 | Noh ...................... C07D 403/10 546/276.7 |
| 2016/0111659 A1* | 4/2016 | Yang ....................... C09K 11/06 546/276.7 |
| 2016/0133856 A1* | 5/2016 | Yang ................... H01L 51/0074 546/102 |

FOREIGN PATENT DOCUMENTS

| CN | 104829521 A | * | 8/2015 | ........... C07D 209/94 |
| CN | 108701771 A | | 10/2018 | |
| KR | 10-2008-0047209 A | | 5/2008 | |
| KR | 10-2012-0061539 A | | 7/2012 | |
| KR | 10-2012-0095765 A | | 8/2012 | |
| KR | 10-2016-0038310 A | | 4/2016 | |
| KR | 10-1661592 B1 | | 10/2016 | |
| WO | WO 2017/146192 A1 | | 8/2017 | |
| WO | WO 2018/066536 A1 | | 4/2018 | |

OTHER PUBLICATIONS

CAS reg. No. 2432929-20-7, Jun. 23, 2020. (Year: 2020).*
Yu, J., et al, "OLED display foundation and industrialization". University of Electronics Science and Technology of China Press, Feb. 2015, p. 23.

* cited by examiner

*Primary Examiner* — Douglas J Mc Ginty
(74) *Attorney, Agent, or Firm* — Birch, Stewart, Kolasch & Birch, LLP

(57) ABSTRACT

Discussed is an organic compound having a benzofluorenocarbazole core and an aromatic or hetero aromatic groups bonded to a specific positions of the benzofluorenocarbazole core, and an organic light emitting diode and an organic light emitting device including the compound. The organic compound has a narrow Stokes Shift between an absorption spectrum peak and an emission spectrum peak, it has a broad spectral overlapping area between its absorption wavelength range and an emission wavelength range of another luminous material. Therefore, it can emit light having high color purity and exhibit excellent luminous efficiency.

22 Claims, 13 Drawing Sheets

ORGANIC COMPOUND, ORGANIC LIGHT EMITTING DIODE AND ORGANIC LIGHT EMITTING DEVICE HAVING THE COMPOUND

CROSS-REFERENCE TO RELATED APPLICATIONS

This application claims the benefit under 35 U.S.C. § 119(a) of Korean Patent Application No. 10-2018-0155232, filed in the Republic of Korea on Dec. 5, 2018, which is incorporated herein by reference in its entirety.

BACKGROUND

Technical Field

The present disclosure relates to an organic compound, and more specifically, to an organic compound enhancing luminous efficiency and color purity, an organic light emitting diode and an organic light emitting device including the compound.

Description of the Related Art

As a display device has become larger, there exists a need for a flat display device with lower spacing occupation. Among the flat display devices, a display device using an organic light emitting diode (OLED) has come into the spotlight.

In the OLED, when electrical charges are injected into an emission layer between an electron injection electrode (i.e., cathode) and a hole injection electrode (i.e., anode), electrical charges are combined to be paired, and then emit light as the combined electrical charges are disappeared.

The OLED can be formed even on a flexible transparent substrate such as a plastic substrate. In addition, the OLED can be driven at a lower voltage of 10 V or less. Besides, the OLED has relatively lower power consumption for driving compared to plasma display panel and inorganic electroluminescent devices, and color purity thereof is very high. Further, since the OLED can display various colors such as green, blue, red and the likes, the OLED display device has attracted a lot of attention as a next-generation display device that can replace a liquid crystal display device (LCD).

Since material used as blue dopant must has wider band energy gap compared to green and/or red dopant, there have been difficulties in developing blue dopant. Besides, the OLED including the blue dopant shows very low luminous efficiency and poor color purity, and therefore, caused limitation in implementing full-color display.

BRIEF SUMMARY

Accordingly, the present disclosure is directed to an organic compound, an organic light emitting diode and an organic light emitting device including the organic compounds that can reduce one or more of the problems due to the limitations and disadvantages of the related art.

An object of the present disclosure is to provide an organic compound, an organic light emitting diode and an organic light emitting device that can enhance luminous efficiency and color purity.

Another object of the present disclosure is to provide an organic light emitting diode and an organic light emitting device that can lower driving voltage and power consumption, and can improve life span.

Additional features and advantages of the disclosure will be set forth in the description which follows, and in part will be apparent from the description, or can be learned by practice of the disclosure. The objectives and other advantages of the disclosure will be realized and attained by the structure particularly pointed out in the written description and claims hereof as well as the appended drawings.

According to an aspect, the present disclosure provides an organic compound represented by the following Chemical Formula 1:

Chemical Formula 1

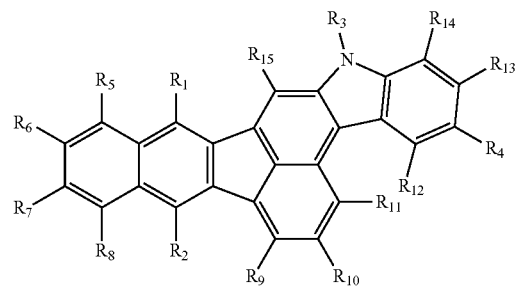

wherein each of $R_1$ to $R_3$ is independently $C_5$~$C_{30}$ aromatic group or $C_4$~$C_{30}$ hetero aromatic group, wherein each of the aromatic group and the hetero aromatic group is independently unsubstituted or substituted with linear or branched $C_1$~$C_{10}$ alkyl group or $C_1$~$C_{10}$ alkoxy group; $R_4$ is $C_5$~$C_{30}$ aromatic group or $C_4$~$C_{30}$ hetero aromatic group, wherein each of the aromatic group and the hetero aromatic group is independently unsubstituted or substituted with a group consisting of linear or branched $C_1$~$C_{10}$ alkyl group, $C_5$~$C_{30}$ aryl group, $C_4$~$C_{30}$ hetero aryl group and combination thereof; each of $R_5$ to $R_{15}$ is independently hydrogen or $C_1$~$C_{10}$ alkyl group.

According to another aspect, the present disclosure provides an organic light emitting diode (OLED) that comprises a first electrode; a second electrode facing the first electrode; and a first emitting material layer between the first and second electrode, wherein the first emitting material layer comprises the above organic compound.

According to still another aspect, the present disclosure provides an organic light emitting device that comprises a substrate and the OLED disposed over the substrate, as described above.

It is to be understood that both the foregoing general description and the following detailed description are examples and are explanatory and are intended to provide further explanation of the disclosure as claimed.

BRIEF DESCRIPTION OF THE SEVERAL VIEWS OF THE DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

DETAILED DESCRIPTION

Figure 1:
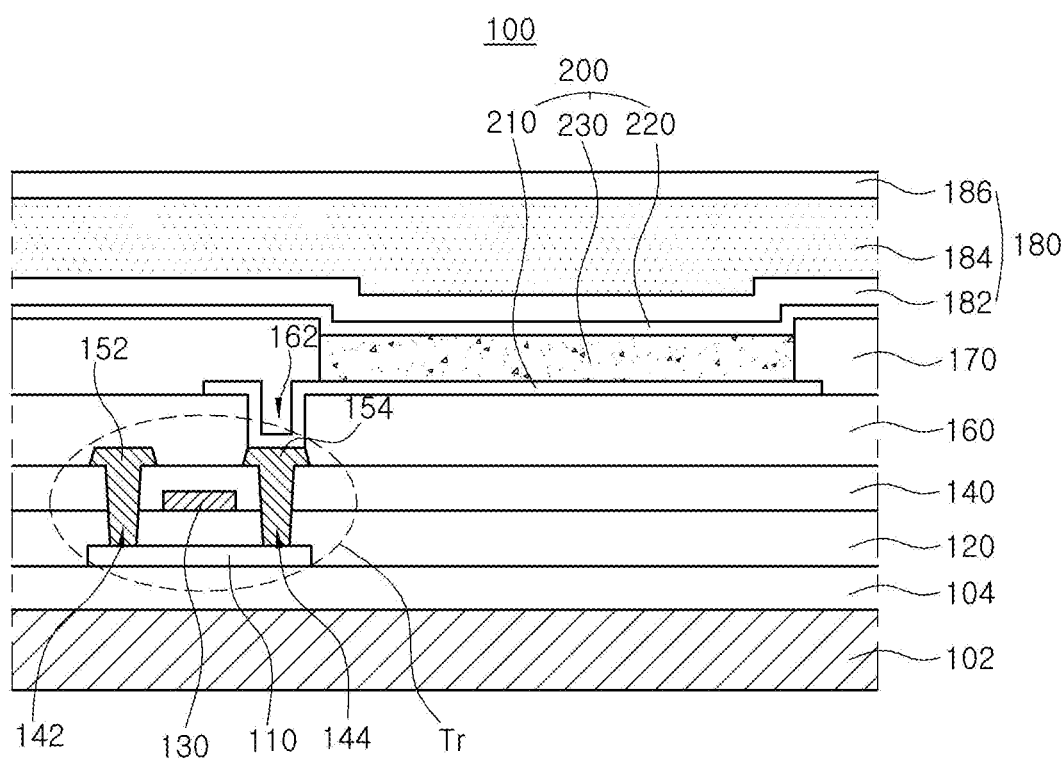
FIG. 1 is a schematic cross-sectional view illustrating an organic light emitting display device of the present disclosure.

Reference will now be made in detail to aspects of the disclosure, examples of which are illustrated in the accompanying drawings.

Organic Compound

An organic compound of the present disclosure has a benzofluorenocarbazole core consisting of multiple fused aromatic rings and aliphatic and/or aromatic groups bonded to specific positions of the benzofluorenocarbazole core. The organic compound of the present disclosure can be represented by the following Chemical Formula 1.

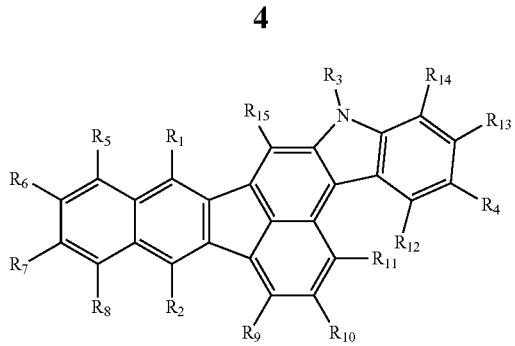

In Chemical Formula 1, each of $R_1$ to $R_3$ is independently $C_5 \sim C_{30}$ aromatic group or $C_4 \sim C_{30}$ hetero aromatic group, wherein each of the aromatic group and the hetero aromatic group in $R_1$ to $R_3$ is independently unsubstituted or substituted with linear or branched $C_1 \sim C_{10}$ alkyl group or $C_1 \sim C_{10}$ alkoxy group. $R_4$ is $C_5 \sim C_{30}$ aromatic group or $C_4 \sim C_{30}$ hetero aromatic group, wherein each of the aromatic group and the hetero aromatic group in $R_4$ is independently unsubstituted or substituted with a group consisting of linear or branched $C_1 \sim C_{10}$ alkyl group, $C_5 \sim C_{30}$ aryl group, $C_4 \sim C_{30}$ hetero aryl group and combination thereof. Each of $R_5$ to $R_{15}$ is independently hydrogen or $C_1 \sim C_{10}$ alkyl group.

As used herein, the term "unsubstituted" means that hydrogen atom is bonded, and in this case hydrogen atom includes protium, deuterium and tritium.

As used herein, the term "hetero" described in "hetero aromatic ring", "hetero aromatic group", "hetero alicyclic ring", "hetero cyclic alkyl group", "hetero aryl group", "hetero aralkyl group", "hetero aryloxyl group", "hetero aryl amino group", "hetero arylene group", "hetero aralkylene group", "hetero aryloxylene group", and the likes means that at least one carbon atoms, for example 1 to 5 carbon atoms, forming such aromatic or alicyclic rings are substituted with at least one hetero atoms selected from the group consisting of N, O, S and combination thereof.

In one embodiment, each of the $C_5 \sim C_{30}$ aromatic group of $R_1$ to $R_3$ can include, but are not limited to, $C_5 \sim C_{30}$ aryl group, $C_5 \sim C_{30}$ aralkyl group, $C_5 \sim C_{30}$ aryloxyl group and/or $C_5 \sim C_{30}$ aryl amino group, each of which is unsubstituted or substituted with linear or branched $C_1 \sim C_{10}$ alkyl group or $C_1 \sim C_{10}$ alkoxy group, respectively. In another embodiment, the $C_5 \sim C_{30}$ aromatic group of $R_4$ can include, but are not limited to, $C_5 \sim C_{30}$ aryl group, $C_5 \sim C_{30}$ aralkyl group, $C_5 \sim C_{30}$ aryloxyl group and/or $C_5 \sim C_{30}$ aryl amino group, each of which is unsubstituted or substituted with a group consisting of linear or branched $C_1 \sim C_{10}$ alkyl group, $C_5 \sim C_{30}$ aryl group, $C_4 \sim C_{30}$ hetero aryl group and combination thereof. For example, each of the $C_5 \sim C_{30}$ aryl group of $R_1$ to $R_4$ can include, but are not limited to, a non-fused or fused aryl group such as phenyl, biphenyl, terphenyl, tetraphenyl, naphthyl, anthracenyl, indenyl, phenalenyl, phenanthrenyl, azulenyl, pyreneyl, fluorenyl, tetracenyl, indacenyl or spiro fluorenyl, each of which can be unsubstituted or substituted with linear or branched $C_1 \sim C_{10}$ alkyl group, $C_1 \sim C_{10}$ alkoxy group, $C_5 \sim C_{30}$ aryl group, $C_4 \sim C_{30}$ hetero aryl group and combination thereof.

In another embodiment, each of the $C_4 \sim C_{30}$ hetero aromatic group of $R_1$ to $R_3$ can include, but are not limited to, $C_4 \sim C_{30}$ hetero aryl group, $C_4 \sim C_{30}$ hetero aralkyl group, $C_4 \sim C_{30}$ hetero aryloxyl group and/or $C_4 \sim C_{30}$ hetero aryl amino group, each of which is unsubstituted or substituted with linear or branched $C_1 \sim C_{10}$ alkyl group or $C_1 \sim C_{10}$ alkoxy group, respectively. In still another embodiment, the $C_4 \sim C_{30}$ hetero aromatic group of $R_4$ can include, but are not limited to, $C_4 \sim C_{30}$ hetero aryl group, $C_4 \sim C_{30}$ hetero aralkyl group, $C_4 \sim C_{30}$ hetero aryloxyl group and/or $C_4 \sim C_{30}$ hetero aryl amino group, each of which is unsubstituted or substituted with a group consisting of linear or branched $C_1 \sim C_{10}$ alkyl group, $C_5 \sim C_{30}$ aryl group, $C_4 \sim C_{30}$ hetero aryl group and combination thereof. For example, the $C_4 \sim C_{30}$ hetero aryl group of $R_1$ to $R_4$ can include, but are not limited to, unfused or fused hetero aryl group such as furanyl, thiophenyl, pyrrolyl, pyridyl, pyridinyl, pyrimidyl, pyrimidinyl, pyrazinyl, pyridazinyl, triazinyl, tetrazinyl, imidazolyl, pyrazolyl, indolyl, carbazolyl, benzocarbazolyl, dibenzocarbazolyl, indolocarbazolyl, indenocarbazolyl, benzofurannocarbazolyl, benzothienocarbazolyl, quinolinyl, iso-quinolinyl, phthalazinly, quinoxalinyl, cinnolinyl, quinazolinyl, benzoquinolinyl, beznoiso-quinolinyl, benzoquinoxalinyl, benzoquinazolinyl, acridinyl, phenanthrolyl, pyranyl, oxazinyl, oxazolyl, iso-oxazolyl, oxadiazolyl, triazolyl, dioxinyl, benzofuranyl, dibenzofuranyl, thiopyranyl, thiazinyl, benzothiophenyl, dibenzothiophenyl, thiazolyl, iso-thiazolyl, xanthenyl, spiro-xanthenyl, acridinyl, dihydro-acridinyl substituted with at least one $C_1 \sim C_{10}$ alkyl group, spiro-acridinyl, phenazinyl, spiro-phenazinyl, thiophenzinyl, spiro-thiophenazinyl, phenoxazinyl, thisphenzinyl, and the likes, each of which can be unsubstituted or substituted with linear or branched $C_1 \sim C_{10}$ alkyl group, $C_1 \sim C_{10}$ alkoxy group, $C_5 \sim C_{30}$ aryl group, $C_4 \sim C_{30}$ hetero aryl group and combination thereof.

In one embodiment, $C_5 \sim C_{30}$ aryl group or $C_4 \sim C_{30}$ hetero aryl group, which can be substituted to $R_4$, can include, but are not limited to, the aryl group such as phenyl and the likes of $R_1$ to $R_4$, or the hetero aryl group such as furanyl, and the likes of $R_1$ to $R_4$.

As an example, each of the linear or branched $C_1 \sim C_{10}$ alkyl group, $C_5 \sim C_{30}$ aryl group, $C_4 \sim C_{30}$ hetero aryl group and combination thereof, which can be substituted to any one of $R_1$ to $R_4$, can include only deuterium. Alternatively, each of those substituents can include at least one deuterium and/or tritium, respectively.

In one exemplary embodiment, when the number of the aromatic or hetero aromatic rings forming each of $R_1$ to $R_4$ and/or the number of the aromatic or hetero aromatic rings substituted to $R_4$ in Chemical Formula 1 becomes larger, the whole organic compound can have extremely long conjugated structures, and therefore, its energy level bandgap can be extremely lowered. For example, Each of $R_1$ to $R_4$ can include 1-3 rings, preferably 1-2 rings. Besides, each of $R_1$ to $R_4$ can include respectively 5-membered ring, 6-membered ring or 7-membered ring, preferably 6-membered ring, so that the organic compound can enhance charge transfer property.

The organic compound having the structure of Chemical Formula 1 includes a rigid conformation of benzofluorenocarbazole core and aromatic or hetero aromatic groups bonded to specific positions of the aromatic rings among the benzofluorenocarbazole core, thereby maximizing the steric hindrance of the entire organic compound.

Accordingly, the organic compound can exhibit narrow Stokes Shift, which can be defined as a difference between UV wavelength of maximum absorption (UV $\lambda_{max}$) and wavelength of maximum photoluminescence (PL $\lambda_{max}$) and can emit blue light having high color purity. Particularly, it is possible to realize hyper fluorescence having excellent luminous efficiency and color purity by using the organic compound as a fluorescent dopant, optionally a delayed fluorescent material, in an emissive layer of an organic light emitting diode, as described below.

As an example, each of $R_1$ to $R_3$ in Chemical Formula 1 can be independently selected from, but are not limited to, an aryl group and $R_4$ in Chemical Formula 1 can be selected from, but are not limited to, an aryl group or hetero aryl group. In one exemplary embodiment, the organic compound having the structure of Chemical Formula 1 can include, but are not limited to, an organic compound having the following structure of Chemical Formula 2:

Chemical Formula 2

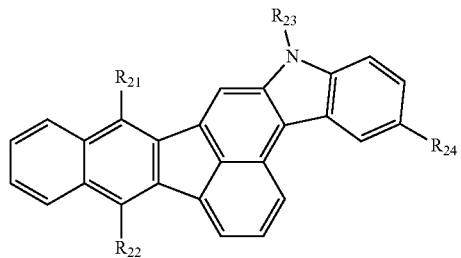

In Chemical Formula 2, each of $R_{21}$ to $R_{23}$ is independently $C_5 \sim C_{30}$ aryl group unsubstituted or substituted with linear or branched $C_1 \sim C_{10}$ alkyl group. $R_{24}$ is selected from the group consisting of phenyl, naphthyl, anthracenyl and pyridyl, wherein each of the phenyl, naphthyl, anthracenyl and pyridyl is independently unsubstituted or substituted with a group consisting of linear or branched $C_1 \sim C_{10}$ alkyl group, $C_5 \sim C_{30}$ aryl group, $C_4 \sim C_{30}$ hetero aryl group and combination thereof.

As an example, each of the linear or branched $C_1 \sim C_{10}$ alkyl group, $C_5 \sim C_{30}$ aryl group, $C_4 \sim C_{30}$ hetero aryl group and combination thereof, which can be substituted to any one of $R_{21}$ to $R_{24}$, can include only deuterium. Alternatively, each of those substituents can include at least one deuterium and/or tritium, respectively.

In one exemplary embodiment, $R_{24}$ in Chemical Formula 2 can include, but are not limited to, phenyl, naphthyl or pyridyl, each of which can be unsubstituted or substituted with a group consisting of linear or branched $C_1 \sim C_{10}$ alkyl group, naphthyl group and combination thereof.

The organic compound having the structure of Chemical Formula 2 includes aromatic or hetero aromatic groups each of which is bonded to specific position of the benzofluorenocarbazole core. As the organic compound having the structure of Chemical Formula 2 exhibits very narrow Stokes Shift because its maximum absorption wavelength moves toward longer wavelength range. Accordingly, as the overlapping area between the absorption wavelength range of the organic compound and the emission wavelength ranges of the delayed fluorescent material is increased, energy transfer efficiency from the delayed fluorescent material to the organic compound having the structure of Chemical Formula 2 can be enhanced. When the organic compound having the structure of Chemical Formula 2 is used as a fluorescent dopant, it is possible to enhance luminous efficiency of an OLED and to realize blue emission having high color purity.

As an example, each of $R_{21}$ to $R_{23}$ in Chemical Formula 2 can be phenyl and $R_{24}$ in Chemical Formula 2 can be phenyl, naphthyl, anthracenyl or pyridyl, each of which is unsubstituted or substituted with at least one $C_1 \sim C_5$ alkyl group, which can include at least one deuterium or tritium, or at least one aryl group such as phenyl, naphthyl. For example, the organic compound having the structure of Chemical Formulae 1 and 2 can include, but are not limited to, any one having the following structure of Chemical Formula 3.
Chemical Formula 3
Compound 1
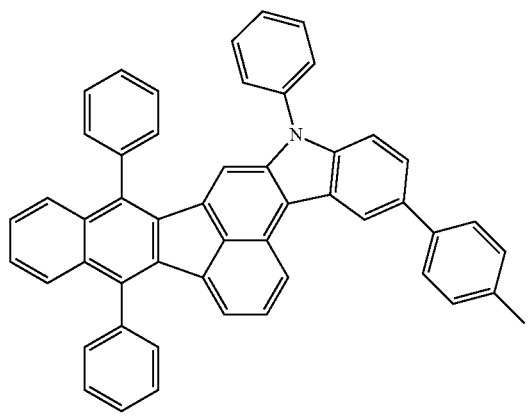
Compound 2
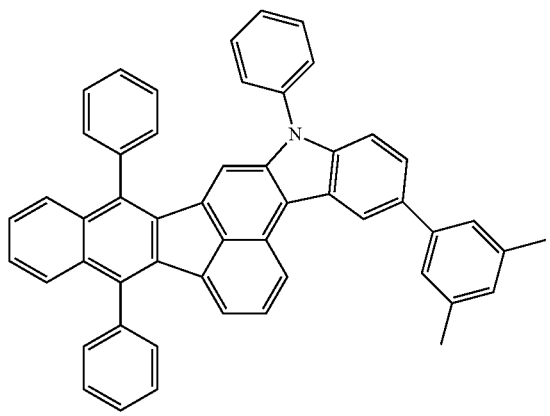
Compound 3
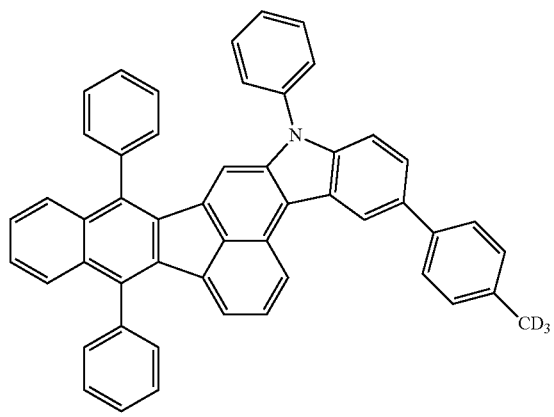
Compound 4
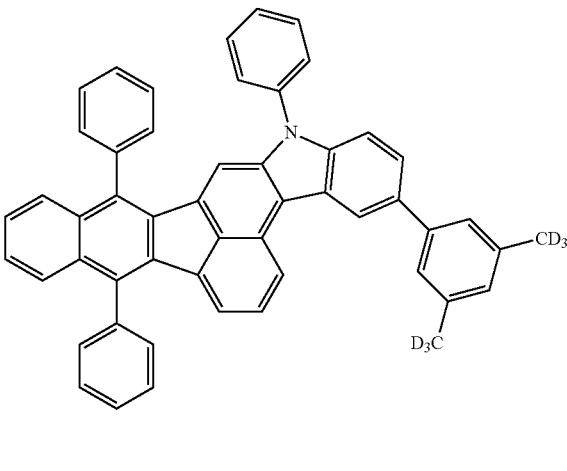
Compound 5
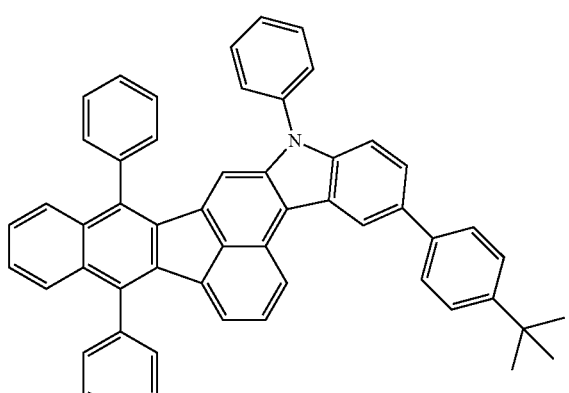
Compound 6
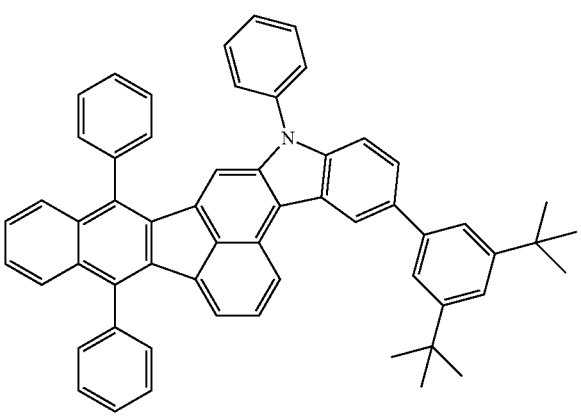

Compound 7
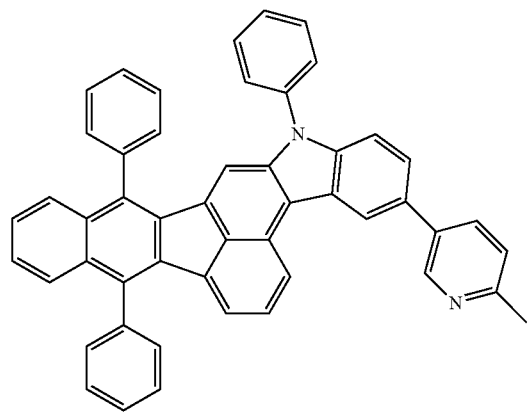
Compound 10
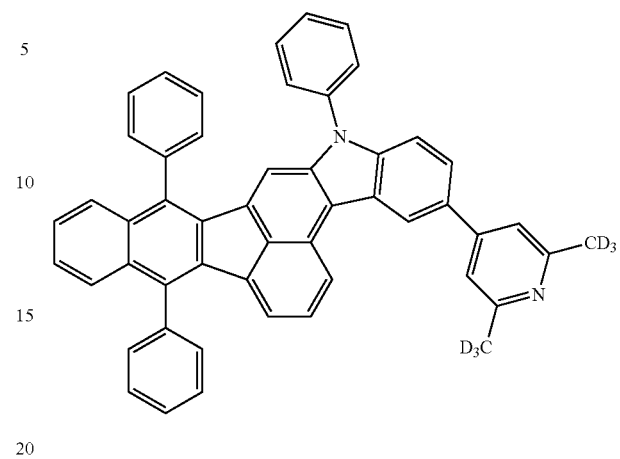
Compound 8
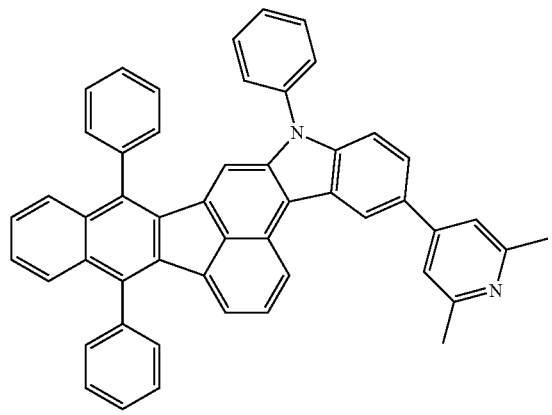
Compound 11
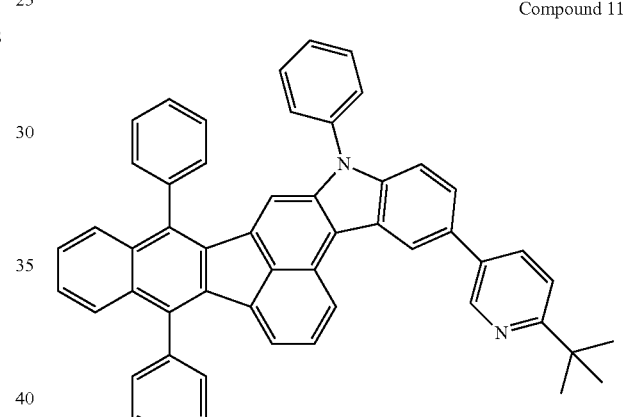
Compound 9
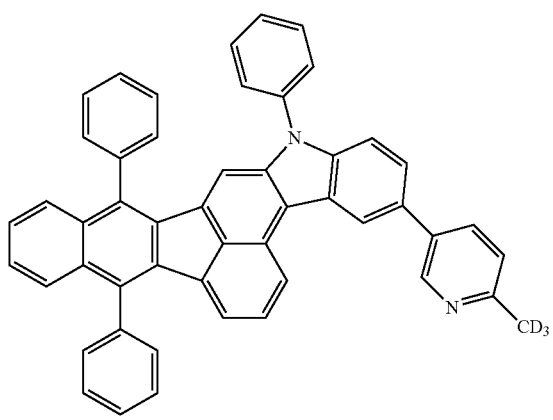
Compound 12
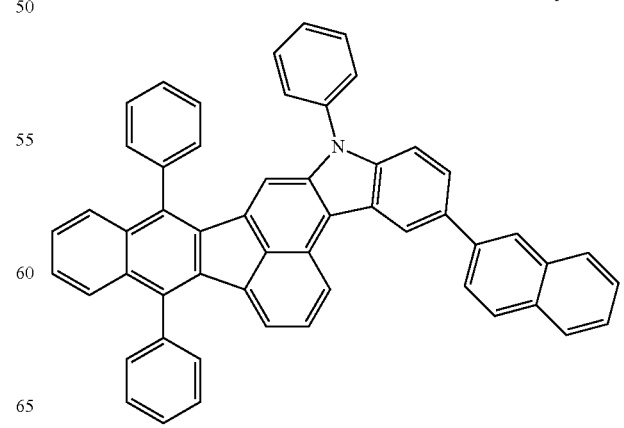

Compound 13

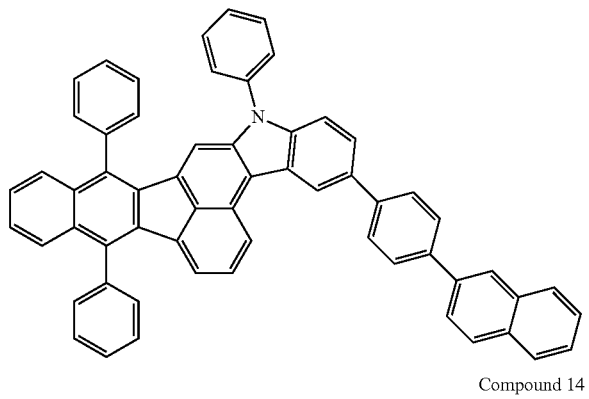

Compound 14

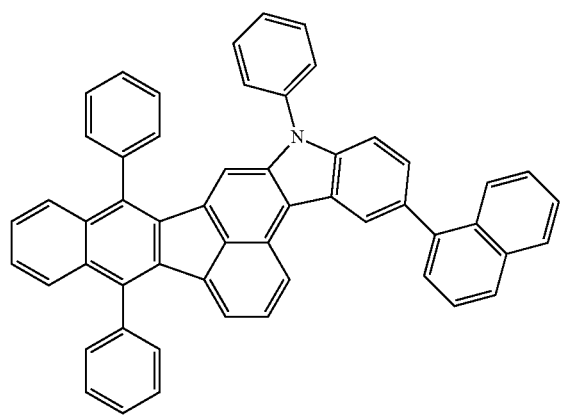

Compound 15

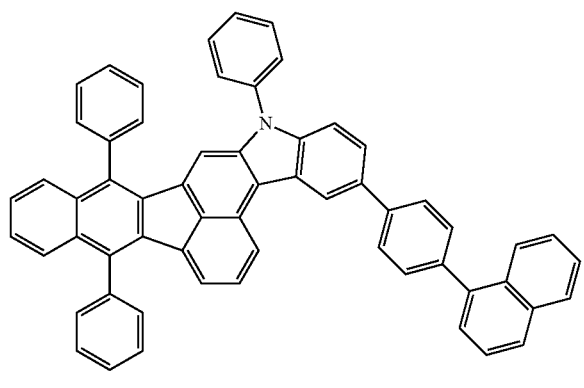

Compound 16

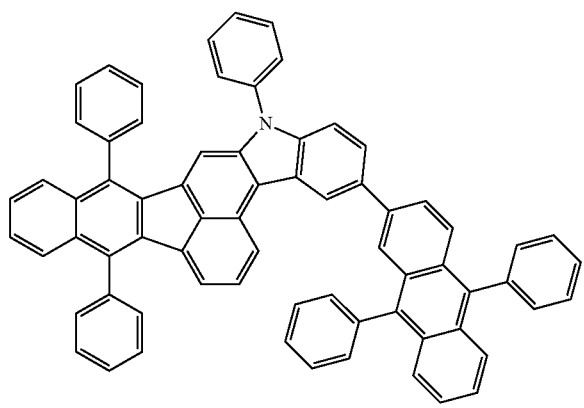

Compound 17

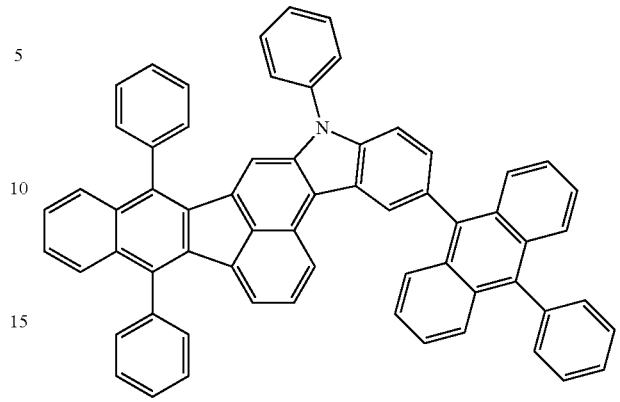

[Organic Light Emitting Diode and Device]

The organic compound having the structure of Chemical Formulae 1 to 3 can be applied to an emitting material layer of an organic light emitting diode so as to obtain blue emission light having high color purity and enhance luminous efficiency of the diode. The organic light emitting diode of the present disclosure can be applied to an organic light emitting device such as an organic light emitting display device and an organic light emitting illumination device. An organic light emitting display device will be explained. FIG. 1 is a schematic cross-sectional view of an organic light emitting display device in accordance with an exemplary embodiment of the present disclosure.

As illustrated in FIG. 1, the organic light emitting display device 100 includes a substrate 102, a thin-film transistor Tr on the substrate 102, and an organic light emitting diode 200 connected to the thin film transistor Tr.

The substrate 102 can include, but are not limited to, glass, thin flexible material and/or polymer plastics. For example, the flexible material can be selected from the group, but are not limited to, polyimide (PI), polyethersulfone (PES), polyethylenenaphthalate (PEN), polyethylene terephthalate (PET), polycarbonate (PC) and combination thereof. The substrate 102, over which the thin film transistor Tr and the organic light emitting diode 200 are arranged, form an array substrate.

A buffer layer 104 can be disposed over the substrate 102, and the thin film transistor Tr is disposed over the buffer layer 104. The buffer layer 104 can be omitted.

A semiconductor layer 110 is disposed over the buffer layer 104. In one exemplary embodiment, the semiconductor layer 110 can include, but are not limited to, oxide semiconductor materials. In this case, a light-shield pattern can be disposed under the semiconductor layer 110, and the light-shield pattern can prevent light from being incident toward the semiconductor layer 110, and thereby, preventing the semiconductor layer 110 from being deteriorated by the light. Alternatively, the semiconductor layer 110 can include, but are not limited to, polycrystalline silicon. In this case, opposite edges of the semiconductor layer 110 can be doped with impurities.

A gate insulating layer 120 formed of an insulating material is disposed on the semiconductor layer 110. The gate insulating layer 120 can include, but are not limited to, an inorganic insulating material such as silicon oxide ($SiO_x$) or silicon nitride ($SiN_x$).

A gate electrode 130 made of a conductive material such as a metal is disposed over the gate insulating layer 120 so as to correspond to a center of the semiconductor layer 110. While the gate insulating layer 120 is disposed over a whole area of the substrate 102 in FIG. 1, the gate insulating layer 120 can be patterned identically as the gate electrode 130.

An interlayer insulating layer 140 formed of an insulating material is disposed on the gate electrode 130 with covering over an entire surface of the substrate 102. The interlayer insulating layer 140 can include, but are not limited to, an inorganic insulating material such as silicon oxide ($SiO_x$) or silicon nitride ($SiN_x$), or an organic insulating material such as benzocyclobutene or photo-acryl.

The interlayer insulating layer 140 has first and second semiconductor layer contact holes 142 and 144 that expose both sides of the semiconductor layer 110. The first and second semiconductor layer contact holes 142 and 144 are disposed over opposite sides of the gate electrode 130 with spacing apart from the gate electrode 130. The first and second semiconductor layer contact holes 142 and 144 are formed within the gate insulating layer 120 in FIG. 1. Alternatively, the first and second semiconductor layer contact holes 142 and 144 are formed only within the interlayer insulating layer 140 when the gate insulating layer 120 is patterned identically as the gate electrode 130.

A source electrode 152 and a drain electrode 154, which are formed of a conductive material such as a metal, are disposed on the interlayer insulating layer 140. The source electrode 152 and the drain electrode 154 are spaced apart from each other with respect to the gate electrode 130, and contact both sides of the semiconductor layer 110 through the first and second semiconductor layer contact holes 142 and 144, respectively.

The semiconductor layer 110, the gate electrode 130, the source electrode 152 and the drain electrode 154 constitute the thin film transistor Tr, which acts as a driving element. The thin film transistor Tr in FIG. 1 has a coplanar structure in which the gate electrode 130, the source electrode 152 and the drain electrode 154 are disposed over the semiconductor layer 110. Alternatively, the thin film transistor Tr can have an inverted staggered structure in which a gate electrode is disposed under a semiconductor layer and a source and drain electrodes are disposed over the semiconductor layer. In this case, the semiconductor layer can comprise amorphous silicon.

Although not shown in FIG. 1, a gate line and a data line, which cross each other to define a pixel region, and a switching element, which is connected to the gate line and the data line is, can be further formed in the pixel region. The switching element is connected to the thin film transistor Tr, which is a driving element. Besides, a power line is spaced apart in parallel from the gate line or the data line, and the thin film transistor Tr can further include a storage capacitor configured to constantly keep a voltage of the gate electrode for one frame.

In addition, the organic light emitting display device 100 can include a color filter for absorbing a part of the light emitted from the organic light emitting diode 200. For example, the color filter can absorb a light of specific wavelength such as red (R), green (G) or blue (B). In this case, the organic light emitting display device 100 can implement full-color through the color filter.

For example, when the organic light emitting display device 100 is a bottom-emission type, the color filter can be disposed on the interlayer insulating layer 140 with corresponding to the organic light emitting diode 200. Alternatively, when the organic light emitting display device 100 is a top-emission type, the color filter can be disposed over the organic light emitting diode 200, that is, a second electrode 220.

A passivation layer 160 is disposed on the source and drain electrodes 152 and 154 over the whole substrate 102. The passivation layer 160 has a flat top surface and a drain contact hole 162 that exposes the drain electrode 154 of the thin film transistor Tr. While the drain contact hole 162 is disposed on the second semiconductor layer contact hole 154, it can be spaced apart from the second semiconductor layer contact hole 154.

The organic light emitting diode 200 includes a first electrode 210 that is disposed on the passivation layer 160 and connected to the drain electrode 154 of the thin film transistor Tr. The organic light emitting diode 200 further includes an emitting unit 230 as an emissive layer and a second electrode 220 each of which is disposed sequentially on the first electrode 210.

The first electrode 210 is disposed in each pixel region. The first electrode 210 can be an anode and include a conductive material having a relatively high work function value. For example, the first electrode 210 can include, but are not limited to, a transparent conductive material such as indium tin oxide (ITO), indium zinc oxide (IZO), indium tin zinc oxide (ITZO), tin oxide (SnO), zinc oxide (ZnO), indium cerium oxide (ICO), aluminum doped zinc oxide (AZO), and the likes.

In one exemplary embodiment, when the organic light emitting display device 100 is a top-emission type, a reflective electrode or a reflective layer can be disposed under the first electrode 210. For example, the reflective electrode or the reflective layer can include, but are not limited to, aluminum-palladium-copper (APC) alloy.

In addition, a bank layer 170 is disposed on the passivation layer 160 in order to cover edges of the first electrode 210. The bank layer 170 exposes a center of the first electrode 210.

An emitting unit 230 is disposed on the first electrode 210. In one exemplary embodiment, the emitting unit 230 can have a mono-layered structure of an emitting material layer. Alternatively, the emitting unit 230 can have a multiple-layered structure of a hole injection layer, a hole transport layer, an electron blocking layer, an emitting material layer, a hole blocking layer, an electron transport layer and/or an electron injection layer (See, FIGS. 3, 10, 12 and 14). In one embodiment, the organic light emitting diode 200 can have one emitting unit 230. Alternatively, the organic light emitting diode 200 can have multiple emitting units 230 to form a tandem structure.

The emitting unit 230 includes the organic compound having the structure of Chemical Formulae 1 to 3. For example, the organic compound having the structured of any one in Chemical Formulae 1 to 3 can be used as a dopant of the emitting unit 230, and the emitting unit 230 can include a host and other dopants.

The second electrode 220 is disposed over the substrate 102 above which the emitting unit 230 is disposed. The second electrode 220 can be disposed over a whole display area and can include a conductive material with a relatively low work function value compared to the first electrode 210. The second electrode 220 can be a cathode. For example, the second electrode 220 can include, but are not limited to, aluminum (Al), magnesium (Mg), calcium (Ca), silver (Ag), alloy thereof or combination thereof such as aluminum-magnesium alloy (Al—Mg).

In addition, an encapsulation film 180 can be disposed over the second electrode 220 in order to prevent outer moisture from penetrating into the organic light emitting diode 200. The encapsulation film 180 can have, but are not limited to, a laminated structure of a first inorganic insulating film 182, an organic insulating film 184 and a second inorganic insulating film 186.

Figure 2:
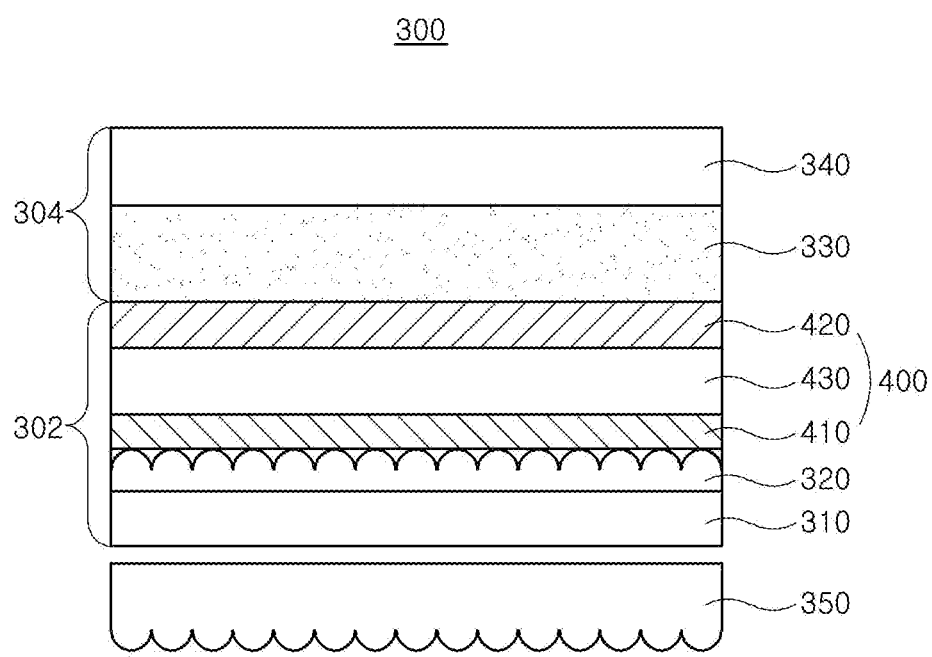
FIG. 2 is a schematic cross-sectional view illustrating an organic light emitting illumination device of the present disclosure.

An organic light emitting illumination device will be explained. FIG. 2 is a cross-sectional view illustrating an organic light emitting illumination device of the present disclosure. As illustrated in FIG. 2, the organic light emitting illumination device 300 includes a light emitting device member 302 where a surface emission occurs, and an encapsulation member 304 covering the light emitting device member 302. The light emitting device member 302 can include an organic light emitting diode 400 disposed on a substrate 310.

The substrate 310, can include, but are not limited to, glass, thin flexible material and/or polymer plastics. For example, the flexible material can be selected from the group, but are not limited to, PI, PES, PEN, PET, PC and combination thereof.

The organic light emitting diode 400 is disposed over the substrate 310. The organic light emitting diode 400 includes first and second electrodes 410 and 420 each of which is disposed over the whole substrate 310 and an emitting unit 430 disposed between the first and second electrodes 410 and 420. Accordingly, the emitting unit 430 illuminates and emits light toward the whole substrate 310 as electrical signals are applied into the first and second electrodes 410 and 420.

The first electrode 410 can be an anode and can include a conductive material having a relatively high work function value. For Example, the first electrode 410 can include, but are not limited to, a transparent conductive material such as ITO, IZO, ITZO, SnO, ZnO, ICO, AZO, and the likes. When the organic light emitting illumination device 300 is a top-emission type, a reflective electrode or a reflective layer can be disposed under the first electrode 410. For example, the reflective electrode or the reflective layer can include, but are not limited to, aluminum-palladium-copper (APC) alloy.

The emitting unit 430 is disposed on the first electrode 410. The emitting unit 430 can have a mono-layered structure of an emitting material layer. Alternatively, the emitting unit 430 can have a multiple-layered structure of a HIL, a HTL, an EBL, an EML, a HBL, an EIL, and/or an EIL (See, FIGS. 3, 10, 12 and 14). In one embodiment, the organic light emitting diode 400 can have one emitting unit 430. Alternatively, the organic light emitting diode 400 can have multiple emitting units 430 to form a tandem structure.

The emitting unit 430 includes the organic compound having the structure of Chemical Formulae 1 to 3. For example, the organic compound having the structured of any one in Chemical Formulae 1 to 3 can be used as a dopant of the emitting unit 430, and the emitting unit 430 can include a host and other dopants.

The second electrode 420 is disposed over the substrate 310 above which the emitting unit 430 is disposed. The second electrode 420 can be disposed over an entire surface of the substrate 310 and can include a conductive material with a relatively low work function value compared to the first electrode 410. The second electrode 420 can be a cathode. For example, the second electrode 420 can include, but are not limited to, Al, Mg, Ca, Au, and alloy thereof or combination thereof such as Al—Mg.

In one exemplary embodiment, an auxiliary electrode connecting to the first electrode 410 can be disposed over the substrate 310. The first electrode 410 includes a transparent conductive material in order to pass through light emitted from the emitting unit 430. But, the transparent conductive material has higher electrical resistance compared to metals. In case of fabricating the large-area light emitting diode illumination device 300, higher electrical resistance of the transparent conductive material makes the voltage applied to an emission area to be distributed unevenly across the whole emission area. Due to such uneven voltage distribution, uniform luminance cannot be realized in the large-area light emitting diode illumination device 300.

The auxiliary electrode can be disposed in the form of a matrix shape having a thin width, a mesh shape, a hexagonal shape, an octagonal shape and a circular shape, and the likes throughout the entire emission area. Accordingly, uniform voltage is distributed across the first electrode 410, which is disposed over the entire surface of the emission area, and thereby achieving uniform luminance emission across the large-area light emitting diode illumination device 300.

The auxiliary electrode can be disposed under the first electrode 410. Alternatively, the auxiliary electrode can be disposed on the first electrode 410. As an example, the auxiliary electrode can include, but are not limited to, highly conductive metals such as Al, Au, Cu, Ti, W, Mo and alloy thereof. In one exemplary embodiment, the auxiliary electrode has a double-layered structure. Alternatively, the auxiliary electrode can have a single-layered structure.

An adhesive or a tackifier 330 is applied over the organic light emitting diode 400, and a film 340 is disposed on the adhesive 330 to encapsulate the light emitting diode illumination device 300. The adhesive 330 can include photo-curable adhesives or thermally-curable adhesives. As an example, the adhesive 330 can include, but are not limited to, acrylate-based and/or epoxy-based pressure sensitive adhesives (PSA) and/or optically clear adhesives (OCA).

The film 340 can include various materials. The film 340 prevents outer moisture or air from filtrating into the organic light emitting diode 400 and can include any material to perform such function. As an example, the film 340 can include polymer such as polyethylene terephthalate (PET) or thin metal foil such as aluminum. In addition, when the light emitting diode illumination device 300 is fabricated with a sheet-manufacturing apparatus not a roll-manufacturing apparatus, the film 340 can include un-bend materials such as glass.

An encapsulation layer can be disposed on the second electrode 420. The encapsulation layer can include a first passivation layer of an organic layer and/or an inorganic layer, and a second passivation layer of epoxy-based compounds, acrylate-based compounds or acryl-based compounds.

Moreover, the organic light emitting illumination device 300 can further includes an inner coupling layer 320 disposed between the substrate 310 and the organic light emitting diode 400 for improving an external quantum efficiency (EQE) and/or an outer coupling layer 350 disposed under the substrate 310 for increasing haze.

The inner coupling layer 320 and the outer coupling layer 350 can include materials having a refractive index between about 1.7 and about 3.0 so that the organic light emitting diode can increase its out-coupling efficiency. Accordingly, light-scattering effect due to a refractive index difference between these coupling layers 320 and 350 and other layers having a relatively lower refractive index can be realized.

As an example, each of the inner and outer coupling layers 320 and 350 can have a structure where scattering particles are dispersed in a binder having a refractive index of about 1.7 to about 3.0. In addition, each of inner and outer coupling layers 320 and 350 can include a scattering layer where concave-convex structures due to the scattering particles are formed on the surface opposite surface in contact with the substrate 310, and a planarization layer for flattening the surface curvature due to the concave-convex structure of the scattering layer. The planarization layer can have a higher refractive index than the scattering particles, and the refractive index of the planarization layer can be about 1.7 to about 3.0.

The binder of the inner and outer coupling layers 320 and 350 is not particularly limited and can be an organic, inorganic or organic/inorganic hybrid or composite binder. As an example, the binder can be an inorganic or organic/inorganic hybrid or composite binder. The inorganic or the organic/inorganic hybrid or composite binder has better heat-resistance properties, chemical-resistance properties than the organic binder. Accordingly, it is possible to increase physical and chemical properties such as lifespan of the organic light emitting diode 400 and to fabricate various types of diodes using the inorganic or the organic/inorganic hybrid or composite binder since the inorganic or the organic/inorganic hybrid or composite binder is not deteriorated even in high-temperature processes, photo-processes and etching process performed at 150° C. or more in the course of fabricating the organic light emitting diode 400.

As an example, the binder can include, but are not limited to, inorganic materials or organic/inorganic hybrid materials selected from silicon oxides ($SiO_x$), silicon nitrides ($SiN_x$), silicon oxide nitrides ($SiO_xN_y$), alumina ($Al_2O_3$), siloxane-based materials, and combination thereof. For example, a siloxane-based inorganic binder can be fabricated by performing condensation polymerization process using siloxanes, or the organic/inorganic hybrid binders can include a material having alkyl groups in the siloxane-based materials.

The scattering particle of the inner and outer coupling layers 320 and 350 can be spherical, ellipsoidal or amorphous, and preferably spherical or ellipsoidal. The scattering particle can have a mean particle size between about 100 nm and about 300 nm, and preferably about 150 nm and about 200 nm. The scattering particle can include any material that can scatter lights using the refractive index difference between the binder or the planarization layer As an example, the scattering particle can include, but are not limited to, silicon, silica, glass, titanium oxide, magnesium fluoride, zirconium oxide, alumina, cerium oxide, hafnium oxide, niobium pentoxide, tantalum pentoxide, indium oxide, tin oxide, indium-tin oxide, zinc oxide, zinc sulfide, calcium carbonate, barium sulfonate, silicon nitrides, aluminum nitrides and combination thereof. As an example, the scattering particle can be titanium dioxide.

As described above, the emitting units 230 and 430 of the OLED 200 and 400 uses the organic compound having the structure of Chemical Formulae 1 to 3 as a luminous material. The organic compound has a conformationally stable benzofluorenocarbazole core and aromatic groups bonded to specific positions of the benzofluorenocarbazole core.

It is possible to manufacture the organic light emitting diodes 200 and 400 and an organic light emitting devices 100 and 300 that can enhance their color purity and luminous efficiency as well as improve their luminous life span.

Figure 3:
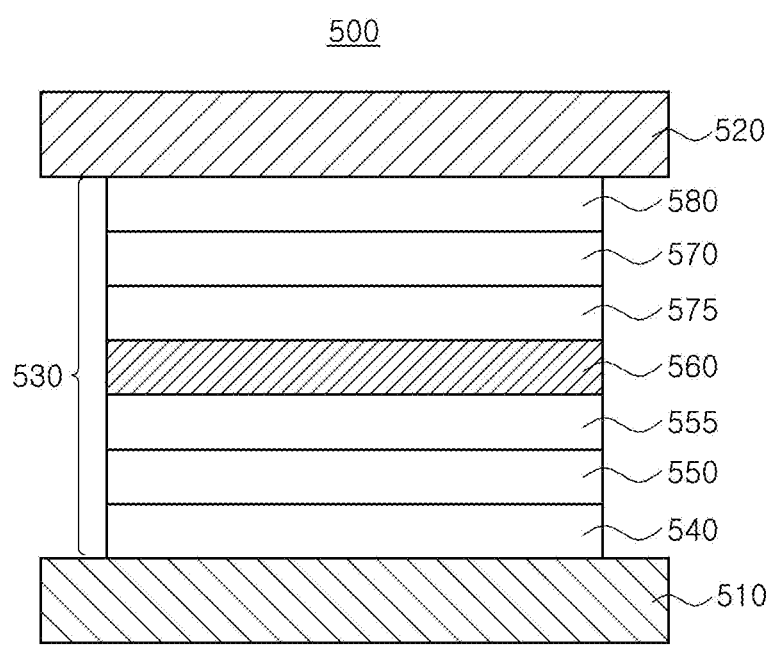
FIG. 3 is a schematic cross-sectional view illustrating an organic light emitting diode in accordance with an exemplary embodiment of the present disclosure.

FIG. 3 is a schematic cross-sectional view illustrating an organic light emitting diode having a single-layered EML in accordance with an exemplary embodiment of the present disclosure. As illustrated in FIG. 3, the organic light emitting diode (OLED) 500 in accordance with the first embodiment of the present disclosure includes first and second electrodes 510 and 520 facing each other, an emitting unit 530 as an emissive layer disposed between the first and second electrodes 510 and 520. In one exemplary embodiment, the emitting unit 530 include a hole injection layer (HIL) 540, a hole transport layer (HTL) 550, an emitting material layer (EML) 560, an electron transport layer (ETL) 570 and an electron injection layer (EIL) 580 each of which is laminated sequentially from the first electrode 510. Alternatively, the emitting unit 530 can include a first exciton blocking layer, i.e. an electron blocking layer (EBL) 555 disposed between the HTL 550 and the EML 560 and/or a second exciton blocking layer, i.e. a hole blocking layer (HBL) 575 disposed between the EML 560 and the ETL 570.

The first electrode 510 can be an anode that provides a hole into the EML 560. The first electrode 510 can include, but are not limited to, a conductive material having a relatively high work function value, for example, a transparent conductive oxide (TCO). In an exemplary embodiment, the first electrode 510 can include, but are not limited to, ITO, IZO, ITZO, SnO, ZnO, ICO, AZO, and the likes.

The second electrode 520 can be a cathode that provides an electron into the EML 560. The second electrode 520 can include, but are not limited to, a conductive material having a relatively low work function values, i.e., a highly reflective material such as Al, Mg, Ca, Ag, alloy thereof, combination thereof, and the likes.

The HIL 540 is disposed between the first electrode 510 and the HTL 550 and improves an interface property between the inorganic first electrode 510 and the organic HTL 550. In one exemplary embodiment, the HIL 540 can include, but are not limited to, 4,4'4"-Tris(3-methylphenylamino)triphenylamine (MTDATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino) triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4"-diamine (NPB; NPD), 1,4,5,8,9,11-Hexaazatriphenylenehexacarbonitrile (Dipyrazino[2,3-f: 2'3'-h]quinoxaline-2,3,6,7,10,11-hexacarbonitrile; HAT-CN), 1,3,5-tris[4-(diphenylamino)phenyl] benzene (TDAPB), poly(3,4-ethylenedioxythiophene)polystyrene sulfonate (PEDOT/PSS) and/or N-(biphenyl-4-yl)-9,9-dimethyl-N-(4-(9-phenyl-9H-carbazol-3-yl)phenyl)-9H-fluoren-2-amine. The HIL 540 can be omitted in compliance with a structure of the OLED 500.

The HTL 550 is disposed adjacently to the EML 560 between the first electrode 510 and the EML 560. In one exemplary embodiment, the HTL 550 can include, but are not limited to, N,N'-Diphenyl-N,N'-bis(3-methylphenyl)-1, 1'-biphenyl-4,4'-diamine (TPD), NPB, 4,4'-bis(N-carbazolyl)-1,1'-biphenyl (CBP), Poly[N,N'-bis(4-butylpnehyl)-N,N'-bis(phenyl)-benzidine] (Poly-TPD), Poly[(9,9-dioctylfluorenyl-2,7-diyl)-co-(4,4'-(N-(4-sec-butylphenyl) diphenylamine))] (TFB), Di-[4-(N,N-di-p-tolyl-amino)-phenyl]cyclohexane (TAPC), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The EML 560 can include a host doped with a dopant. In this exemplary embodiment, the EML 560 can include a host (a first host) and the organic compound having the structure of any one of Chemical Formulae 1 to 3 as a fluorescent dopant (a first dopant). The EML 560 can include the fluorescent dopant by about 1 to about 50% by weight and can emit blue color.

Figure 4:
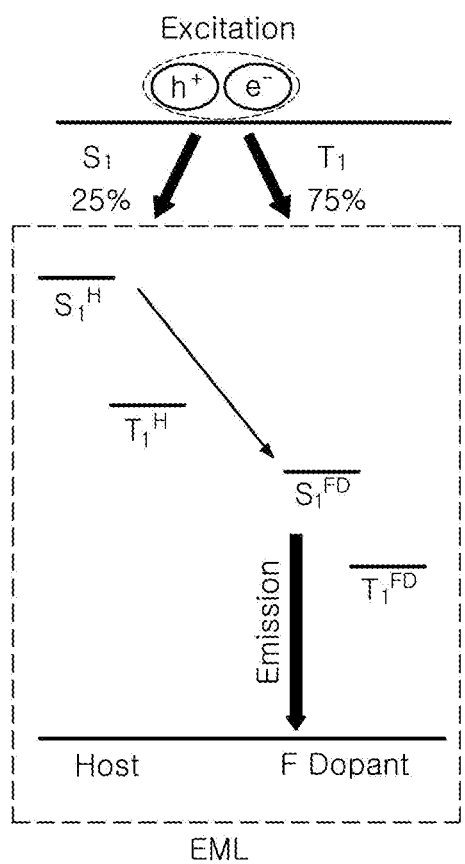
FIG. 4 is a schematic diagram illustrating luminous mechanism by energy level bandgap between luminous materials in accordance with an exemplary embodiment of the present disclosure.

When the EML 560 includes the host and the organic compound having the structure of any one of Chemical Formulae 1 to 3 as the fluorescent dopant, it can be necessary to adjust excited state singlet and triplet energy levels of the host and the fluorescent dopant. FIG. 4 is s schematic diagram illustrating luminous mechanism by energy level bandgap between luminous materials in accordance with an exemplary embodiment of the present disclosure.

As illustrated in FIG. 4, each of an excited state singlet energy level $S_1^H$ and an excited state triplet energy level $T_1^H$ of the first host is higher than each of an excited state singlet energy level $S_1^{FD}$ and an excited state triplet energy level $T_1^{FD}$ of the first fluorescent dopant, respectively, so that exciton energy generated in the first host can be transferred to the fluorescent dopant. As an example, it is preferable that overlapping area between the emission wavelength range of the host and the absorption wavelength of the fluorescent dopant is large in order to transfer exciton energy efficiently from the first host to the fluorescent dopant.

In one exemplary embodiment, the host of the EML 560 can include, but are not limited to, 9-(3-(9H-carbazol-9-yl)phenyl)-9H-carbazole-3-carbonitrile (mCP-CN), CBP, 3,3'-bis(N-carbazolyl)-1,1'-biphenyl (mCBP), 1,3-Bis(carbazol-9-yl)benzene (mCP), Oxybis(2,1-phenylene))bis(diphenylphosphine oxide (DPEPO), 2,8-Bis(diphenylphosphoryl)dibenzothiophene (PPT), 1,3,5-Tri[(3-pyridyl)-phen-3-yl]benzene (TmPyPB), 2,6-Di(9H-carbazol-9-yl)pyridine (PYD-2Cz), 2,8-di(9H-carbazol-9-yl)dibenzothiophene (DCzDBT), 3',5'-Di(carbazol-9-yl)-[1,1'-biphenyl]-3,5-dicarbonitrile (DCzTPA), 4'-(9H-carbazol-9-yl)biphenyl-3,5-dicarbonitrile (pCzB-2CN), 3-(9H-carbazol-9-yl)biphenyl-3,5-dicarbonitrile (mCzB-2CN), Diphenyl-4-triphenylsilylphenyl-phosphine oxide (TPSO1), 9-(9-phenyl-9H-carbazol-6-yl)-9H-carbazole (CCP), 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin-3-yl)-9H-3,9'-bicarbazole.

When the EML 560 includes the host and the fluorescent dopant, which can be the organic compound having the structure of any one of Chemical Formulae 1 to 3, the fluorescent dopant can be doped with, but are not limited to, about 1% to about 50% by weight, and preferably by about 1% to about 30% by weight.

Returning to FIG. 3, The ETL 570 and the EIL 580 are laminated sequentially between the EML 560 and the second electrode 520. The ETL 570 can include a material having high electron mobility so as to provide electrons stably with the EML 560 by fast electron transportation.

In one exemplary embodiment, the ETL 570 can include, but are not limited to, oxadiazole-based compounds, triazole-based compounds, phenanthroline-based compounds, benzoxazole-based compounds, benzothiazole-based compounds, benzimidazole-based compounds, triazine-based compounds, and the likes.

As an example, the ETL 570 can include, but are not limited to, tris-(8-hydroxyquinoline aluminum ($Alq_3$), 2-biphenyl-4-yl-5-(4-t-butylphenyl)-1,3,4-oxadiazole (PBD), spiro-PBD, lithium quinolate (Liq), 1,3,5-Tris(N-phenyl-benzimidazol-2-yl)benzene (TPBi), Bis(2-methyl-8-quinolinolato-N1,O8)-(1,1'-biphenyl-4-olato)aluminum (BAlq), 4,7-diphenyl-1,10-phenanthroline (Bphen), 2,9-Bis(naphthalene-2-yl)4,7-diphenyl-1,10-phenanthroline (NBphen), 2,9-Dimethyl-4,7-diphenyl-1,10-phenathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl)1,3,5-triazine (TmPPPyTz), Poly[9,9-bis(3'-(N,N-dimethyl)-N-ethylammonium)-propyl)-2,7-fluorene]-alt-2,7-(9,9-dioctylfluorene)] (PFNBr) and/or tris(phenylquinoxaline) (TPQ).

The EIL 580 is disposed between the second electrode 520 and the ETL 570, and can improve physical properties of the second electrode 520 and therefore, can enhance the life span of the OLED 500. In one exemplary embodiment, the EIL 580 can include, but are not limited to, an alkali halide such as LiF, CsF, NaF, $BaF_2$ and the likes, and/or an organic metal compound such as lithium benzoate, sodium stearate, and the likes.

When holes are transferred to the second electrode 520 via the EML 560 and/or electrons are transferred to the first electrode 510 via the EML 560, the OLED 500 can have short life span and reduced luminous efficiency. In order to prevent these phenomena, the OLED 500 in accordance with this embodiment of the present disclosure has at least one exciton blocking layer adjacent to the EML 560.

For example, the OLED 500 of the exemplary embodiment includes the EBL 555 between the HTL 550 and the EML 560 so as to control and prevent electron transfers. In one exemplary embodiment, the EBL 555 can include, but are not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, N,N'-bis[4-(bis(3-methylphenyl)amino)phenyl]-N,N'-diphenyl-[1,1'-biphenyl]-4,4'-diamine (DNTPD), TDAPB and/or 3,6-bis(N-carbazolyl)-N-phenyl-carbazole.

In addition, the OLED 500 further includes the HBL 575 as a second exciton blocking layer between the EML 560 and the ETL 570 so that holes cannot be transferred from the EML 560 to the ETL 570. In one exemplary embodiment, the HBL 575 can include, but are not limited to, oxadiazole-based compounds, triazole-based compounds, phenanthroline-based compounds, benzoxazole-based compounds, benzothiazole-based compounds, benzimidazole-based compounds, and triazine-based compounds.

For example, the HBL 575 can include a compound having a relatively low HOMO energy level compared to the emitting material in EML 560. The HBL 575 can include, but are not limited to, BCP, BAlq, $Alq_3$, PBD, spiro-PBD, Liq, Bis-4,5-(3,5-di-3-pyridylphenyl)-2-methylpyrimidine (B3PYMPM), DPEPO, 9-(6-(9H-carbazol-9-yl)pyridine-3-yl)-9H-3,9'-bicarbazole and combination thereof.

The organic compound having the structure of any one of Chemical Formulae 1 to 3 includes the benzofluorenocarbazole core and aromatic or hetero aromatic groups bonded to specific positions of the benzofluorenocarbazole core. The organic compound has narrow FWHM (full width at half maximum), so that the OLED 500 can have enhanced color purity.

Figure 5:
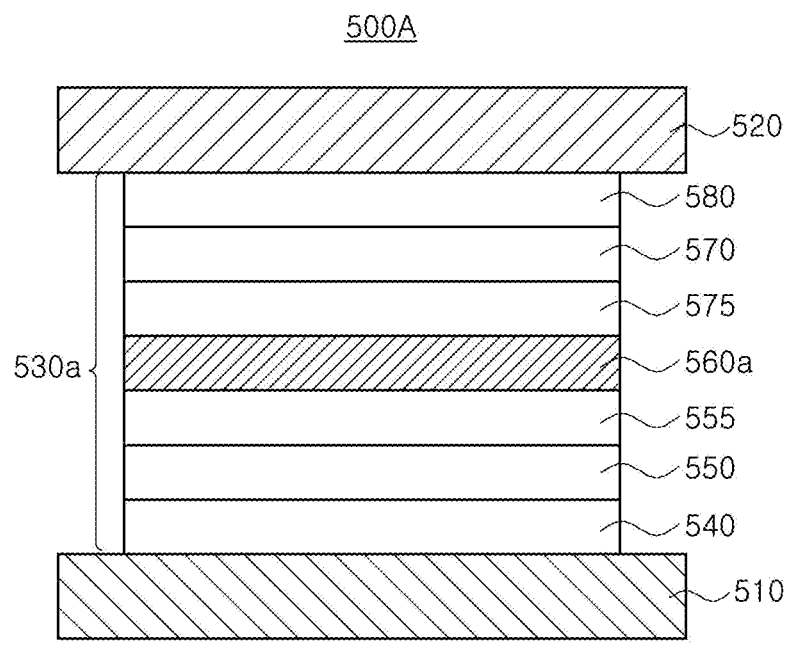
FIG. 5 is a schematic cross-sectional view illustrating an organic light emitting diode in accordance with another exemplary embodiment of the present disclosure.

While the EML 560 includes only a host and a fluorescent dopant in the above embodiment, another EML can have two or more dopants. FIG. 5 is a schematic cross-sectional view of an OLED having a single-layered EML in accordance with another exemplary embodiment of the present disclosure. As illustrated in FIG. 5, the OLED 500A in accordance with second embodiment of the present disclosure includes first and second electrodes 510 and 520 facing each other and an emitting unit 530a as an emissive layer disposed between the first and second electrodes 510 and 520.

In one exemplary embodiment, the emitting unit 530a can include an HIL 540, an HTL 550, an EML 560a, an ETL 570 and an EIL 580 each of which is laminated sequentially from the first electrode 510. The emitting unit 530a can further include an EBL 555 disposed between the HTL 550 and the EML 560a and an HBL 575 disposed between the EML 560a and the ETL 570. The OLED 500A can include the same structure and the same materials except the EML 560a compared to the OLED 500.

The EML 560a includes a host (a first host), a first dopant and a second dopant. The first dopant can be a delayed fluorescent dopant (T dopant) and the second dopant can be a fluorescent dopant (F dopant). In this case, the organic compound having the structure of any one of Chemical Formulae 1 to 3 can be used as the second dopant. When the EML 560a includes the delayed fluorescent dopant, the OLED 500A can enhance further its luminous efficiency by adjusting energy levels among the host and the dopants.

An Organic Light Emitting Diode (OLED) emits light as holes injected from the anode and electrons injected from the cathode are combined to form excitons in EML and then unstable excited state excitons return to a stable ground state. Theoretically, when electrons meet holes to form exciton, a singlet exciton of a paired spin and a triplet exciton of an unpaired spin are produced by a ratio of 1:3 by spin arrangements. Only the singlet exciton among the excitons can be involved in emission process in case of fluorescent materials. Accordingly, the OLED can exhibit luminous efficiency by maximum 5% in case of using the common fluorescent material.

In contrast, phosphorescent materials use different luminous mechanism of converting both singlet excitons and triplet exciton into light. The phosphorescent materials can convert singlet excitons into triplet excitons through inter-system crossing (ICT). Therefore, it is possible to enhance luminous efficiency in case of applying the phosphorescent materials that use both the singlet excitons and the triplet excitons during the luminous process compared to the fluorescent materials.

In case of using metal complexes having a heavy metal such as Ir, Pt, and the likes as the phosphorescent materials, it is possible to convert triplet state to singlet state through strong spin-orbital bonds by the heavy metal. However, prior art blue phosphorescent materials exhibits too low color purity to apply with the display device and exhibit very short luminous life span, and therefore, they have not been used in commercial display devices.

In this embodiment, the EML 560a includes the delayed fluorescent dopant as the first dopant so as to solve the problems accompanied by the conventional fluorescent materials and the phosphorescent materials. In an exemplary embodiment, the delayed fluorescent material is thermally-activated delayed fluorescent (TADF) material.

Since the triplet excitons within the delayed fluorescent material can be activated by heat or electrical field generated during driving the diode, the triplet excitons can be involved in emission processes. Since the delayed fluorescent material generally has both an electron donor moiety and an electron acceptor moiety, it can be converted to an intramolecular charge transfer (ICT) state. In case of using the delayed fluorescent material as a dopant, it is possible to use both the excitons of singlet energy level $S_1$ and the excitons of triplet energy level $T_1$ during the emission process.

Figure 6:
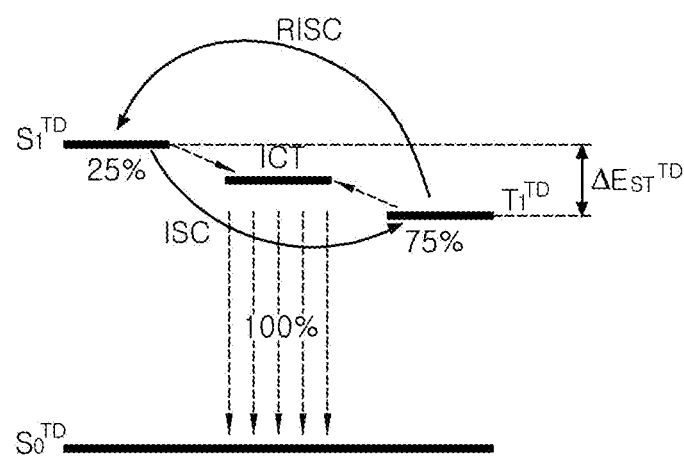
FIG. 6 is a schematic diagram illustrating luminous mechanism of the delayed fluorescent material in an EML in accordance with another exemplary embodiment of the present disclosure.

The luminous mechanism of the delayed fluorescent material will be explained with referring to FIG. 6, which is a schematic diagram illustrating a luminous mechanism of the delayed fluorescent material in an EML in accordance with another exemplary embodiment of the present disclosure. As illustrated in FIG. 6, both the excitons of singlet energy level $S_1^{TD}$ and the excitons of triplet energy level $T_1^{TD}$ in the delayed fluorescent material can move to an intermediate energy level state, i.e. ICT state, and then the intermediate stated excitons can be transferred to a ground state ($S_0$; $S_1 \rightarrow ICT \leftarrow T_1$). Since the excitons of singlet energy level $S_1^{TD}$ as well as the excitons of triplet energy level $T_1^{TD}$ in the delayed fluorescent material is involved in the emission process, the delayed fluorescent material can improve luminous efficiency.

Since both the Highest Occupied Molecular Orbital (HOMO) and the Lowest Unoccupied Molecular orbital (LUMO) are widely distributed over the whole molecule within the common fluorescent material, it is not possible to inter-convert between the singlet energy level and the triplet energy level within it (selection rule). In contrast, since the delayed fluorescent material, which can be converted to ICT state, has little orbital overlaps between HOMO and LUMO, there is little interaction between the HOMO state molecular orbital and the LUMO state molecular orbital in the state where dipole moment is polarized within the delayed fluorescent material. As a result, the changes of spin states of electrons does not have an influence on other electrons, and a new charge transfer band (CT band) that does not follow the selection rule is formed in the delayed fluorescent material.

In other words, since the delayed fluorescent material has the electron acceptor moiety spacing apart from the electron donor moiety within the molecule, it exists as a polarized state having a large dipole moment within the molecule. As the interaction between HOMO molecular orbital and LUMO molecular orbital becomes little in the state where the dipole moment is polarized, both the triplet energy level excitons and the singlet energy level excitons can be converted to ICT state. Accordingly, the excitons of triplet energy level $T_1$ as well as the excitons of singlet energy level $S_1$ can be involved in the emission process.

In case of driving the diode that includes the delayed fluorescent material, 25% excitons of singlet energy level $S_1^{TD}$ and 75% excitons of triplet energy level $T_1^{TD}$ are converted to ICT state by heat or electrical field, and then the converted excitons transfer to the ground state $S_0$ with luminescence. Therefore, the delayed fluorescent material can have 100% internal quantum efficiency in theory.

The delayed fluorescent material must has an energy level bandgap $\Delta E_{ST}^{TD}$ equal to or less than about 0.3 eV, for example, from about 0.05 to about 0.3 eV, between the singlet energy level $S_1^{TD}$ and the triplet energy level $T_1^{TD}$ so that exciton energy in both the singlet energy level and the triplet energy level can be transferred to the ICT state. The material having little energy level bandgap between the singlet energy level $S_1^{TD}$ and the triplet energy level $T_1^{TD}$ can exhibit common fluorescence with Inter system Crossing (ISC) in which the excitons of singlet energy level $S_1^{TD}$ can be transferred to the excitons of triplet energy level $T_1^{TD}$, as well as delayed fluorescence with Reverse Inter System Crossing (RISC) in which the excitons of triplet energy level $T_1^{TD}$ can be transferred upwardly to the excitons of single energy level $S_1^{TD}$, and then the exciton of singlet energy level $S_1^{TD}$ transferred from the triplet energy level $T_1^{TD}$ can be transferred to the ground state $S_0$.

Since the delayed fluorescent material can exhibit 100% internal quantum efficiency in theory, it can realize as high luminous efficiency as the conventional phosphorescent material including a heavy metal. However, the delayed fluorescent material has low luminous life span owing to using the triplet energy as well as the singlet energy. Besides, due to the bond conformation between the electron acceptor and the electron donor and sterical twists within the delayed fluorescent material, and additional charge transfer transition (CT transition) caused thereby, the delayed fluorescent materials show emission spectra having very broad FWHM in the course of emission, which results in poor color purity. That is, since the delayed fluorescent material utilizes a triplet exciton, it has a short life span, and has a limit in terms of color purity due to its wide FWHM because it emits light by the CT emission mechanism.

In this exemplary embodiment, it is possible to implement hyper-fluorescence by using the delayed fluorescent material as the first dopant so as to raise a generation ratio of the singlet exciton in the fluorescent material that can use only the singlet exciton energy. Since the delayed fluorescent material can utilize the triplet exciton energy as well as the singlet exciton energy, the fluorescent material can absorb the exciton energy emitted from the delayed fluorescent material, and therefore, the exciton energy absorbed by the fluorescent material can be utilized in the emission process with generating 100% singlet exciton.

In one exemplary embodiment of the present disclosure, the EML 560a includes the first host, a first dopant (delayed fluorescent dopant, TD) and the organic compound having the structure of any one of Chemical Formulae 1 to 3 as the second dopant (fluorescent dopant, FD) so as to prevent the color purity of the OLED 500A from being lowered in spite of using the delayed fluorescent material as the first dopant. In this case, it is important to adjust energy levels among the host and the dopants to transfer exciton energy from the host to the second dopant through the first dopant.

Figure 7:
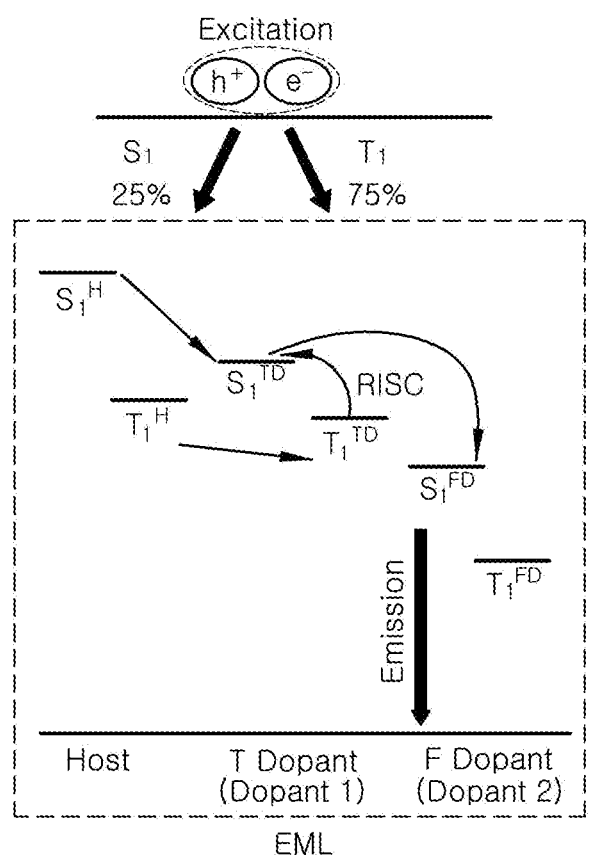
FIG. 7 is a schematic diagram illustrating luminous mechanism by energy level bandgap among luminous materials in accordance with another exemplary embodiment of the present disclosure.

FIG. 7 is a schematic diagram illustrating luminous mechanism by energy level bandgap among the luminous materials in a single-layered EML in accordance with another exemplary embodiment of the present disclosure. The exciton energy generated in the host must be firstly transferred to the first dopant (T dopant), which can be the delayed fluorescent material. In order to implement such energy transfer, each of an excited state singlet energy level $S_1^H$ and an excited state triplet energy level $T_1^H$ of the host must be higher than an excited state singlet energy level $S_1^{TD}$ and an excited state triplet energy level $T_1^{TD}$ of the delayed fluorescent dopant, respectively, as illustrated in FIG. 7

As an example, when the excited state triplet energy level $T_1^H$ of the host is not higher enough than the excited state triplet energy level $T_1^{TD}$ of the first dopant, which can be the fluorescent material, the excitons of the triplet state energy level $T_1^{TD}$ of the first dopant can be reversely transferred to the excited state triplet energy level $T_1^H$ of the host, which cannot utilize the triplet energy exciton during the light emission process. Accordingly, the excitons of the triplet state level $T_1^{TD}$ of the first dopant can be quenched as non-emission and they cannot be involved during the light emission process. For example, the excited state triplet energy level $T_1^H$ of the host can be high by at least 0.2 eV compared to the excited state triplet energy level $T_1^{TD}$ of the first dopant.

Also, the first dopant must have the energy level bandgap ($\Delta_{ES}^{TD}$) between the singlet energy level $S_1^{TD}$ and the triplet energy level $T_1^{TD}$ of at most 0.3 eV in order to realize a delayed fluorescence (See, FIG. 6). In contrast, an energy level bandgap between the singlet energy level $S_1^H$ and the triplet energy level $T_1^H$ of the host, and an energy level bandgap between the singlet energy level $S_1^{FD}$ and the triplet energy level $T_1^{FD}$ of the second dopant, which can be the fluorescent material, can be above about 0.3 eV.

When the energy level bandgap between the singlet energy levels $S_1^H$ and $S_1^{FD}$ and the triplet energy levels $T_1^H$ and $T_1^{FD}$ of the host and the second dopant are equal to or less than about 0.3 eV, RISC and ISC luminous mechanisms caused by the host and the second dopant can decrease the luminous life span of the OLED 500A. For example, the energy level bandgap between the singlet energy level $S_1^H$ and the triplet energy level $T_1^H$ of the host and/or the energy level bandgap between the singlet energy level $S_1^{FD}$ and the triplet energy level $T_1^{FD}$ of the second dopant can be, but are not limited to, more than about 0.3 eV and equal to or less than about 1.5 eV.

Besides, it is necessary to adjust property Highest Occupied Molecular Orbital (HOMO) energy levels and Lowest Unoccupied Molecular Orbital (LUMO) energy levels of the host and the first dopant, which can be the fluorescent material. For example, it is preferable that an energy level bandgap ($|HOMO^H-HOMO^{TD}|$) between a Highest Occupied Molecular Orbital energy level ($HOMO^H$) of the host and a Highest Occupied Molecular Orbital energy level ($HOMO^{TD}$) of the first dopant, or an energy level bandgap ($|LUMO^H-LUMO^{TD}|$) between a Lowest Unoccupied Molecular Orbital energy level ($LUMO^H$) of the host and a Lowest Unoccupied Molecular Orbital energy level ($LUMO^{TD}$) of the first dopant can be equal to or less than about 0.5 eV, for example, between about 0.1 eV to about 0.5 eV. In this case, the charges can be transported efficiently from the host to the first dopant and thereby enhancing an ultimate luminous efficiency.

In addition, it is necessary to implement OLED that enables transfer energies from the first dopant of the delayed fluorescent material, which has been converted to ICT complex state by RISC, to the second dopant of the fluorescent material in EML 560a, and has high luminous efficiency and color purity. In order to implement such an OLED, each of the excited state singlet energy level $S_1^{TD}$ and the excited state triplet energy level $T_1^{TD}$ of the first dopant must be higher than an excited state singlet energy level $S_1^{FD}$ and an excited state triplet energy level $T_1^{FD}$ of the second dopant, respectively.

Particularly, the energy transfer from the delayed fluorescent material to the fluorescent material is most important to improve the luminous efficiency of an OLED including the finally emitting fluorescent material in implementing the hyper-fluorescence. The most important factor determining the energy transfer efficiency from the delayed fluorescent material to the fluorescent material is an overlapping area between the emission wavelength ranges of the delayed fluorescent material and the absorption wavelength ranges of the fluorescent material to which exciton energy is transferred.

Blue emitting delayed fluorescent material can have a typical wavelength of Maximum Photoluminescence (PL $\lambda_{max}$) of about 470 nm, at least about 450 nm.

Accordingly, blue emitting fluorescent material must have Wavelength of Maximum absorption (Abs. $\lambda_{max}$) of at least 440 nm so that it can receive the exciton energy efficiently from the blue emitting delayed fluorescent material. In addition, the ultimately emitting fluorescent material in the hyper-fluorescence mechanism must have PL $\lambda_{max}$ of about 460 nm so as to implement deep blue luminescence.

Figure 8:
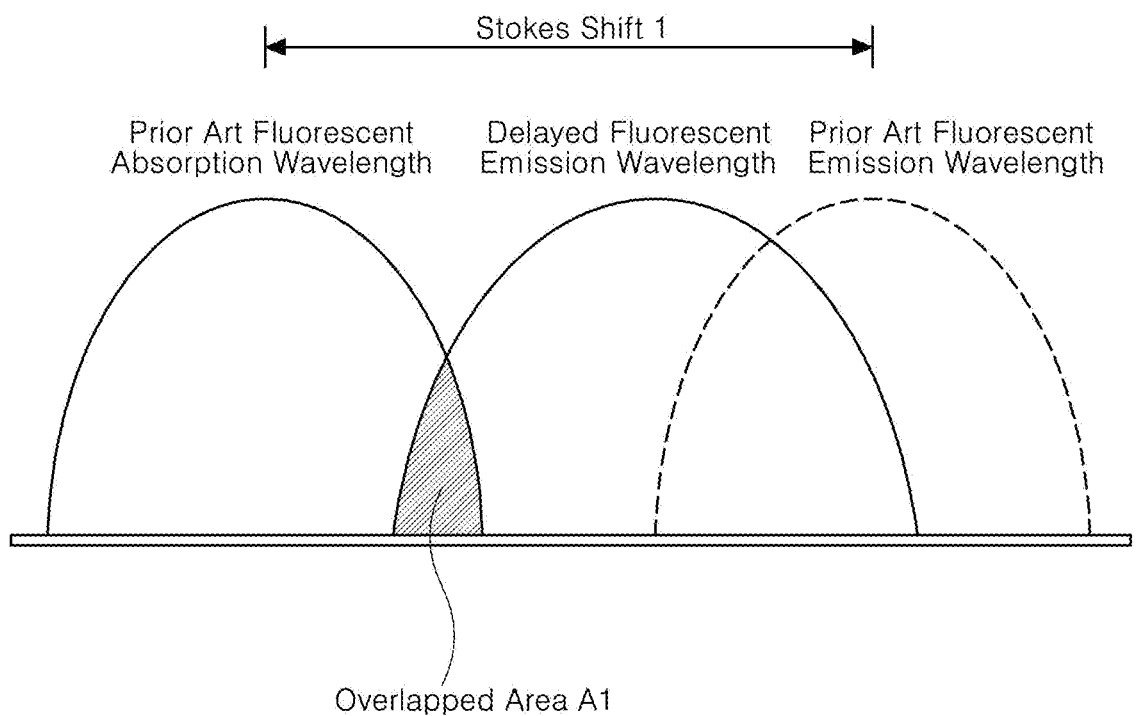
FIG. 8 is a schematic diagram illustrating relationships among absorption and emission wavelengths when an exciton energy is transferred from the delayed fluorescent material to the fluorescent material in accordance with the prior art.

However, as illustrated in FIG. 8, which is a schematic diagram illustrating the relationships among absorption and emission wavelengths in case an exciton energy is transferred from the delayed fluorescent material to a prior art fluorescent material, the prior art blue fluorescent material can have PL $\lambda_{max}$ (Emission peak) of about 460 nm, while it has short Abs. $\lambda_{max}$ (Absorption peak) less than 435 nm. In other words, the prior art blue fluorescent material has very broad Stokes Shift "Stokes Shift 1", which is defined as a difference between the PL $\lambda_{max}$ and the Abs. $\lambda_{max}$. Since there exists a very small overlapped area "Overlapped Area A1" between the absorption wavelength spectrum range of the prior art fluorescent material and the emission wavelength spectrum range of the delayed fluorescent material, the exciton energy is transferred poorly from the delayed fluorescent material to the prior art fluorescent material.

Figure 9:
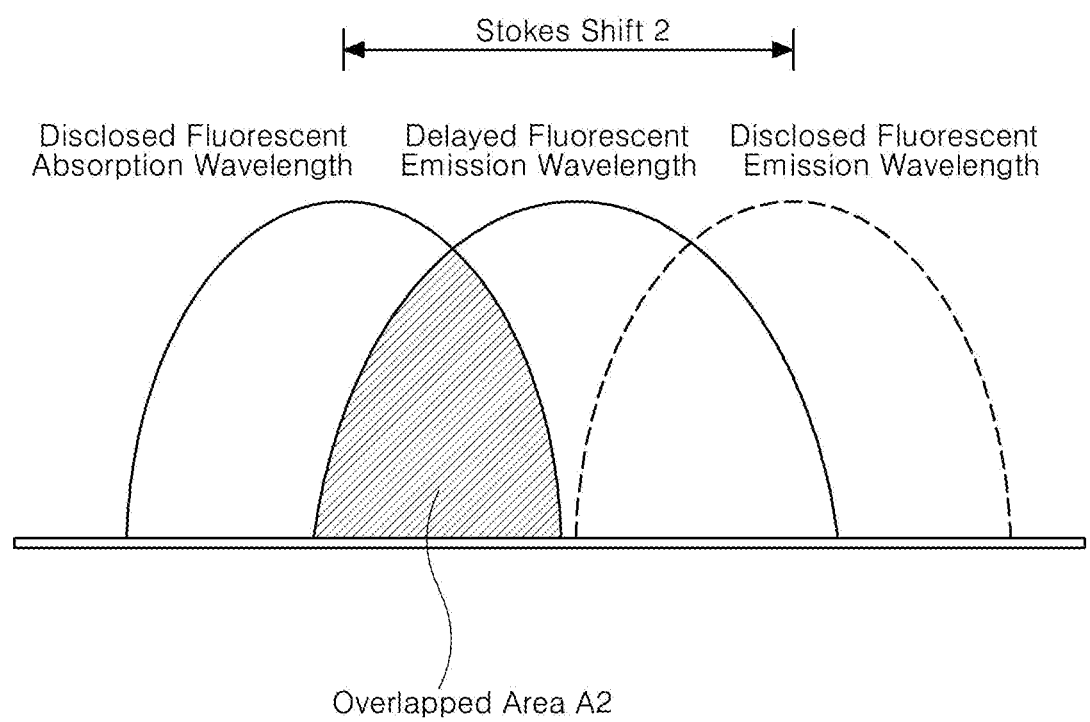
FIG. 9 is a schematic diagram illustrating relationships among absorption and emission wavelengths when an exciton energy is transferred from the delayed fluorescent material to the fluorescent material in accordance with another exemplary embodiment of the present disclosure.

In contrast, as illustrated in FIG. 9, which a schematic diagram illustrating the relationships among absorption and emission wavelengths in case an exciton energy is transferred from the delayed fluorescent material to the fluorescent material in accordance with another exemplary embodiment of the present disclosure, the organic compound having the structure of any one of Chemical Formulae 1 to 3 can have PL $\lambda_{max}$ (emission peak) of similar to the PL $\lambda_{max}$ of the prior art fluorescent material, while the organic compound has Abs. $\lambda_{max}$ (absorption peak) more than or equal to 440 nm, which is relatively longer wavelength range compared to the Abs. $\lambda_{max}$ of the prior art fluorescent material. In other words, the organic compound having the structure of any one of Chemical Formulae 1 to 3 has Stokes Shift "Stokes Shift 2" less than about 20 nm, which is much smaller than the "Stokes Shift 1" of the prior art fluorescent material (Stokes Shift 2<Stokes Shift 1). Accordingly, there exists a very broad or large overlapped area "Overlapped Area A2" between the absorption wavelength spectrum range of the organic compound having the structure of any one of Chemical Formulae 1 to 3 and the emission wavelength spectrum range of the delayed fluorescent material (Overlapped Area A2>Overlapped Area A1). As a result, the exciton energy can be transferred improvingly from the delayed fluorescent material to organic compound as the fluorescent material and can enhance the luminous efficiency of the OLED 500A.

Accordingly, The OLED 500A can realize hyper-fluorescence having excellent luminous efficiency, color purity and luminous life span as well as low power consumption by using the organic compound having the structure of any one of Formulae 1 to 3, which includes a conformationally rigid benzofluorenocarbazole core and aromatic or hetero aromatic groups bonded to specific positions of the benzofluorenocarbazole core, as the fluorescent dopant (in this embodiment, second dopant).

In accordance with the second embodiment, the EML 560a includes the organic compound having the structure of any one of Chemical Formulae 1 to 3 in order to prevent the color purity being lowered in case of using the first dopant as the delayed fluorescent material. The triplet exciton energy of the first dopant, which can be the delayed fluorescent material, is converted to singlet exciton energy of its own by RISC mechanism, then the converted singlet exciton energy of the first dopant can be transferred to the second dopant, which can be the fluorescent material, in the same EML 560a by Dexter energy transfer mechanism, which transfer exciton energies depending upon wave function overlaps among adjacent molecules by inter-molecular electron exchanges and exciton diffusions.

As described above, since the organic compound having the structure of any one of Chemical Formulae 1 to 3 has narrow Stokes Shift, its maximum absorption wavelength shifts toward its PL emission wavelength, i.e. toward longer wavelength ranges. As a result, the spectral overlapping region between the absorption wavelength range of the organic compound and the emission wavelength range of the first dopant, which can be the delayed fluorescent material, increase. As the efficiency of energy transfer from the first dopant to the second dopant (fluorescent dopant), which has the structure of any one of Chemical Formulae 1 to 3, The OLED 500A can enhance its luminous efficiency to realize hyper-fluorescence diode. In addition, since the ultimate emission in the EML 560a occurs when the second dopant, i.e. the organic compound having the structure of any one of Chemical Formulae 1 to 3, which has relatively narrow FWHM compared to the first dopant, is transferred from the excited state to the ground state, the color purity of the OLED 500A can be improved.

In other words, the EML 560a in the OLED 500A of the second embodiment in accordance with the present disclosure includes the organic compound having the structure of any one of Chemical Formulae 1 to 3 as the second dopant. The organic compound has narrow Stokes Shift and narrower FWHM than the delayed fluorescent material. When the EML 560a uses the organic compound having the structure of any one of Chemical Formulae 1 to 3 as the second dopant, the OLED 500A having enhanced luminous efficiency and excellent color purity can be realized.

In one exemplary embodiment, when the EML 560a includes the host, the first dopant and the second dopant, the weight ratio of the host can be larger than the weight ratio of the dopants. The weight ratio of the first dopant can be larger than the weight ratio of the second dopant. As an example, the weight ratio of the host can be larger than the weight ratio of the first dopant and the weight ratio of the first dopant can be larger than the weight ratio of the second dopant.

In this case, enough exciton energy can be transferred from the first dopant to the second dopant in the EML 560 by Dexter transfer mechanism. As an example, when the EML 560a includes the host, the first dopant and the second dopant, each of the dopants can be doped to about 1 to about 50% by weight. For example, the EML 560a can include the first dopant of about 10 to about 50% by weight, and preferably about 10 to about 40% by weight, and the second dopant of about 1 to about 10% by weight.

In one exemplary embodiment, the host in the EML 560a can include, but are not limited to, mCP-CN, CBP, mCBP, mCP, DPEPO, TmPyPB, PYD-2Cz, DCzDBT, DCzTPA, pCzB-2CN, mCzB-2CN, TPSO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin-3-yl)-9H-3,9'-bicarbazole.

The first dopant in the EML 560a can include, but are not limited to, a compound having the delayed fluorescence property and maximum emission wavelength, i.e. PL $\lambda_{max}$ of about 470 nm. As an example, the first dopant in the EML 560a can include, but are not limited to, 10-(4-(4,6-diphenyl-1,3,5-triazin-2-yl)phenyl)-9,9-dimethyl-9,10-dihydroacridine (DMAC-TRZ), 10,10'-(4,4'-sulfonylbis(4,1-phenylene))bis(9,9-dimethyl-9,10-dihydroacridine) (DMAC-DPS), 10-phenyl-10H, 10'H-spiro[acridine-9,9'-anthracen]-10'-one (ACRSA), 3,6-dibenzoyl-4,5-di(1-methyl-9-phenyl-9H-carbazoyl)-2-ethynylbenzonitrile (Cz-VPN), 9,9',9"-(5-(4,6-diphenyl-1,3,5-triazin-2-yl)benzene-1,2,3-triyl)tris(9H-carbazole) (TcZTrz), 9,9'-(5-(4,6-diphenyl-1,3, 5-triazin-2-yl)-1,3-phenylene)bis(9H-carbazole) (DcZTrz), 9,9',9"',9"' '-((6-phenyl-1,3,5-triazin-2,4-diyl)bis(benzene-5, 3,1-triyl))tetrakis(9H-carbazole) (DDczTrz), bis(4-(9H-3,9'-bicarbazol-9-yl)phenyl)methanone (CC2BP), 9'-[4-(4,6-diphenyl-1,3,5-triazin-2-yl)phenyl]-3,3",6,6"-tetraphenyl-9, 3': 6',9"-ter-9H-carbazole (BDPCC-TPTA), 9'-[4-(4,6-diphenyl-1,3,5-triazin-2-yl)phenyl]-9,3',6',9"-ter-9H-carbazole (BCC-TPTA), 9,9'-(4,4'-sulfonylbis(4,1-phenylene))bis(3,6-dimethoxy-9H-carbazole) (DMOC-DPS), 9-(4-(4,6-diphenyl-1,3,5-triazin-2-yl)phenyl)-3',6'- diphenyl-9H-3,9'-bicarbazole (DPCC-TPTA), 10-(4,6-diphenyl-1,3,5-triazin-2-yl)-10H-phenoxazine (Phen-TRZ), 9-(4-(4,6-diphenyl-1,3,5-triazin-2-yl)phenyl)-9H-carbazole (Cab-Ph-TRZ), 1,2,3,5-Tetrakis(3,6-carbazol-9-yl)-4,6-dicyanobenzene (4CzIPN), 2,3,4,6-tetra(9H-carbazol-9-yl)-5-fluorobenzonitrile (4CZFCN), 4,5-di(9H-carbazol-9-yl)phthalonitrile (2CzPN), 10-(4-(4,6-diphenyl-1,3,5-triazin-2-yl)phenyl)-10H-spiro[acridine-9,9'-xanthene], 10-(4-(4,6-diphenyl-1,3,5-triazin-2-yl)phenyl)-10H-spiro[acridine-9,9'-fluorene] (SpiroAC-TRZ) and/or any pyrimidine-based material having the following structure of Chemical Formula 4.

Chemical Formula 4

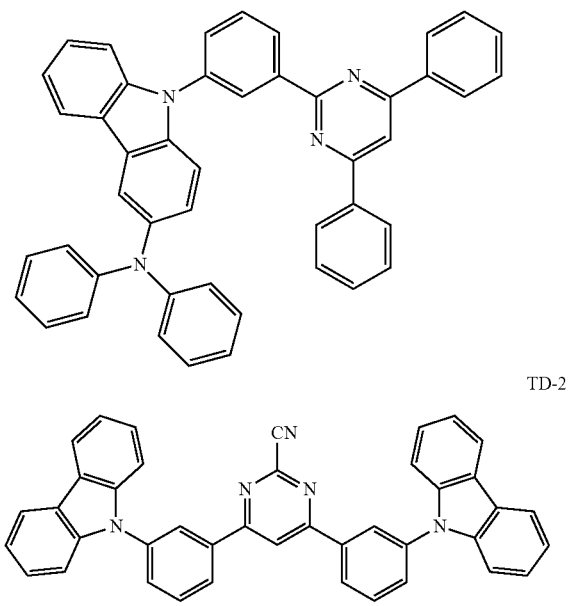

In accordance with the second embodiment, the EML 560a includes the delayed fluorescent material as the first dopant as well as the organic compound having the structure of any one of Chemical Formulae 1 to 3 as the second dopant, so that the OLED 500A can enhance its luminous efficiency and color purity owing to a narrow FWHM by the second dopant and improve its luminous life span.

Figure 10:
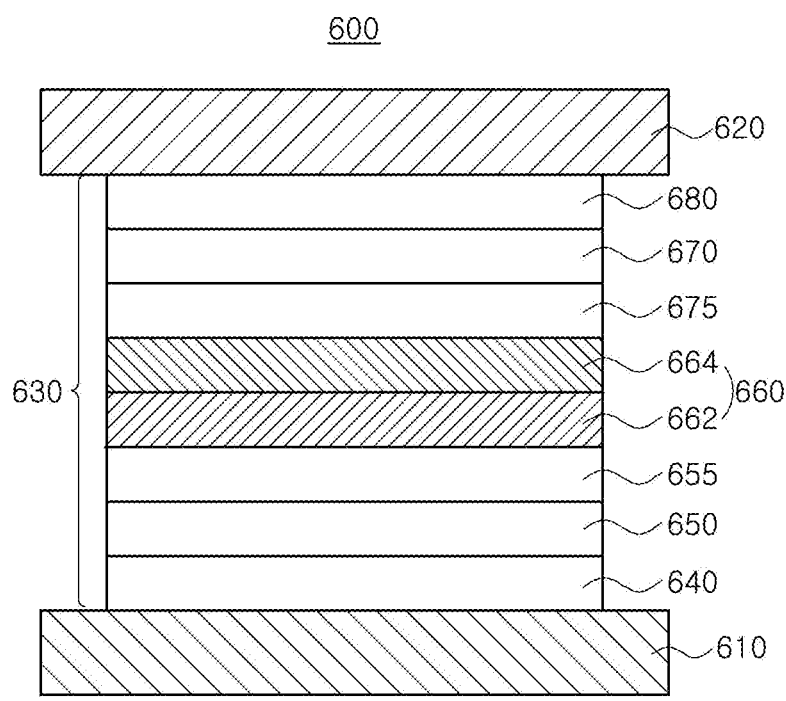
FIG. 10 is a schematic cross-sectional view illustrating an organic light emitting diode in accordance with another exemplary embodiment of the present disclosure.

The OLEDs in accordance with the previous embodiments have a single-layered EML. Alternatively, an OLED in accordance with the present disclosure can include multiple-layered EML. FIG. 10 is a schematic cross-sectional view illustrating an organic light emitting diode having a double-layered EML in accordance with another exemplary embodiment of the present disclosure.

As illustrated in FIG. 10, the OLED 600 in accordance with an exemplary third embodiment of the present disclosure includes first and second electrodes 610 and 620 facing each other and an emitting unit 630 as an emission layer disposed between the first and second electrodes 610 and 620.

In one exemplary embodiment, the emitting unit 630 includes an HIL 640, an HTL 650, and EML 660, an ETL 670 and an EIL 680 each of which is laminated sequentially over the first electrode 610. In addition, the emitting unit 630 can further include an EBL 655 as a first exciton blocking layer disposed between the HTL 650 and the EML 660, and/or an HBL 675 as a second exciton blocking layer disposed between the EML 660 and the ETL 670.

As described above, the first electrode 610 can be an anode and can include, but are not limited to, a conductive material having a relatively large work function values such as ITO, IZO, SnO, ZnO, ICO, AZO, and the likes. The second electrode 620 can be a cathode and can include, but are not limited to, a conductive material having a relatively small work function values such as Al, Mg, Ca, Ag, alloy thereof or combination thereof.

The HIL 640 is disposed between the first electrode 610 and the HTL 650. The HIL 640 can include, but are not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 640 can be omitted in compliance with the structure of the OLED 600.

The HTL 650 is disposed adjacently to the EML 660 between the first electrode 610 and the EML 660. The HTL 650 can include, but are not limited to, aromatic amine compounds such as TPD, NPD(NPB), CBP, poly-TPD, TFB, TAPC, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The EBL 655 can include, but are not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, N,N'-bis[4-(bis(3-methylphenyl)amino)phenyl]-N,N'-diphenyl-[1,1'-biphenyl]-4,4'-diamine (DNTPD), TDAPB and/or 3,6-bis(N-carbazolyl)-N-phenyl-carbazole.

The EML 660 includes a first EML (EML1) 662 and a second EML (EML2) 664. The EML1 662 is disposed between the EBL 655 and the HBL 675 and the EML2 664 is disposed between the EML1 662 and the HBL 675. The configuration and energy levels among the luminous materials in the EML 660 will be explained in more detail below.

The HBL 675 can include, but are not limited to, oxadiazole-based compounds, triazole-based compounds, phenanthroline-based compounds, benzoxazole-based compounds, benzothiazole-based compounds, benzimidazole-based compounds, and triazine-based compounds. As an example, the HBL 675 can include a compound having a relatively low HOMO energy level compared to the emitting material in EML 660. The HBL 675 can include, but are not limited to, BCP, BAlq, Alq$_3$, PBD, spiro-PBD, Liq, B3PYMPM, DPEPO, 9-(6-(9H-carbazol-9-yl)pyridine-3-yl)-9H-3,9'-bicarbazole and combination thereof.

The ETL 670 is disposed between the EML 660 and the EIL 680. In one exemplary embodiment, the ETL 670 can include, but are not limited to, oxadiazole-based compounds, triazole-based compounds, phenanthroline-based compounds, benzoxazole-based compounds, benzothiazole-based compounds, benzimidazole-based compounds, triazine-based compounds, and the likes. As an example, the ETL 670 can include, but are not limited to, Alq$_3$, PBD, spiro-PBD, Liq, TPBi, BAlq, Bphen, NBphen, BCP, TAZ, NTAZ, TpPyPB, TmPPPyTz, PFNBr and/or TPQ.

The EIL 680 is disposed between the second electrode 620 and the ETL 670. In one exemplary embodiment, the EIL 680 can include, but are not limited to, an alkali halide such as LiF, CsF, NaF, BaF$_2$ and the likes, and/or an organic metal compound such as lithium benzoate, sodium stearate, and the likes.

As described above, the EML 660 includes the EML1 662 and the EML2 664. One of the EML1 662 and the EML2

664 includes the organic compound having the structure of any one of Chemical Formulae 1 to 3 as a fluorescent dopant (first fluorescent dopant, F dopant), and the other of the EML1 662 and the EML2 664 includes a delayed fluorescent dopant (T dopant). Hereinafter, the EML 660, where the EML1 662 includes the organic compound as the fluorescent dopant and the EML2 664 includes the delayed fluorescent dopant, will be explained.

In accordance with an exemplary third embodiment, the EML1 662 can include a first host and a fluorescent dopant, i.e. the organic compound having the structure of any one of Chemical Formulae 1 to 3. While the organic compound having the structure of any one of Chemical Formulae 1 to 3 has a narrow FWHM and therefore has an advantage in terms of color purity, its quantum efficiency is limited because its triplet excitons cannot be involved in the emission process.

In contrast, the EML2 664 can include a second host and the delayed fluorescent dopant as the first dopant. The delayed fluorescent dopant in the EML2 664 has little energy level bandgap between the excited state triplet energy level $T_1^{TD}$ and the excited state singlet energy level $S_1^{TD}$, i.e. equal to or less than about 0.3 eV, and its exited state triplet energy can be converted to its excited state singlet energy by RISC mechanism. While the delayed fluorescent dopant has high quantum efficiency, it shows poor color purity due to its wide FWHM.

However, in this exemplary embodiment, the singlet exciton energy and the triplet exciton energy of the delayed fluorescent dopant in EML2 664 can be transferred to the fluorescent dopant in the EML1 662 disposed adjacently to the EML2 664 by FRET (Forster resonance energy transfer) mechanism, which transfers energy non-radially through electrical fields by dipole-dipole interactions. Accordingly, the ultimate emission occurs in the fluorescent dopant within the EML1 662.

Figure 11:
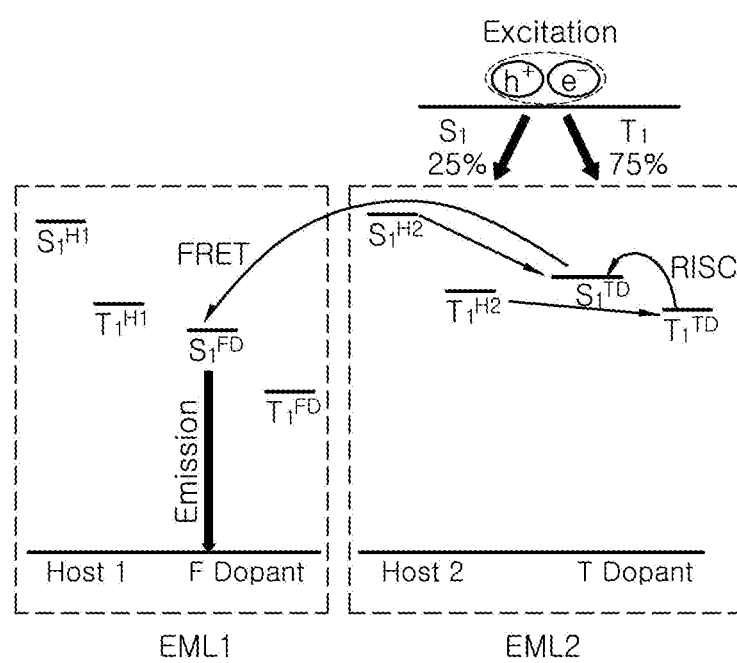
FIG. 11 is a schematic diagram illustrating luminous mechanism by energy level bandgap among luminous materials in accordance with another exemplary embodiment of the present disclosure.

In other words, the triplet exciton energy of the delayed fluorescent dopant is converted to the singlet exciton energy of its own in the EML2 664 by RISC mechanism, then the converted singlet exciton energy of the delayed fluorescent dopant is transferred to the singlet exciton energy of the fluorescent dopant because the excited state singlet energy level $S_1^{TD}$ of the delayed fluorescent dopant is higher than the excited state singlet energy level $S_1^{FD}$ of the fluorescent dopant (See, FIG. 11).

The fluorescent dopant in the EML1 662 can emit light both using the singlet exciton energy and the triplet exciton energy of the delayed fluorescent dopant. Since the fluorescent dopant has relatively narrow FWHM as compared with the delayed fluorescent dopant, the OLED 600 can enhance its luminous efficiency and color purity. In addition, the organic compound as the fluorescent dopant in the EML1 662 has very narrow Stokes Shift (See, FIG. 9) and can emit blue light having high color purity. Therefore, the OLED 600 can realize hyper-fluorescence as exciton energy is efficiently transferred from the delayed fluorescent dopant in the EML2 664 to the fluorescent dopant in the EML1 662.

In this case, the delayed fluorescent dopant only acts as transferring energy to the fluorescent dopant. The EML2 664 including the delayed fluorescent dopant is not involved in the ultimate emission process, while the EML1 662 including the fluorescent dopant emits light.

Each of the EML1 662 and the EML2 664 includes the first host and the second host, respectively. The first host and the second host can be the same or different from each other. For example, each of the first host and the second host can independently include, but are not limited to, mCP-CN, CBP, mCBP, mCP, DPEPO, PPT, TmPyPB, PYD-2CZ, DCzDBT, DCzTPA, pCzB-2CN, mCzB-2CN, TPSO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin-3-yl)-9H-3,9'-bicarbazole, respectively.

In addition, the delayed fluorescent dopant, which can be included in the EML2 664, can include, but are not limited to, DMAC-TRZ, DMAC-DPS, ACRSA, Cz-VPN, TcZTrz, DcZTrz, DDczTrz, CC2BP, BDPCC-TPTA, BCC-TPTA, DMOC-DPS, DPCC-TPTA, Phen-TRZ, Cab-Ph-TRZ, 4CzIPN, 4CZFCN, 2CzPN, 10-(4-(4,6-diphenyl-1,3,5-triazin-2-yl)phenyl)-10H-spiro[acridine-9,9'-xanthene], 10-(4-(4,6-diphenyl-1,3,5-triazin-2-yl)phenyl)-10H-spiro[acridine-9,9'-fluorene] (SpiroAC-TRZ) and/or any pyrimidine-based material having the structure of Chemical Formula 4.

In one exemplary embodiment, each of the first and second hosts can have more weight ratio than the first fluorescent dopant and the delayed fluorescent dopant in the EML1 662 and the EML2 664, respectively. Besides, the weight ratio of the delayed fluorescent dopant in the EML2 664 can be larger than the weight ratio of the fluorescent dopant in the EML1 662. In this case, it is possible to transfer enough energy from the delayed fluorescent dopant in the EML2 664 to the fluorescent dopant in the EML1 662.

As an example, the EML1 662 can include the fluorescent dopant of, but are not limited to, about 1 to about 50% by weight, and preferably about 1 to about 30% by weight. The EML2 664 can include the delayed fluorescent dopant of, but are not limited to, about 10 to about 50% by weight, and preferably about 10 to about 40% by weight.

Energy level relationships among the materials in the double-layered EML 660 will be explained. FIG. 11 is a schematic diagram illustrating luminous mechanism by energy level bandgap among luminous materials in a double-layered EML in accordance with another exemplary embodiment of the present disclosure. As illustrated in FIG. 11, an excited state singlet energy level $S_1^{H1}$ of the first host is higher than an excited state singlet energy level $S_1^{FD}$ of the fluorescent dopant in the EML1 662.

Also, each of an excited state singlet energy level $S_1^{H2}$ and an excited state triplet energy level $T_1^{H2}$ of the second host are higher than each of an excited state singlet energy level $S_1^{TD}$ and an excited state triplet energy level $T_1^{TD}$ of the delayed fluorescent dopant in the EML2 664. Moreover, the excited state singlet energy level $S_1^{TD}$ of the delayed fluorescent dopant in the EML2 664 is higher than the excited state singlet energy level $S_1^{FD}$ of the fluorescent dopant in the EML1 662.

If the EML 660 does not satisfy the above-mentioned energy level conditions, there exists a quenching phenomenon in the delayed fluorescent dopant as well as the fluorescent dopant, so that the exciton energy cannot be transferred to the fluorescent dopant from the delayed fluorescent dopant. As a result, the quantum efficiency of the OLED 600 can be reduced.

In one exemplary embodiment, the energy level bandgap between the excited state singlet energy level $S_1^{TD}$ and the excited state triplet energy level $T_1^{TD}$ can be equal to or less than about 0.3 eV. In addition, an energy level bandgap ($|HOMO^H-HOMO^{TD}|$) between a Highest Occupied Molecular Orbital energy level ($HOMO^H$) of the first and/or second hosts and a Highest Occupied Molecular Orbital energy level ($HOMO^{TD}$) of the delayed fluorescent dopant, or an energy level bandgap ($|LUMO^H-LUMO^{TD}|$) between a Lowest Unoccupied Molecular Orbital energy level (LU- $MO^H$) of the first and/or second hosts and a Lowest Unoccupied Molecular Orbital energy level ($LUMO^{TD}$) of the first dopant can be equal to or less than about 0.5 eV.

In an alternatively exemplary embodiment, the first host, which is included in the EML 662 together with the first fluorescent dopant, i.e. the organic compound having the structure of any one of Chemical Formulae 1 to 3, can be the same material as the EBL 655. In this case, the EML 662 can have an electron blocking function as well as an emission function. In other words, the EML1 662 can act as a buffer layer for blocking electrons. In one embodiment, the EBL 655 can be omitted where the EML1 662 can be an electron blocking layer as well as an emitting material layer.

In another exemplary embodiment, the EML1 662 can include the second host and the delayed fluorescent dopant, while the EML2 664 can include the first host and the fluorescent dopant, i.e. the organic compound having the structure of any one of Chemical Formulae 1 to 3. In this embodiment, the first host in the EML2 664 can be the same material as the HBL 675. In this case, the EML2 664 can have a hole blocking function as well as an emission function. In other words, the EML2 664 can act as a buffer layer for blocking holes. In one embodiment, the HBL 675 can be omitted where the EML2 664 can be a hole blocking layer as well as an emitting material layer.

Figure 12:
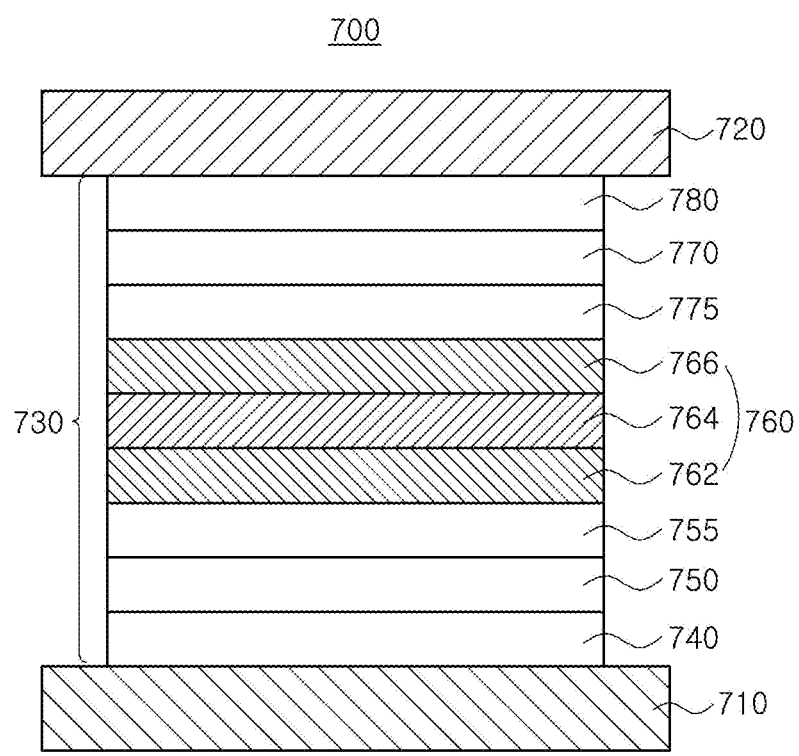
FIG. 12 is a schematic cross-sectional view illustrating an organic light emitting diode in accordance with another exemplary embodiment of the present disclosure.

An OLED having a triple-layered EML will be explained. FIG. 12 is a schematic cross-sectional view illustrating an organic light emitting diode having a triple-layered EML in accordance with another exemplary embodiment of the present disclosure. As illustrated in FIG. 12, an OLED 700 in accordance with forth embodiment of the present disclosure includes first and second electrodes 710 and 720 facing each other and an emitting unit 730 as an emissive unit disposed between the first and second electrodes 710 and 720.

In one exemplary embodiment, the emitting unit 730 includes an HIL 740, an HTL 750, and EML 760, an ETL 770 and an EIL 780 each of which is laminated sequentially over the first electrode 710. In addition, the emitting unit 730 can further include an EBL 755 as a first exciton blocking layer disposed between the HTL 750 and the EML 760, and/or an HBL 775 as a second exciton blocking layer disposed between the EML 760 and the ETL 770.

As described above, the first electrode 710 can be an anode and can include, but are not limited to, a conductive material having a relatively large work function values such as ITO, IZO, SnO, ZnO, ICO, AZO, and the likes. The second electrode 720 can be a cathode and can include, but are not limited to, a conductive material having a relatively small work function values such as Al, Mg, Ca, Ag, alloy thereof or combination thereof.

The HIL 740 is disposed between the first electrode 710 and the HTL 750. The HIL 740 can include, but are not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 740 can be omitted in compliance with the structure of the OLED 700.

The HTL 750 is disposed adjacently to the EML 760 between the first electrode 710 and the EML 760. The HTL 750 can include, but are not limited to, aromatic amine compounds such as TPD, NPD(NPB), CBP, poly-TPD, TFB, TAPC, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The EBL 755 can include, but are not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, N,N'-bis[4-(bis(3-methylphenyl)amino)phenyl]-N,N'-diphenyl-[1,1'-biphenyl]-4,4'-diamine (DNTPD), TDAPB and/or 3,6-bis(N-carbazolyl)-N-phenyl-carbazole.

The EML 760 includes a first EML (EML1) 762, a second EML (EML2) 764 and a third EML (EML3) 766. The configuration and energy levels among the luminous materials in the EML 760 will be explained in more detail below.

The HBL 775 can include, but are not limited to, oxadiazole-based compounds, triazole-based compounds, phenanthroline-based compounds, benzoxazole-based compounds, benzothiazole-based compounds, benzimidazole-based compounds, and triazine-based compounds. As an example, the HBL 775 can include a compound having a relatively low HOMO energy level compared to the emitting material in EML 760. The HBL 775 can include, but are not limited to, BCP, BAlq, $Alq_3$, PBD, spiro-PBD, Liq, B3PYMPM, DPEPO, 9-(6-(9H-carbazol-9-yl)pyridine-3-yl)-9H-3,9'-bicarbazole and combination thereof.

The ETL 770 is disposed between the EML 760 and the EIL 780. In one exemplary embodiment, the ETL 770 can include, but are not limited to, oxadiazole-based compounds, triazole-based compounds, phenanthroline-based compounds, benzoxazole-based compounds, benzothiazole-based compounds, benzimidazole-based compounds, triazine-based compounds, and the likes. As an example, the ETL 770 can include, but are not limited to, $Alq_3$, PBD, spiro-PBD, Liq, TPBi, BAlq, Bphen, NBphen, BCP, TAZ, NTAZ, TpPyPB, TmPPPyTz, PFNBr and/or TPQ.

The EIL 780 is disposed between the second electrode 720 and the ETL 770. In one exemplary embodiment, the EIL 780 can include, but are not limited to, an alkali halide such as LiF, CsF, NaF, $BaF_2$ and the likes, and/or an organic metal compound such as lithium benzoate, sodium stearate, and the likes.

The EML 760 includes the EML1 762 disposed between the EBL 755 and the HBL 775, the EML2 764 disposed between the EML1 762 and the HBL 775 and the EML3 766 disposed between the EML2 764 and the HBL 775. Each of the EML1 762 and the EML3 766 includes a first fluorescent dopant (F dopant 1) and a second fluorescent dopant 2 (F dopant 2), respectively, and the EML2 764 includes a delayed fluorescent dopant. For example, each of the first fluorescent dopant and the second fluorescent dopant can be the organic compound having the structure of any one of Chemical Formulae 1 to 3, respectively. In this case, an excited state singlet energy level $S_1^{TD}$ of the delayed fluorescent dopant in the EML2 764 can be higher than excited state energy levels $S_1^{FD1}$ and $S_1^{FD2}$ of the first and second fluorescent dopants each of which is included in the EML1 762 and EML3 766, respectively (See, FIG. 13). Each of the EML1 762, EML2 764 and EML3 766 further comprise a first host, a second host and a third host, respectively.

In accordance with this embodiment, the singlet energy as well as the triplet energy of the delayed fluorescent dopant in the EML2 764 can be transferred to the first and second fluorescent dopants each of which is included in the EML1 762 and EML3 766 disposed adjacently to the EML2 764 by FRET energy transfer mechanism. Accordingly, the ultimate emission occurs in the first and second fluorescent dopants in the EML1 762 and the EML3 766.

Figure 13:
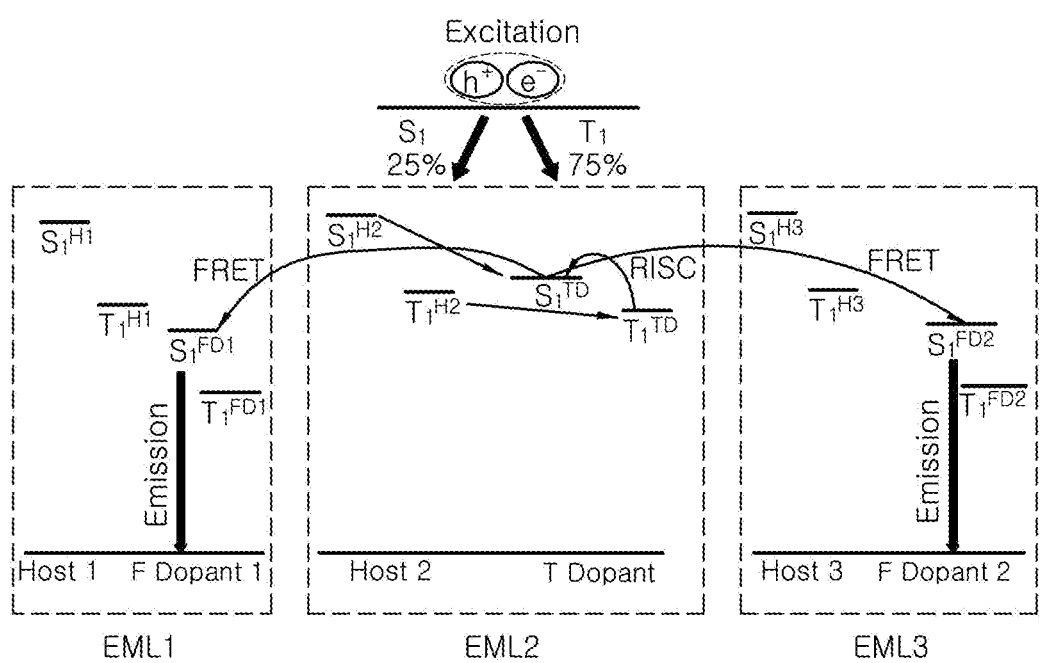
FIG. 13 is a schematic diagram illustrating luminous mechanism by energy level bandgap among luminous materials in accordance with another exemplary embodiment of the present disclosure.

In other words, the triplet exciton energy of the delayed fluorescent dopant is converted to the singlet exciton energy of its own in the EML2 764 by RISC mechanism, then the singlet exciton energy of the delayed fluorescent dopant is transferred to the singlet exciton energy of the first and second fluorescent dopants because the excited state singlet energy level $S_1^{TD}$ of the delayed fluorescent dopant is higher than the excited state singlet energy levels $S_1^{FD1}$ and $S_1^{FD2}$ of the first and second fluorescent dopants (See, FIG. 13). The first and second fluorescent dopants in the EML1 762 and EML3 766 can emit light using the singlet exciton energy and the triplet exciton energy derived from the delayed fluorescent dopant. Therefore, the OLED 700 enhance its luminous efficiency and color purity owing to the narrow FWHM of the first and second fluorescent dopants.

In this case, the delayed fluorescent dopant only acts as transferring energy to the first and second fluorescent dopants. The EML2 764 including the delayed fluorescent dopant is not involved in the ultimate emission process, while both the EML1 762 including the first fluorescent dopant and the EML3 766 including the second fluorescent dopant emit light. Since the fluorescent dopants have relatively narrow FWHM as compared with the delayed fluorescent dopant, the OLED 700 can enhance its luminous efficiency and color purity. In addition, the organic compound as the fluorescent dopants in the EML1 762 and in the EML3 766 has very narrow Stokes Shift (See, FIG. 9) and can emit blue light having high color purity. Therefore, the OLED 700 can realize hyper-fluorescence as exciton energy is efficiently transferred from the delayed fluorescent dopant in the EML2 764 to the fluorescent dopants in the EML1 762 and in the EML3 766.

Each of the EML1 762, the EML2 764 and the EML3 766 includes the first host, the second host and the third host, respectively. For example, each of the first host, the second host and the third host can respectively include, but are not limited to, mCP-CN, CBP, mCBP, mCP, DPEPO, PPT, TmPyPB, PYD-2CZ, DCzDBT, DCzTPA, pCzB-2CN, mCzB-2CN, TPSO1, CCP, 4-(3-(triphenylen-2-yl)phenyl) dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin-3-yl)-9H-3,9'-bicarbazole.

Beside, the delayed fluorescent dopant, which can be included in the EML2 764, can include, but are not limited to, DMAC-TRZ, DMAC-DPS, ACRSA, Cz-VPN, TcZTrz, DcZTrz, DDcZTrz, CC2BP, BDPCC-TPTA, BCC-TPTA, DMOC-DPS, DPCC-TPTA, Phen-TRZ, Cab-Ph-TRZ, 4CzIPN, 4CZFCN, 2CzPN, 10-(4-(4,6-diphenyl-1,3,5-triazin-2-yl)phenyl)-10H-spiro[acridine-9,9'-xanthene], 10-(4-(4,6-diphenyl-1,3,5-triazin-2-yl)phenyl)-10H-spiro[acridine-9,9'-fluorene] (SpiroAC-TRZ) and/or any pyrimidine-based material having the structure of Chemical Formula 4.

In one exemplary embodiment, each of the first to third hosts can have more weight ratio than the first fluorescent dopant, the delayed fluorescent dopant and the second fluorescent dopant in each of the EML1 762, the EML2 764 and the EML3 766, respectively. Besides, the weight ratio of the delayed fluorescent dopant in the EML2 764 can be more than the weight ratio of the first fluorescent dopant in the EML1 762 and of the second fluorescent dopant in the EML3 766. In this case, it is possible to transfer enough exciton energy from the delayed fluorescent dopant in the EML2 764 to the first fluorescent dopant in the EML1 762 and to the second fluorescent dopant in the EML3 766 through FRET energy transfer mechanism.

As an example, each of the EML1 762 and the EML3 766 can include each of the first and second fluorescent dopants of, but are not limited to, about 1 to about 50% by weight, and preferably about 1 to about 30% by weight, respectively.

The EML2 764 can include the delayed fluorescent dopant of, but are not limited to, about 10 to about 50% by weight, and preferably about 10 to about 40% by weight.

Energy level relationships among the luminous materials in the EML 760 will be explained in more detail. FIG. 13 is a schematic diagram illustrating luminous mechanism by energy level bandgap among the luminous material in a triple-layered EML in accordance with another exemplary embodiment of the present disclosure. As illustrated in FIG. 13, an excited state singlet energy level $S_1^{H1}$ of the first host is higher than an excited state singlet energy level $S_1^{FD1}$ of the first fluorescent dopant in the EML1 762. Besides, an excited state singlet energy level $S_1^{H3}$ of the third host is higher than an excited state singlet energy level $S_1^{FD2}$ of the second fluorescent dopant in the EML3 766.

Also, each of an excited state singlet energy level $S_1^{H2}$ and an excited state triplet energy level $T_1^{H2}$ of the second host is higher than each of an excited state singlet energy level $S_1^{TD}$ and an excited state triplet energy level $T_1^{TD}$ of the delayed fluorescent dopant in the EML2 764, respectively. In addition, each of an excited state triplet energy level $T_1^{H1}$ of the first host in the EML1 762 and an excited state triplet energy level $T_1^{H3}$ of the third host in the EML3 766 is higher than the excited state triplet energy level $T_1^{TD}$ of the delayed fluorescent dopant in the EML2 764, respectively. Moreover, the excited state singlet energy level $S_1^{TD}$ of the delayed fluorescent dopant in the EML2 764 is higher than the excited state singlet energy levels $S_1^{FD1}$ and $S_1^{FD2}$ of the first and second fluorescent dopants in the EML1 762 and the EML3 766, respectively.

In one exemplary embodiment, the energy level bandgap between the excited state singlet energy level $S_1^{TD}$ and the excited state triplet energy level $T_1^{TD}$ can be equal to or less than about 0.3 eV. Besides, an energy level bandgap (|HOMO$^H$-HOMO$^{TD}$|) between a Highest Occupied Molecular Orbital energy level (HOMO$^H$) of the first, second and/or third hosts and a Highest Occupied Molecular Orbital energy level (HOMO$^{TD}$) of the delayed fluorescent dopant, or an energy level bandgap (|LUMO$^H$-LUMO$^{TD}$|) between a Lowest Unoccupied Molecular Orbital energy level (LUMO$^H$) of the first, second and/or third hosts and a Lowest Unoccupied Molecular Orbital energy level (LUMO$^{TD}$) of the first dopant can be equal to or less than about 0.5 eV.

In an alternatively exemplary embodiment, the first host, which is included in the EML1 762 together with the first fluorescent dopant, i.e. the organic compound having the structure of any one of Chemical Formulae 1 to 3, can be the same material as the EBL 755. In this case, the EML1 762 can have an electron blocking function as well as an emission function. In other words, the EML1 762 can act as a buffer layer for blocking electrons. In one embodiment, the EBL 755 can be omitted where the EML1 762 can be an electron blocking layer as well as an emitting material layer.

In another exemplary embodiment, the third host, which is included in the EML3 766 together with the second fluorescent dopant, i.e., the organic compound having the structure of any one of Chemical Formulae 1 to 3, can be the same material as the HBL 775. In this case, the EML3 766 can have a hole blocking function as well as an emission function. In other words, the EML3 766 can act as a buffer layer for blocking holes. In one embodiment, the HBL 775 can be omitted where the EML3 766 can be a hole blocking layer as well as an emitting material layer.

In still another exemplary embodiment, the first host in the EML1 762 can be the same material as the EBL 755 and the third host in the EML3 766 can be the same material as the HBL 775. In this embodiment, the EML1 762 can have an electron blocking function as well as an emission function, and the EML3 766 can have a hole blocking function as well as an emission function. In other words, each of the EML1 762 and the EML3 766 can act as a buffer layer for blocking electrons or hole, respectively. In one embodiment, the HBL 755 and the EBL 775 can be omitted where the EML1 762 can be an electron blocking layer as well as an emitting layer and the EML3 766 can be a hole blocking layer as well as an emitting material layer.

Figure 14:
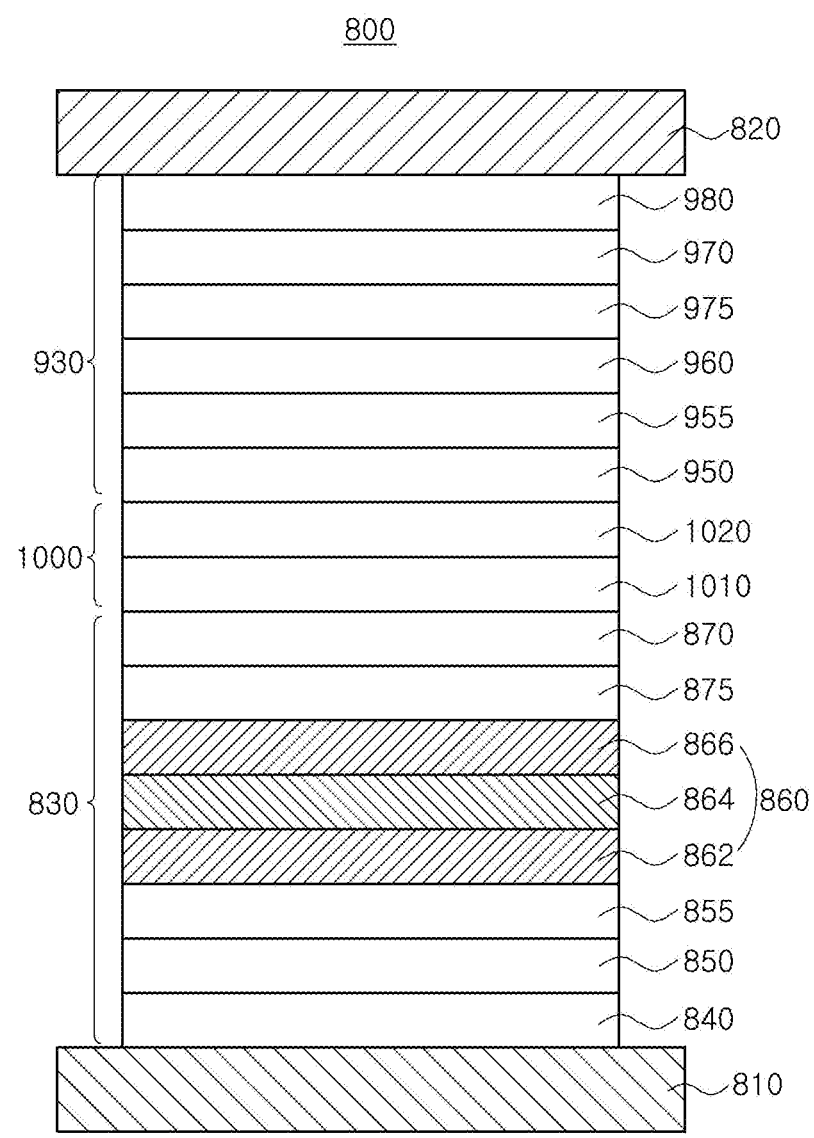
FIG. 14 is a schematic cross-section view illustrating an organic light emitting diode in accordance with another exemplary embodiment of the present disclosure.

In the above embodiments, the OLED having only one emitting unit is described. Unlike the above embodiment, the OLED can have multiple emitting units so as to form a tandem structure. FIG. 14 is a cross-sectional view illustrating an organic light emitting diode in accordance with still another embodiment of the present disclosure.

As illustrated in FIG. 14, the OLED 800 in accordance with the fourth embodiment of the present disclosure includes first and second electrodes 810 and 820 facing each other, a first emitting unit 830 as a first emission layer disposed between the first and second electrodes 810 and 820, a second emitting unit 930 as a second emission layer disposed between the first emitting unit 830 and the second electrode 820, and a charge generation layer 1000 disposed between the first and second emitting units 830 and 930.

As mentioned above, the first electrode 810 can be an anode and include, but are not limited to, a conductive material having a relatively large work function values. As an example, the first electrode 810 can include, but are not limited to, ITO, IZO, SnO, ZnO, ICO, AZO, and the likes. The second electrode 820 can be a cathode and can include, but are not limited to, a conductive material having a relatively small work function values such as Al, Mg, Ca, Ag, alloy thereof or combination thereof.

The first emitting unit 830 includes a HIL 840, a first HTL (a lower HTL) 850, a lower EML 860 and a first ETL (a lower ETL) 870. The first emitting unit 830 can further include a first EBL (a lower EBL) 855 disposed between the first HTL 850 and the lower EML 860 and/or a first HBL (a lower HBL) 875 disposed between the lower EML 860 and the first ETL 870.

The second emitting unit 930 includes a second HTL (an upper HTL) 950, an upper EML 960, a second ETL (an upper ETL) 970 and an EIL 980. The second emitting unit 930 can further include a second EBL (an upper EBL) 955 disposed between the second HTL 950 and the upper EML 960 and/or a second HBL (an upper HBL) 975 disposed between the upper EML 960 and the second ETL 970.

At least one of the lower EML 860 and the upper EML 960 can emit blue (B) light. As an example, both the lower and upper EMLs 860 and 960 can emit blue light. Alternatively, one of the lower and upper EMLs 860 and 960 can emit blue light and the other of the lower and upper EMLs 860 and 960 can emit other any light having emission wavelength ranges longer than the blue light, for example, green (G), yellow-green (YG), yellow (Y) and/or Orange. Hereinafter, the OLED 800, where the lower EML 860 emits blue light and the upper EML 960 emits green, yellow-green, yellow and/or orange light, will be explained.

The HIL 840 is disposed between the first electrode 810 and the first HTL 850 and improves an interface property between the inorganic first electrode 810 and the organic first HTL 850. In one exemplary embodiment, the HIL 840 can include, but are not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 840 can be omitted in compliance with a structure of the OLED 800.

Each of the first and second HTLs 850 and 950 can independently include, but are not limited to, TPD, NPD (NPB), CBP, poly-TPD, TFB, TAPC, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

Each of the first and second ETLs 870 and 970 facilitates electron transportations in the first emitting unit 830 and the second emitting unit 930, respectively. Each of the first and second ETLs 870 and 970 can independently include, but are not limited to, oxadiazole-based compounds, triazole-based compounds, phenanthroline-based compounds, benzoxazole-based compounds, benzothiazole-based compounds, benzimidazole-based compounds, triazine-based compounds, and the likes, respectively. As an example, each of the first and second ETLs 870 and 970 can independently include, but are not limited to, $Alq_3$, PBD, spiro-PBD, Liq, TPBi, BAlq, Bphen, NBphen, BCP, TAZ, NTAZ, TpPyPB, TmPPPyTz, PFNBr and/or TPQ, respectively.

The EIL 980 is disposed between the second electrode 820 and the second ETL 970, and can improve physical properties of the second electrode 820 and therefore, can enhance the life span of the OLED 800. In one exemplary embodiment, the EIL 980 can include, but are not limited to, an alkali halide such as LiF, CsF, NaF, $BaF_2$ and the likes, and/or an organic metal compound such as lithium benzoate, sodium stearate, and the likes.

Each of the first and second EBLs 855 and 955 can independently include, but are not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, N,N'-bis[4-(bis(3-methylphenyl)amino)phenyl]-N,N'-diphenyl-[1,1'-biphenyl]-4,4'-diamine (DNTPD), TDAPB and/or 3,6-bis(N-carbazolyl)-N-phenyl-carbazole, respectively.

Each of the first and second HBLs 875 and 975 can independently include, but are not limited to, oxadiazole-based compounds, triazole-based compounds, phenanthroline-based compounds, benzoxazole-based compounds, benzothiazole-based compounds, benzimidazole-based compounds, and triazine-based compounds. As an example, each of the first and second HBLs 875 and 975 can independently include, but are not limited to, BCP, BAlq, $Alq_3$, PBD, spiro-PBD, Liq, B3PYMPM, DPEPO, 9-(6-(9H-carbazol-9-yl)pyridine-3-yl)-9H-3,9'-bicarbazole and combination thereof, respectively.

In one exemplary embodiment, when the upper EML 960 emits green light, the upper EML 960 can be, but are not limited to, a phosphorescent emitting material layer that includes a host (e.g. CBP and the likes) and an iridium-based dopant (e.g. Iridium (III) bis(2,4-diphenyloxazolato-1,3-N, C2') (acetyl acetonate) ($dpo_2Ir(acac)$), Iridium (III) bis(2-phenyl-oxazolinato-N,C2')(acetyl acetonate) ($op_2Ir(acac)$) and the likes). Alternatively, the upper EML 960 can be a fluorescent material including Alq as a dopant. In this case, the upper EML 960 can emit green light having, but are not limited to, emission wavelength ranges of about 510 nm to about 570 nm.

In another exemplary embodiment, when the upper EML 960 emits yellow light, the upper EML 960 can have a single-layered structure of yellow-green EML or a double-layered structure of a yellow-green EML and green EML. As an example, when the upper EML 960 is a yellow-green EML, the upper EML 960 can include, but are not limited to, a host selected from at least one of CBP and BAlq and a phosphorescent dopant emitting green light. In this case, the upper EML 960 can emit green light having, but are not limited to, emission wavelength ranges of about 510 nm to about 590 nm.

In still another exemplary embodiment, the upper EML 960 can two EMLs, for example, a yellow-green EML and a red EML. As an example, when the upper EML 960 is a yellow-green EML, the upper EML 960 can have a single-layered structure of yellow-green EML or a double-layered structure of a yellow-green EML and green EML. When the upper EML 960 has a single-layered structure of the yellow-green EML, the upper EML 960 can include, but are not limited to, a host selected from at least one of CBP and BAlq and a phosphorescent dopant emitting yellow-green light.

The charge generation layer (CGL) 1000 is disposed between the first emitting unit 830 and the second emitting unit 930. The CGL 1000 include an N-type CGL 1010 disposed adjacently to the first emitting unit 830 and a P-type CGL 1020 disposed adjacently to the second emitting unit 930. The N-type CGL 1010 injects electrons into the first emitting unit 830 and the P-type CGL 1020 injects holes into the second emitting unit 930.

As an example, the N-type CGL 1010 can be a layer doped with an alkali metal such as Li, Na, K and/or Cs and/or an alkaline earth metal such as Mg, Sr, Ba and/or Ra. For example, a host used in the N-type CGL 1010 can include, but are not limited to, an organic compound such as Bphen or MTDATA. The alkali metal or the alkaline earth metal can be doped by about 0.01 wt % to about 30 wt %.

The P-type CGL 1020 can include, but are not limited to, an inorganic material selected from the group consisting of tungsten oxide ($WO_x$), molybdenum oxide ($MoO_x$), beryllium oxide ($Be_2O_3$), vanadium oxide ($V_2O_5$) and combination thereof, and/or an organic material selected from the group consisting of NPD, HAT-CN, 2,3,5,6-Tetrafluoro-7,7,8,8-tetracyanoquinodimethane (F4TCNQ), TPD, N,N,N',N'-Tetranaphthalenyl-benzidine (TNB), TCTA, N,N'-dioctyl-3,4,9,10-perylenedicarboximide (PTCDI-C8) and combination thereof.

The lower EML 860 includes a first EML (EML1) 862, a second EML (EML2) 864 and a third EML3 (EML3) 866 each of which is disposed sequentially between the first EBL 855 and the first HBL 875. Each of the EML1 862 and the EML3 866 includes a first fluorescent dopant (F dopant 1) and a second fluorescent dopant 2 (F dopant 2), respectively, and the EML2 864 includes a delayed fluorescent dopant. For example, each of the first fluorescent dopant and the second fluorescent dopant can be the organic compound having the structure of any one of Chemical Formulae 1 to 3, respectively. In this case, an excited state singlet energy level $S_1^{TD}$ of the delayed fluorescent dopant in the EML2 864 can be higher than excited state energy levels $S_1^{FD1}$ and $S_1^{FD2}$ of the first and second fluorescent dopants each of which is included in the EML1 862 and EML3 866, respectively (See, FIG. 13). Each of the EML1 862, EML2 864 and EML3 866 further comprise a first host, a second host and a third host, respectively.

In this case, the singlet exciton energy as well as the triplet exciton energy of the delayed fluorescent dopant in the EML2 864 can be transferred to the first and second fluorescent dopants each of which is included in the EML1 862 and EML3 866 disposed adjacently to the EML2 864 by FRET energy transfer mechanism. Accordingly, the ultimate emission occurs in the first and second fluorescent dopants in the EML1 862 and the EML3 866.

In other words, the triplet exciton energy of the delayed fluorescent dopant is converted to the singlet exciton energy of its own in the EML2 864 by RISC mechanism, then the singlet exciton energy of the delayed fluorescent dopant is transferred to the singlet exciton energy of the first and second fluorescent dopants because the excited state singlet energy level $S_1^{TD}$ of the delayed fluorescent dopant is higher than the excited state singlet energy levels $S_1^{FD1}$ and $S_1^{FD2}$ of the first and second fluorescent dopants (See, FIG. 13). The first and second fluorescent dopants in the EML1 862 and EML3 866 can emit light using the singlet exciton energy and the triplet exciton energy derived from the delayed fluorescent dopant. Since the fluorescent dopants have relatively narrow FWHM as compared with the delayed fluorescent dopant, the OLED 800 can enhance its luminous efficiency and color purity. In addition, the organic compound as the fluorescent dopants in the EML1 862 and in the EML3 866 has very narrow Stokes Shift (See, FIG. 9) and can emit blue light having high color purity. Therefore, the OLED 800 can realize hyper-fluorescence as exciton energy is efficiently transferred from the delayed fluorescent dopant in the EML2 864 to the fluorescent dopants in the EML1 862 and in the EML3 866.

Each of the EML1 862, the EML2 864 and the EML3 866 includes the first host, the second host and the third host, respectively. For example, each of the first host, the second host and the third host can respectively include, but are not limited to, mCP-CN, CBP, mCBP, mCP, DPEPO, PPT, TmPyPB, PYD-2CZ, DCzDBT, DCzTPA, pCzB-2CN, mCzB-2CN, TPSO1, CCP, 4-(3-(triphenylen-2-yl)phenyl) dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin-3-yl)-9H-3,9'-bicarbazole.

Beside, the delayed fluorescent dopant, which can be included in the EML2 864, can include, but are not limited to, DMAC-TRZ, DMAC-DPS, ACRSA, Cz-VPN, TcZTrz, DcZTrz, DDcZTrz, CC2BP, BDPCC-TPTA, BCC-TPTA, DMOC-DPS, DPCC-TPTA, Phen-TRZ, Cab-Ph-TRZ, 4CzIPN, 4CZFCN, 2CzPN, 10-(4-(4,6-diphenyl-1,3,5-triazin-2-yl)phenyl)-10H-spiro[acridine-9,9'-xanthene], 10-(4-(4,6-diphenyl-1,3,5-triazin-2-yl)phenyl)-10H-spiro[acridine-9,9'-fluorene] (SpiroAC-TRZ) and/or any pyrimidine-based material having the structure of Chemical Formula 4.

In this case, the energy level relationships among the luminous materials, i.e. the first to third hosts, the delayed fluorescent dopant and the first and second fluorescent dopant are identical as illustrated in FIG. 13.

In one exemplary embodiment, each of the first to third hosts can have more weight ratio than the first fluorescent dopant, the delayed fluorescent dopant and the second fluorescent dopant in each of the EML1 862, the EML2 864 and the EML3 866, respectively. Besides, the weight ratio of the delayed fluorescent dopant in the EML2 864 can be more than the weight ratio of the first fluorescent dopant in the EML1 862 and of the second fluorescent dopant in the EML3 866. In this case, it is possible to transfer enough exciton energy from the delayed fluorescent dopant in the EML2 864 to the first fluorescent dopant in the EML1 862 and to the second fluorescent dopant in the EML3 866 through FRET energy transfer mechanism.

In an alternatively exemplary embodiment, the first host, which is included in the EML1 862 together with the first fluorescent dopant, i.e. the organic compound having the structure of any one of Chemical Formulae 1 to 3, can be the same material as the first EBL 855. In this case, the EML1 862 can have an electron blocking function as well as an emission function. In other words, the EML1 862 can act as a buffer layer for blocking electrons. In one embodiment, the first EBL 855 can be omitted where the EML1 862 can be an electron blocking layer as well as an emitting material layer.

In another exemplary embodiment, the third host, which is included in the EML3 866 together with the second fluorescent dopant, i.e., the organic compound having the structure of any one of Chemical Formulae 1 to 3, can be the same material as the first HBL 875. In this case, the EML3 866 can have a hole blocking function as well as an emission function. In other words, the EML3 866 can act as a buffer layer for blocking holes. In one embodiment, the first HBL 875 can be omitted where the EML3 866 can be a hole blocking layer as well as an emitting material layer.

In still another exemplary embodiment, the first host in the EML1 862 can be the same material as the first EBL 855 and the third host in the EML3 866 can be the same material as the first HBL 875. In this embodiment, the EML1 862 can have an electron blocking function as well as an emission function, and the EML3 866 can have a hole blocking function as well as an emission function. In other words, each of the EML1 862 and the EML3 866 can act as a buffer layer for blocking electrons or hole, respectively. In one embodiment, the first HBL 855 and the first EBL 875 can be omitted where the EML1 862 can be an electron blocking layer as well as an emitting layer and the EML3 866 can be a hole blocking layer as well as an emitting material layer.

In an alternative embodiment, the lower EML 860 can have a single-layered structure as illustrated in FIG. 3. In this case, the lower EML 860 can include a host and a fluorescent dopant, which can the organic compound having the structure of any one of Chemical Formulae 1 to 3. Alternatively, the lower EML 860 can include a host, a first dopant, which can be the delayed fluorescent material, and a second dopant, which is the organic compound having the structure of any one of Chemical Formulae 1 to 3.

In another alternative embodiment, the lower EML 860 can have a double-layered structure as illustrated in FIG. 10. In this case, the lower EML 860 can include a first EML and a second EML. The first EML can include a first host and a fluorescent dopant, which is the organic compound having the structure of any one of Chemical Formulae 1 to 3, and the second EML can include a second host and a delayed fluorescent dopant.

In another exemplary embodiment, an OLED of the present disclosure can further includes a third emitting unit disposed between the second emitting unit 930 and the second electrode 820 and a second CGL disposed between the second emitting unit 930 and the third emitting unit. In this case, at least one of the first emitting unit 830, the second emitting unit 930 and the third emitting unit can include the organic compound having the structure of any one of Chemical Formulae 1 to 3 as the dopant.

Synthesis Example 1: Synthesis of Compound 5

(1) Synthesis of Intermediate 5A [2-(7,12-diphenyl-benzo[k]fluoranthen-3-yl)-4,4,5,5-tetramethyl-1,3,2-dioxaborolane]

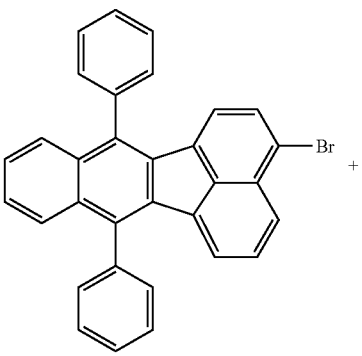

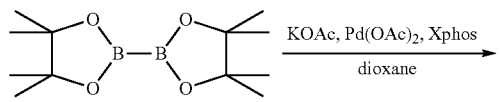

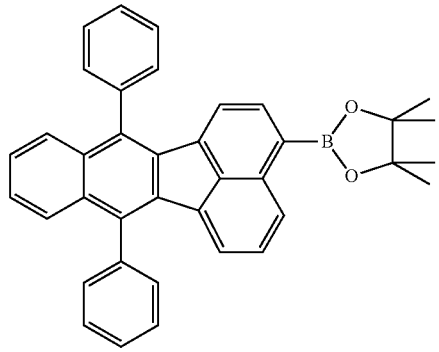

5A 30.0 g (62.1 mmol) of 3-bromo-7,12-diphenylbenzeno[k] fluoranthene, 31.5 g (124.1 mmol) of bis(pinacolato)diboron, 18.3 g (186.2 mmol) of potassium acetate (KOAc), 0.56 g (2.5 mmol) of palladium (II)acetate (Pd(OAc)$_2$), 4.7 g (10.0 mmol) of 2-Dicyclohexylphosphino-2',4',6'-triisopropylphenyl) (Xphos) and 500 mL of dioxane were placed into 1000 mL round bottom flask, then the solution was purged with nitrogen gas and stirred 12 hours at 110° C. After reaction was completed, an organic layer was extracted with dichloromethane and distilled water and the solvent was removed under vacuum distillation. The crude extract was purified by performing a column chromatography using hexane and dichloromethane as a developing solvent to give 24.3 g of intermediate 5A (yield: 74%).

(2) Synthesis of Intermediate 5B [3-(2-nitrophenyl)-7,12-diphenylbenzo[k]fluoranthene]

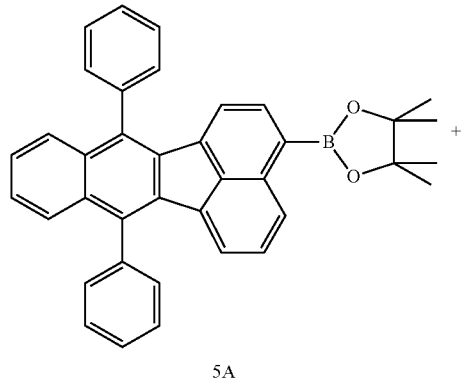

5A

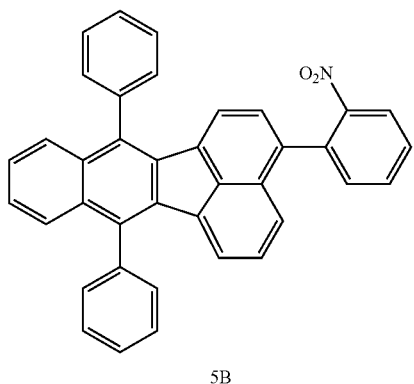

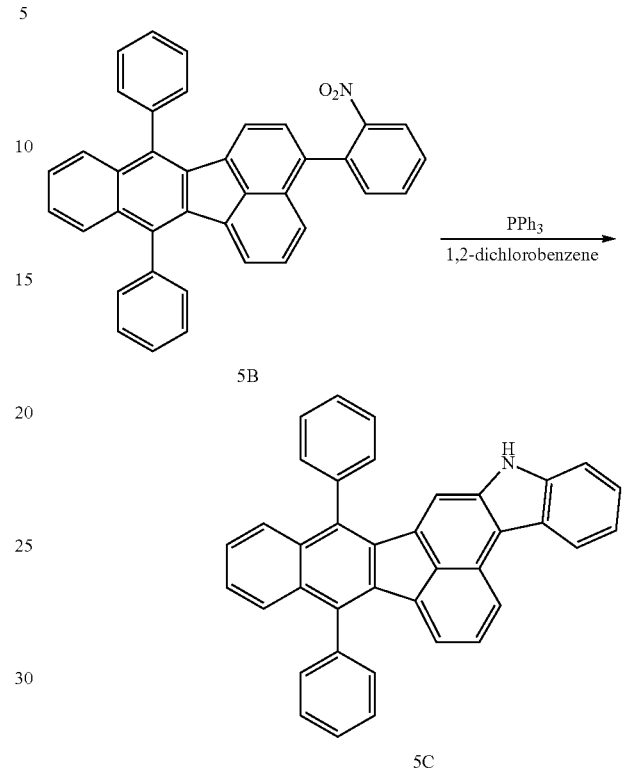

22.0 g (41.5 mmol) of intermediate 5A, 9.2 g (45.6 mmol) of 1-bromo-2-nitrobenzene, 14.3 g (103.7 mmol) of potassium carbonate, 2.4 g (2.1 mmol) of Tetrakis(triphenylphosphine) palladium (Pd(PPh$_3$)$_4$), 300 mL of toluene and 100 mL of ethanol were placed into 1000 mL round bottom flask, then the solution was purged with nitrogen gas and stirred for 10 hours at 100° C. After reaction was completed, an organic layer was extracted with dichloromethane and water and the solvent was removed under vacuum distillation. The crude extract was purified by performing column chromatography using hexane and dichloromethane as a developing solvent to give 19.8 g of intermediate 5B (yield: 91%).

(3) Synthesis of Intermediate 5C [10,15-diphenyl-8H-benzo[6,7]fluoreno[9,1-bc]carbazole]

19.0 g (36.2 mmol) of intermediate 5B, 23.7 g (90.4 mmol) of triphenylphosphine and 200 mL of 1,2-dichlorobenzene were placed into 500 mL round bottom flask, then the solution was purged with nitrogen gas and stirred for 12 hours at 170° C. After reaction was completed, an organic layer was extracted with dichloromethane and distilled water and the solvent was removed under vacuum distillation. The crude extract was purified by performing column chromatography using hexane and dichloromethane as a developing solvent to give 13.5 g of intermediate 5C (yield: 76%).

(4) Synthesis of Intermediate 5D [8,10,15-triphenyl-8H-benzo[6,7]fluoreno[9,1-bc]carbazole]

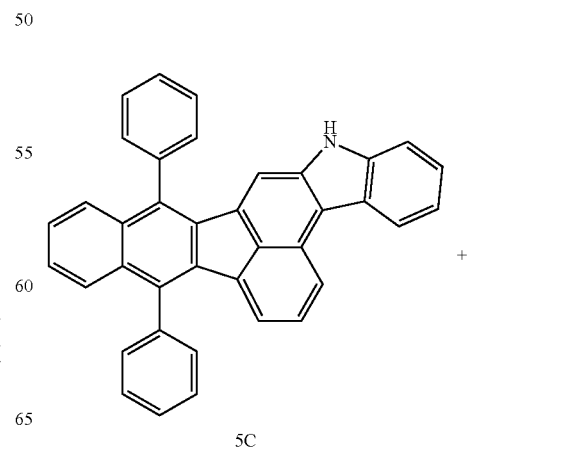

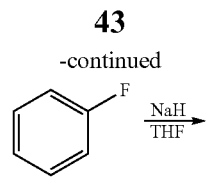

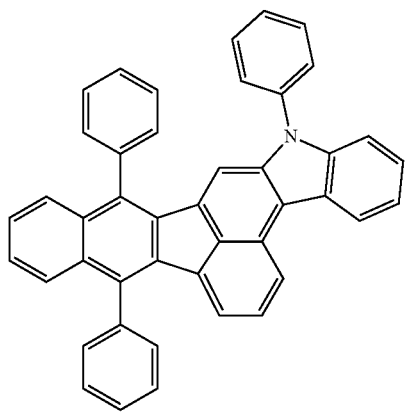

5D 13.0 g (26.3 mmol) of intermediate 5C and 300 mL of tetrahydrofuran (THF) were placed into 500 mL round bottom flask, and the solution was purged with nitrogen gas. Then, 2.1 g (52.7 mmol; 60 wt % dissolved in paraffin) of sodium hydride was added into the solution and the solution was stirred for 30 mins at room temperature. Fluorobenzene (3.8 g, 39.5 mmol) was added therein, and the mixed solution was stirred for 24 hours at room temperature. After reaction was completed, an organic layer was extracted with dichloromethane and distilled water and the solvent was removed under vacuum distillation. The crude extract was purified by performing column chromatography using hexane and dichloromethane as a developing solvent to give 12.2 g of intermediated 5D (yield: 81%).

(5) Synthesis of Intermediate 5E [5-bromo-8,10,15-triphenyl-8H-benzo[6,7]fluoreno[9,1-bc]carbazole]

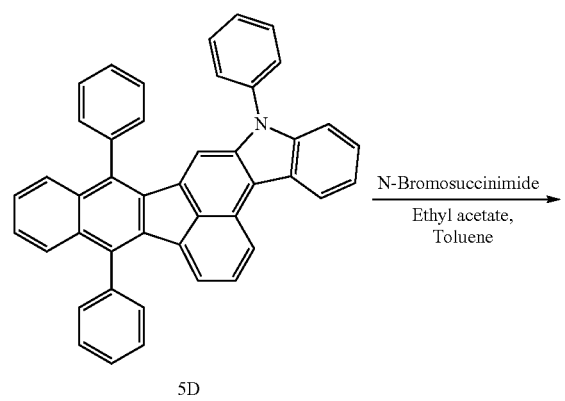

5D

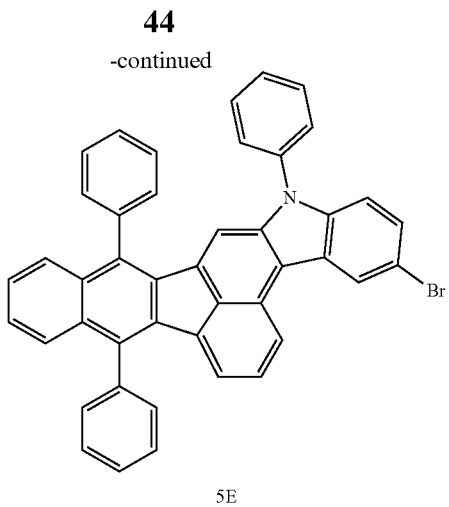

5E 12.0 g (21.1 mmol) of intermediate 5D, 3.8 g (21.1 mmol) of N-bromosuccinimide, 200 mL of toluene and 100 mL of ethyl acetate were placed into 500 mL round bottom flask, then the solution was purged with nitrogen gas and stirred for 24 hours at room temperature. After reaction was completed, an organic layer was extracted with dichloromethane and distilled water and the solvent was removed under vacuum distillation. The crude extract was purified by performing column chromatography using hexane and dichloromethane as a developing solvent to give 12.2 g of intermediate 5E (yield: 89%).

(6) Synthesis of Compound 5

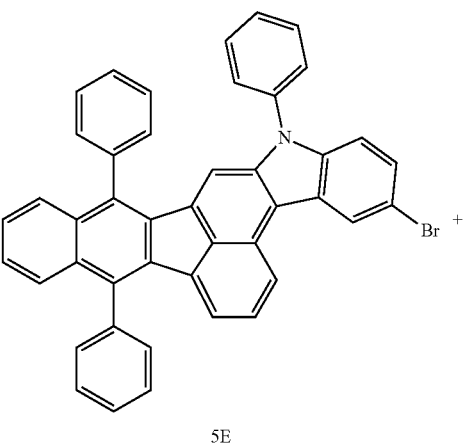

5E

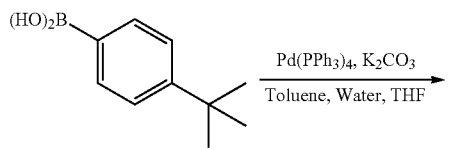

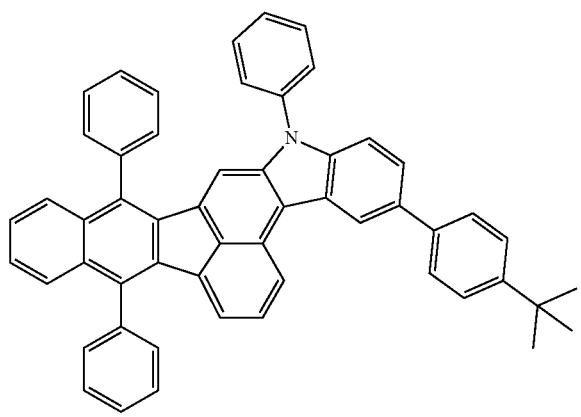

Compound 5

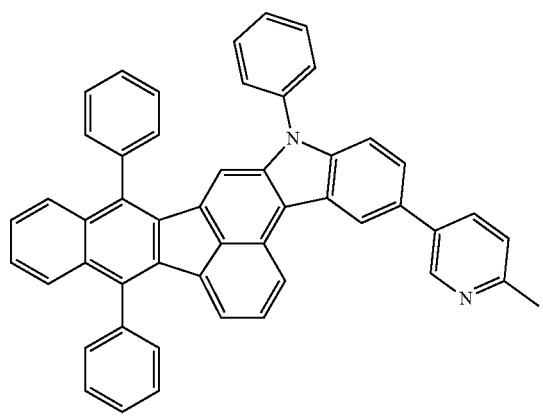

Compound 7

2.0 g (3.1 mmol) of intermediate 5E, 0.6 g (3.4 mmol) of (4-(tert-butyl)phenyl)-boronic acid, 1.7 g (12.3 mmol) of potassium carbonate, 0.36 g (0.31 mmol) of Pd(PPh$_3$)$_4$, 100 mL of toluene, 20 mL of water and 10 mL of THF were placed into 500 mL round bottom flask, then the solution was purged with nitrogen gas and stirred for 12 hours at 100° C. After reaction was completed, an organic layer was extracted with dichloromethane and distilled water and the solvent was removed under vacuum distillation. The crude extract was purified by performing column chromatography using hexane and dichloromethane as a developing solvent to give 1.7 g of Compound 5 (yield: 78%).

Synthesis Example 2: Synthesis of Compound 7 [5-(6-methylpyridin-3-yl)-8,10,15-triphenyl-8H-benzo[6,7]fluoreno[9,1-bc]carbazole]

2.0 g (3.1 mmol) of intermediate 5E, 0.46 g (3.4 mmol) of (6-methylpyridin-3-yl)-boronic acid, 1.7 g (12.3 mmol) of potassium carbonate, 0.36 g (0.31 mmol) of Pd(PPh$_3$)$_4$, 100 mL of toluene, 20 mL of water and 10 mL of THF were placed into 500 mL round bottom flask, then the solution was purged with nitrogen gas and stirred for 12 hours at 100° C. After reaction was completed, an organic layer was extracted with dichloromethane and distilled water and the solvent was removed under vacuum distillation. The crude extract was purified by performing column chromatography using hexane and dichloromethane as a developing solvent to give 1.4 g of Compound 7 (yield: 69%).

Synthesis Example 3: Synthesis of Compound 12 [5-(naphthalen-2-yl)-8,10,15-triphenyl-8H-benzo[6,7]fluoreno[9,1-bc]carbazole]

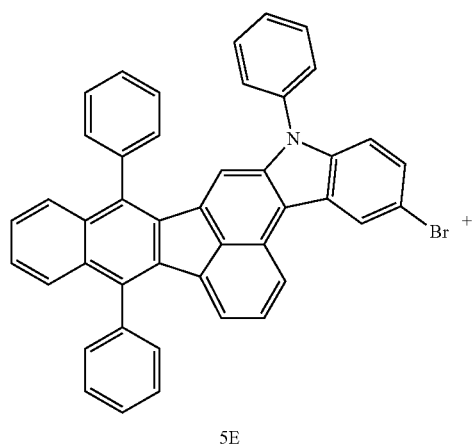

5E

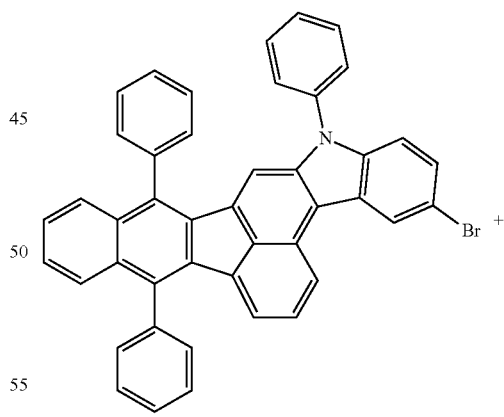

5E

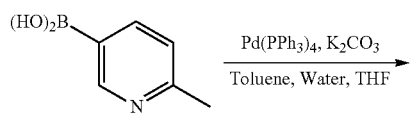

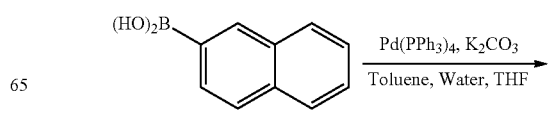

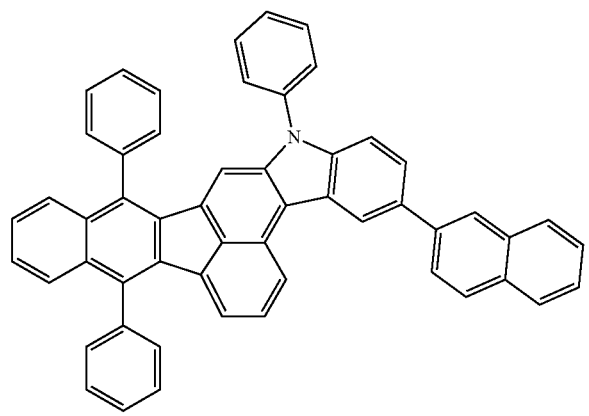

Compound 12

2.0 g (3.1 mmol) of intermediate 5E, 0.58 g (3.4 mmol) of naphthlen-2-yl-bornic acid, 1.7 g (12.3 mmol) of potassium carbonate, 0.36 g (0.31 mmol) of Pd(PPh$_3$)$_4$, 100 mL of toluene, 20 mL of water and 10 mL of THF were placed into 500 mL round bottom flask, then the solution was purged with nitrogen gas and stirred for 12 hours at 100° C. After reaction was completed, an organic layer was extracted with dichloromethane and distilled water and the solvent was removed under vacuum distillation. The crude extract was purified by performing column chromatography using hexane and dichloromethane as a developing solvent to give 1.6 g of Compound 12 (yield: 75%).

Synthesis Example 4: Synthesis of Compound 16 [5-(9,10-diphenylanthracen-2-yl)-8,10,15-triphenyl-8H-benzo[6,7]fluoreno[9,1-bc]carbazole]

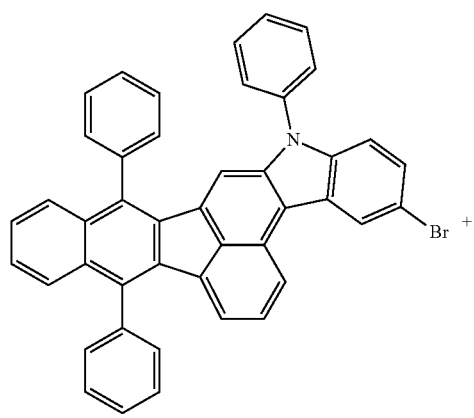

5E

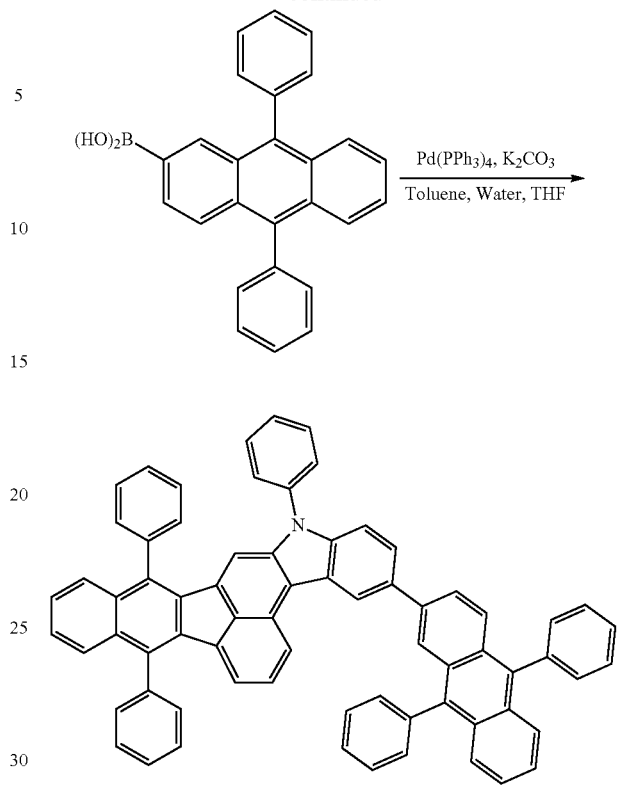

Compound 16

2.0 g (3.1 mmol) of intermediate 5E, 1.3 g (3.4 mmol) of (9,10-diphenylanthracen-2-yl)-boronic acid, 1.7 g (12.3 mmol) of potassium carbonate, 0.36 g (0.31 mmol) of Pd(PPh$_3$)$_4$, 100 mL of toluene, 20 mL of water and 10 mL of THF were placed into 500 mL round bottom flask, then the solution was purged with nitrogen gas and stirred for 12 hours at 100° C. After reaction was completed, an organic layer was extracted with dichloromethane and distilled water and the solvent was removed under vacuum distillation. The crude extract was purified by performing column chromatography using hexane and dichloromethane as a developing solvent to give 2.1 g of Compound 16 (yield: 76%).

Experimental Example 1: Measurement of Luminescence Properties of Organic Compound UV Wavelength of Maximum absorption (UV $\lambda_{max}$), wavelength of Maximum Photoluminescence (PL $\lambda_{max}$), Stokes Shift, FWHM (full width at half maximum) and HOMO energy level for the Compounds 5, 7, 12 and 16, each of which were respectively in the Synthesis Examples 1 to 4, were measured so as to evaluate luminescence properties of those compounds. Also, UV $\lambda_{max}$, PL $\lambda_{max}$, Stokes Shift, FWHM and HOMO energy level for the following compounds, each of which includes a benzofluoranthene core (Ref. 1) and a pyrene core (Ref 2), were measured for comparison. In addition, PL $\lambda_{max}$ and FWHM were measured for thin films each of which includes 9-(6-(9H-carbazol-9-yl)pyridin-3-yl)-9H-3,9'-bicarbazole as a host by 70 wt % doped with TD-1 or TD-2, having the structure in Chemical Formula 4, as a dopant by 30 wt %.

Reference Compound

Reference 1

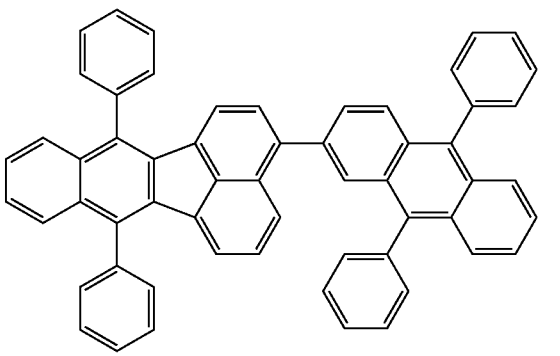

Reference 2

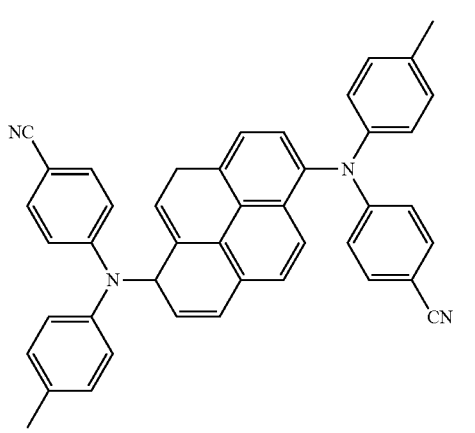

The measurement results are indicated in the following Table 1. As indicated by Table 1, both Ref. 1 having the benzofluoranthene core and Ref. 2 having the pyrene core have similar PL $\lambda_{max}$ ranges as the Compounds 5, 7, 12 and 16. However, it was confirmed that each of Ref 1 and Ref. 2 has a very a broad Stokes shift, so that their UV $\lambda_{max}$ were shifted to an extremely short wavelength ranges as compared with the PL $\lambda_{max}$ of the TD-1 and TD-2, each of which is a delayed fluorescent material. Accordingly, it can be seen that the overlapping area between the absorption wavelengths of the Ref 1 and Ref 2 and the emission wavelengths of the delayed fluorescent materials is very small.

On the contrary, each of Compounds 5, 7, 12 and 16 exhibited a narrow Stokes shift as its UV $\lambda_{max}$ is located adjacently to its PL UV $\lambda_{max}$ as compared with Ref. 1 and Ref 2. Therefore, it can be seen that the overlapping area between the absorption wavelengths of those compounds and the emission wavelengths of the delayed fluorescent materials, i.e. TD-1 and TD-2 are greatly increased and each of Compound 5, 7, 12 and 16 are suitable for realizing blue light emission having excellent color purity.

TABLE 1

| Luminescence Properties of Organic Compound | | | | | |
|---|---|---|---|---|---|
| Sample | UV $\lambda_{max}$ (nm) | PL $\lambda_{max}$ (nm) | Stokes shift (nm) | FWHM (nm) | HOMO (eV) |
| Compound 5 | 440 | 455 | 15 | 56 | −5.31 |
| Compound 7 | 440 | 454 | 14 | 57 | −5.38 |
| Compound 12 | 441 | 455 | 14 | 55 | −5.29 |
| Compound 16 | 444 | 460 | 16 | 58 | −5.33 |
| Ref. 1 | 424 | 455 | 31 | 61 | −5.09 |
| Ref. 2 | 411 | 457 | 46 | 52 | −5.28 |
| TD-1 | — | 470 | — | 69 | — |
| TD-2 | — | 468 | — | 70 | — |

Example 1: Fabrication of Organic Light Emitting Diode (OLED)

An organic light emitting diode was fabricated using Compound 5 synthesized in the Synthesis Example 1 as a dopant in an emitting material layer (EML). A glass substrate was washed by UV-Ozone treatment before using, and was transferred to a vacuum chamber for depositing emissive layer. Subsequently, an anode, an emissive layer and a cathode were deposited by evaporation from a heating boat under $10^{-6}$ Torr vacuum condition as the following order: An anode (ITO; 500 Å); a hole injection layer (HIL) (HAT-CN; 50 Å); a hole transport layer (HTL) (NPB; 500 Å); an electron blocking layer (EBL) (3,6-Bis(N-carbazolyl)-N-phenyl-carbazole; 100 Å); an emitting material layer (EML) (9-(6-(9H-carbazol-9-yl)pyridin-3-yl)-9H-3,9'-bicarbazole (host): TD-1 (delayed fluorescent material): Compound 5 (fluorescent material)=70:29:1 by weigh ratio); 250 Å); a hole blocking layer (HBL) (9-(6-(9H-carbazol-9-yl)pyridin-3-yl)-9H-3,9'-bicarbazole; 100 Å); an electron transport layer (ETL) (TPBi; 250 Å); an electron injection layer (EIL) (LiF; 8 Å); and a cathode (Al; 1000 Å).

And then, cappling layer (CPL) was deposited over the cathode and the device was encapsualted by glass. After deposition of emissve layer and the cathode, the OLED was transferred from the deposition chamber to a dry box for film formation, followed by encapsulation using UV-curable epoxy and moisture getter. The manufacture organic light emitting diode had an emission area of 9 mm².

Examples 2 to 4: Fabrication of OLED

An organic light emitting diode was manufactured as the same process and the same materials as Example 1, except using Compound 7 (Example 2), Compound 12 (Example 3) and Compound 16 (Example 4) as the fluorescent dopant in place of Compound 1 in the EML.

Examples 5 and 6: Manufacture of OLED

An organic light emitting diode was manufactured as the same process and the same materials as Example 1, except using TD-2 as the delayed fluorescent material in place of TD-1 (Example 5), and using TD-2 as the delayed fluorescent material in place of TD-1 and Compound 16 as the fluorescent material in place of Compound 5 (Example 6) in the EML.

Comparative Examples 1 to 3: Manufacture of OLED

An organic light emitting diode was manufactured as the same process and the same materials as in Example 1, except using Ref 1 as the fluorescent material in place of Compound 5 (Comparative Example 1; Ref. 1), using Ref. 2 as the fluorescent material in place of Compound 5 (Comparative Example 2; Ref 2), and using TD-2 as the delayed fluorescent material in place of TD-1 and Ref 1 as the fluorescent material in place of Compound 5 (Comparative Example 3; Ref 3) in the EML.

Experimental Example 2: Measurement of Luminous Properties of OLED

Each of the organic light emitting diode with manufactured by Examples 1 to 6 and Comparative Examples 1 to 3 was connected to an external power source, and luminous properties for all the diodes were evaluated using a constant current source (KEITHLEY) and a photometer PR650 at room temperature. In particular, driving voltage (V), current efficiency (cd/A), power efficiency (lm/W), color coordinates and maximum electroluminescent wavelength (EL $\lambda_{max}$; nm), FWHM, maximum external quantum efficiency ($EQE_{max}$; %) at a current density of 10 mA/cm² of the light emitting diodes of Examples 1 to 6 and Comparative Examples 1 to 3 were measured. The results thereof are shown in the following Table 2.

TABLE 2

Luminous Properties of OLED

| Sample | V | cd/A | lm/W | CIEx | CIEy | EL $\lambda_{max}$ (nm) | FWHM (nm) | $EQE_{max}$ (%) |
|---|---|---|---|---|---|---|---|---|
| Example 1 | 3.9 | 14.0 | 11.3 | 0.148 | 0.171 | 461 | 58 | 11.0 |
| Example 2 | 4.1 | 12.3 | 9.4 | 0.144 | 0.170 | 460 | 59 | 9.8 |
| Example 3 | 4.0 | 12.6 | 9.9 | 0.147 | 0.169 | 460 | 58 | 10.5 |
| Example 4 | 4.0 | 15.9 | 12.5 | 0.150 | 0.175 | 465 | 61 | 13.2 |
| Example 5 | 3.8 | 12.2 | 10.1 | 0.144 | 0.169 | 458 | 57 | 10.8 |
| Example 6 | 4.0 | 16.7 | 13.1 | 0.150 | 0.176 | 462 | 60 | 14.1 |
| Ref. 1 | 4.1 | 8.5 | 6.5 | 0.158 | 0.220 | 470 | 72 | 5.9 |
| Ref. 2 | 4.4 | 9.4 | 6.7 | 0.155 | 0.211 | 470 | 70 | 6.3 |
| Ref. 3 | 4.0 | 8.0 | 6.3 | 0.156 | 0.212 | 469 | 71 | 5.5 |

As indicated in Table 2, when the ref 1 and ref. 2, which has a UV $\lambda_{max}$ shorter than 430 nm, are used as the fluorescent dopant in the EML as the Comparative Examples 1 to 3, the OLEDs exhibited low luminous efficiency owing to the low energy transfer efficiency from the emission wavelength of the delayed fluorescent material to the absorption wavelength of the fluorescent materials. Particularly, compared with using the benzofluoranthene-based or pyrene-based fluorescent material as a dopant in the Comparative Examples, when Compound 6, 7, 12 or 16 is used as the dopant in the EML, the driving voltage reduced by up to 13.6%, and the current efficiency, the power efficiency and $EQE_{max}$ were improved by up to 108.8%, up to 108.0% and up to 156.4%, respectively. In addition, compared with using the benzofluoranthene-based or pyrene-based fluorescent material as a dopant in the Comparative Examples, when Compound 6, 7, 12 or 16 is used as the dopant in the EML, it was confirmed that deep blue can be realized, and color purity is also improved owing to narrow FWHM.

From these results, it was confirmed that an organic light emitting diode and an organic light emitting device such as an organic light emitting display device and an organic light emitting illumination device using the organic compounds can enhance luminous efficiency and implement hyperfluorescence having high color purity.

While the present disclosure has been described with reference to exemplary embodiments and examples, these embodiments and examples are not intended to limit the scope of the present disclosure. Rather, it will be apparent to those skilled in the art that various modifications and variations can be made in the present disclosure without departing from the spirit or scope of the invention. Thus, it is intended that the present disclosure cover the modifications and variations of the present disclosure provided they come within the scope of the appended claims and their equivalents.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An organic compound represented by the following Chemical Formula 1:

Chemical Formula 1

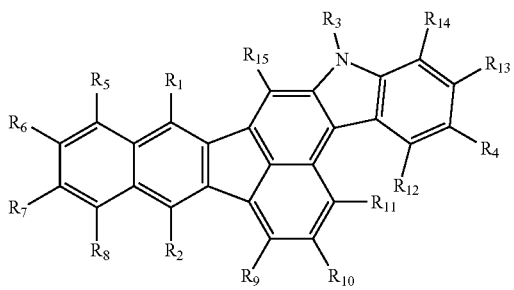

wherein each of $R_1$ to $R_3$ is independently $C_5$~$C_{30}$ aromatic group or $C_4$~$C_{30}$ hetero aromatic group, wherein each of the aromatic group and the hetero aromatic group is independently unsubstituted or substituted with linear or branched $C_1$~$C_{10}$ alkyl group or $C_1$~$C_{10}$ alkoxy group; $R_4$ is phenyl, naphthyl, anthracenyl or pyridyl, wherein each of the phenyl, naphthyl, anthracenyl and pyridyl is independently unsubstituted or substituted with at least one of linear or branched $C_1$~$C_{10}$ alkyl group and $C_5$~$C_{30}$ aryl group; each of $R_5$ to $R_{15}$ is independently hydrogen or $C_1$~$C_{10}$ alkyl group.

2. The organic compound of claim 1, wherein the organic compound comprises an organic compound having the following structure of Chemical Formula 2:

Chemical Formula 2

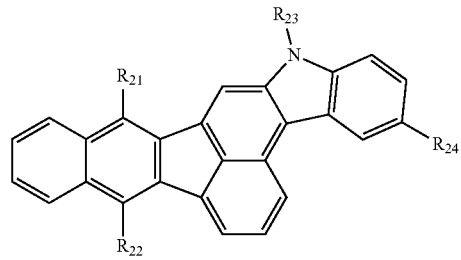

wherein each of $R_{21}$ to $R_{23}$ is independently $C_5$~$C_{30}$ aryl group unsubstituted or substituted with linear or branched $C_1$~$C_{10}$ alkyl group; $R_{24}$ is selected from the group consisting of phenyl, naphthyl, anthracenyl and pyridyl, wherein each of the phenyl, naphthyl, anthracenyl and pyridyl is independently unsubstituted or substituted with at least one of linear or branched $C_1$~$C_{10}$ alkyl group and $C_5$~$C_{30}$ aryl group.

3. The organic compound of claim 2, wherein $R_{24}$ is phenyl, naphthyl, anthracenyl or pyridyl, wherein each of phenyl, naphthyl, anthracenyl and pyridyl is independently unsubstituted or substituted with at least one of linear or branched $C_1$~$C_{10}$ alkyl group, phenyl and naphthyl.

4. The organic compound of claim 1, wherein the organic compound has any one having the following structure of Chemical Formula 3:

Chemical Formula 3

Compound 2

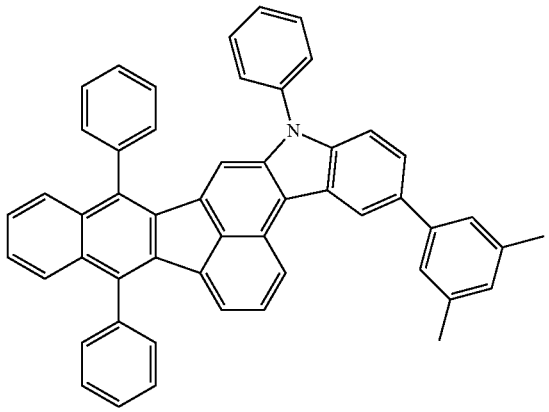

Compound 3

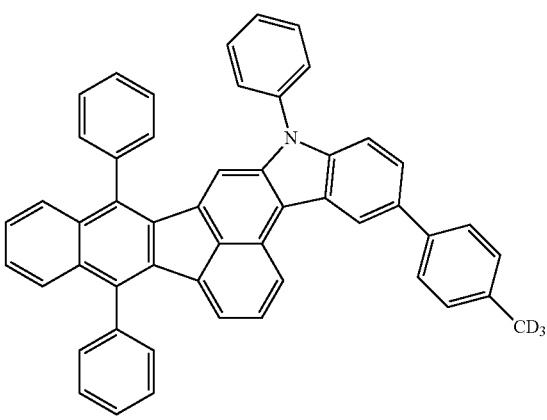

Compound 1

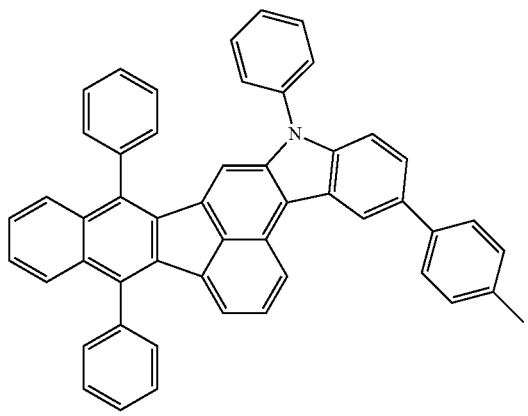

Compound 4

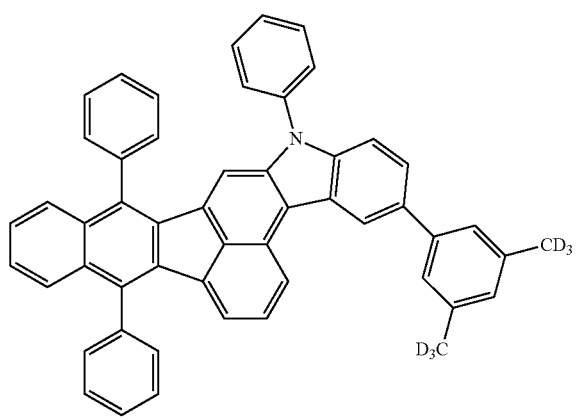

Compound 5
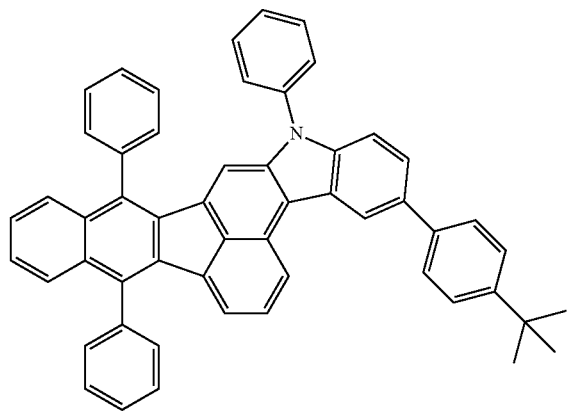
Compound 6
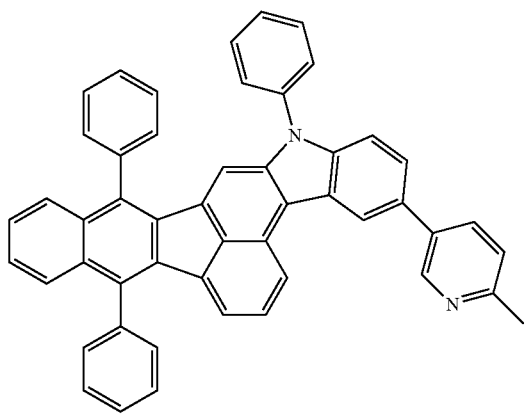
Compound 8
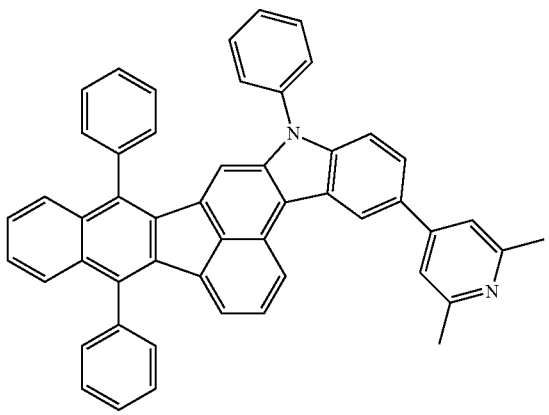
Compound 9
Compound 7
Compound 10
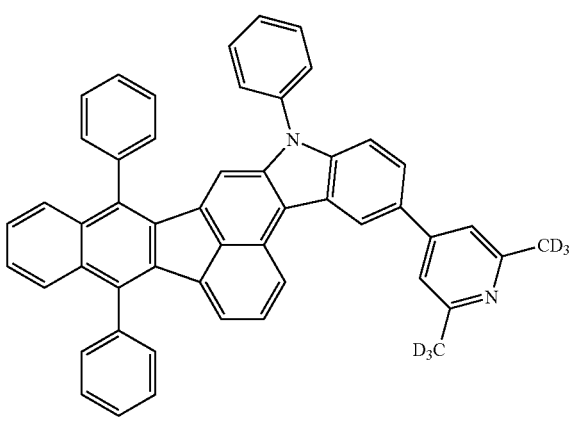

Compound 11
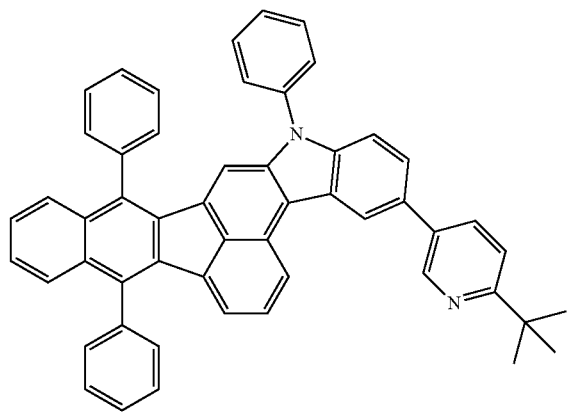
Compound 14
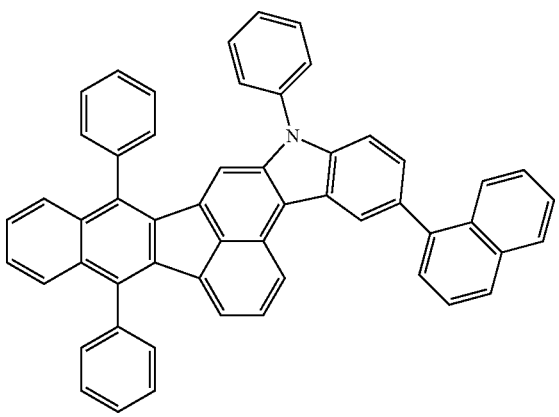
Compound 12
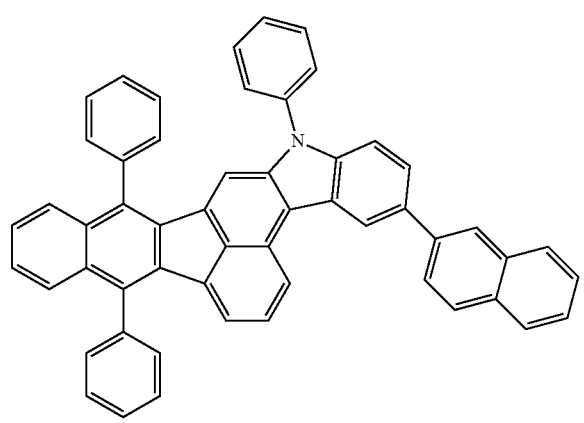
Compound 15
Compound 13
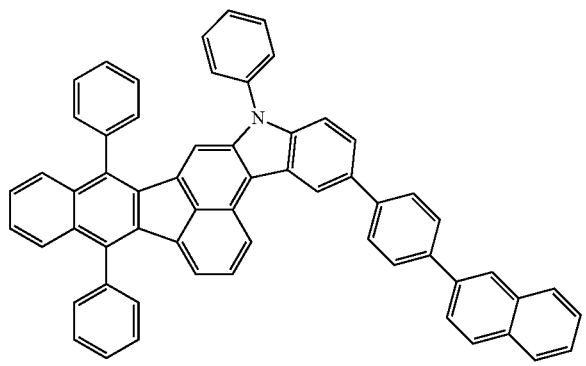
Compound 16

-continued

Compound 17

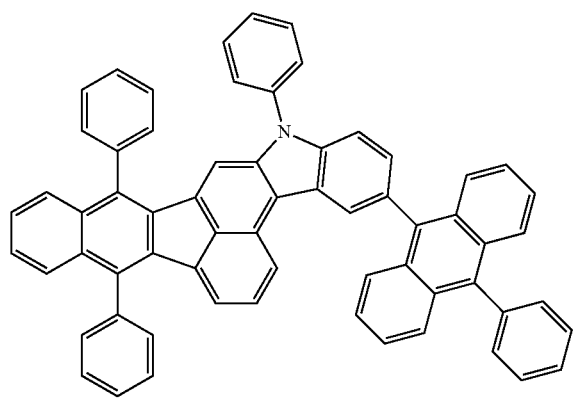

5. An organic light emitting diode comprising:
a first electrode and a second electrode, which face each other;
at least one emitting unit disposed between the first electrode and the second electrode and including a first emitting material layer,
wherein the first emitting material layer includes a first host and a first fluorescent dopant, and
wherein the first fluorescent dopant comprises an organic compound represented by the following Chemical Formula 1:

Chemical Formula 1

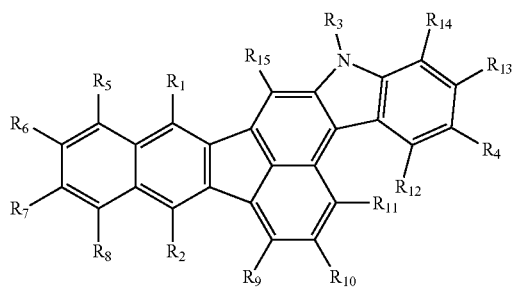

wherein, each of $R_1$ to $R_3$ is independently $C_5\text{~}C_{30}$ aromatic group or $C_4\text{~}C_{30}$ hetero aromatic group, wherein each of the aromatic group and the hetero aromatic group in $R_1$ to $R_3$ is independently unsubstituted or substituted with linear or branched $C_1\text{~}C_{10}$ alkyl group or $C_1\text{~}C_{10}$ alkoxy group, $R_4$ is phenyl, naphthyl, anthracenyl or pyridyl, wherein each of the phenyl, naphthyl, anthracenyl and pyridyl is independently unsubstituted or substituted with at least one of linear or branched $C_1\text{~}C_{10}$ alkyl group and $C_5\text{~}C_{30}$ aryl group; each of $R_5$ to $R_{15}$ is independently hydrogen or $C_1\text{~}C_{10}$ alkyl group.

6. The organic light emitting diode of claim 5, wherein the organic compound has any one having the following structure of Chemical Formula 3:

Chemical Formula 3

Compound 1

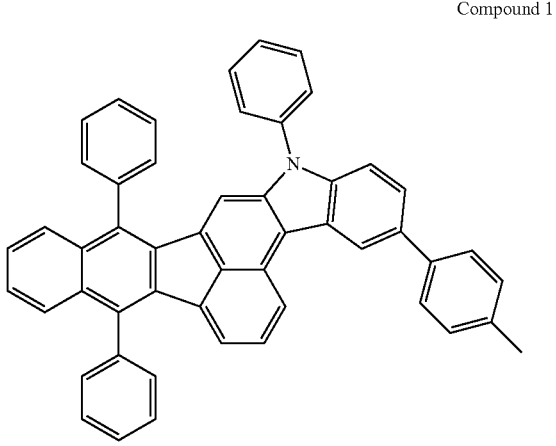

Compound 2

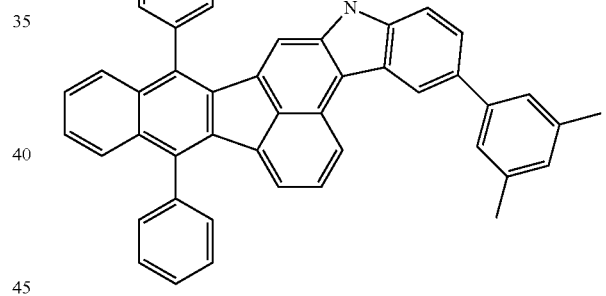

Compound 3

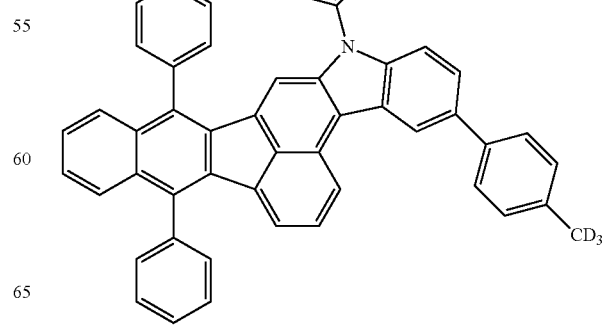

Compound 4
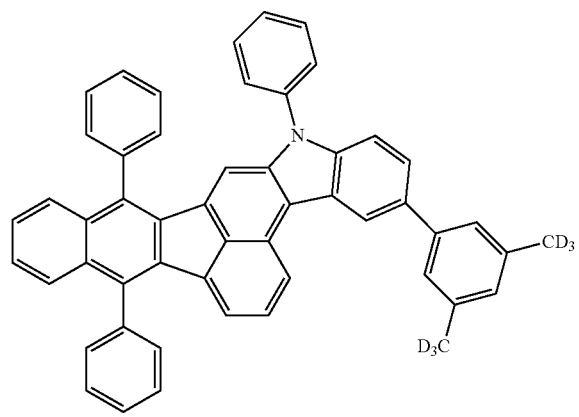
Compound 5
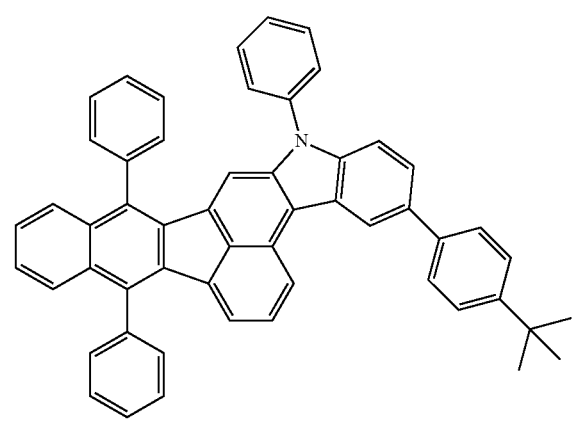
Compound 6
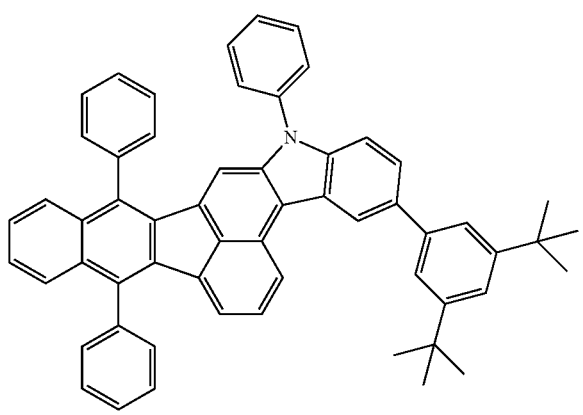
Compound 7
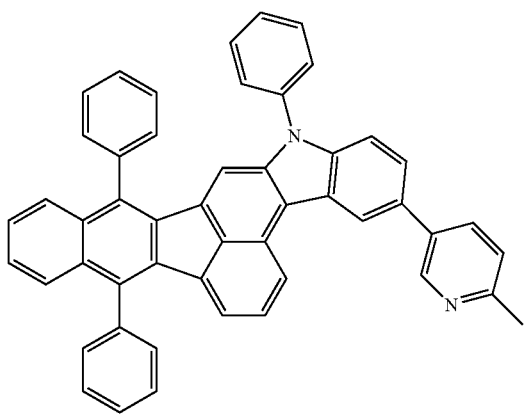
Compound 8
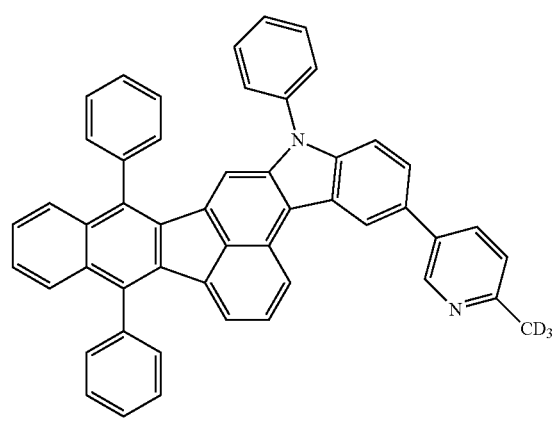
Compound 9

Compound 10
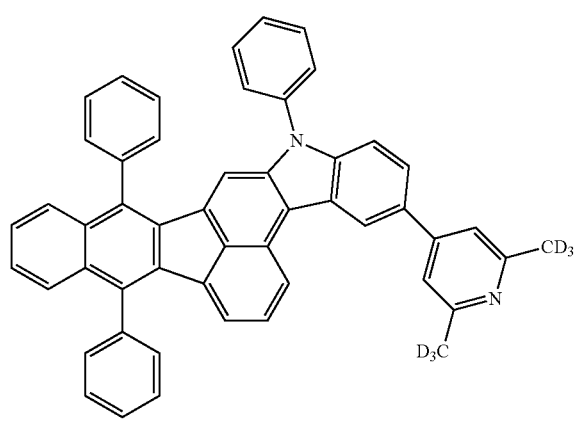
Compound 11
Compound 12
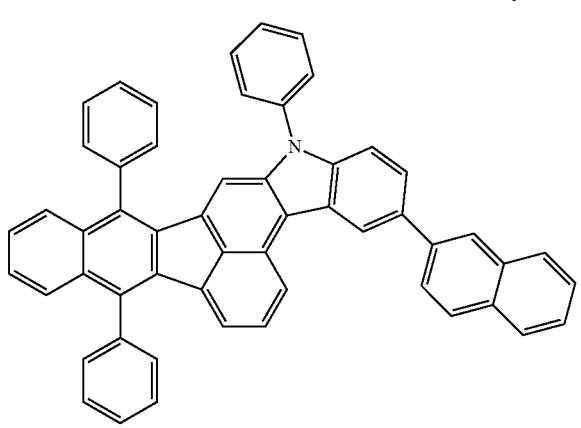
Compound 13
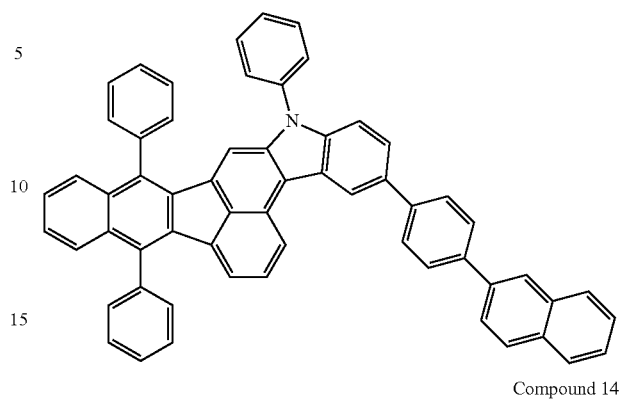
Compound 14
Compound 15
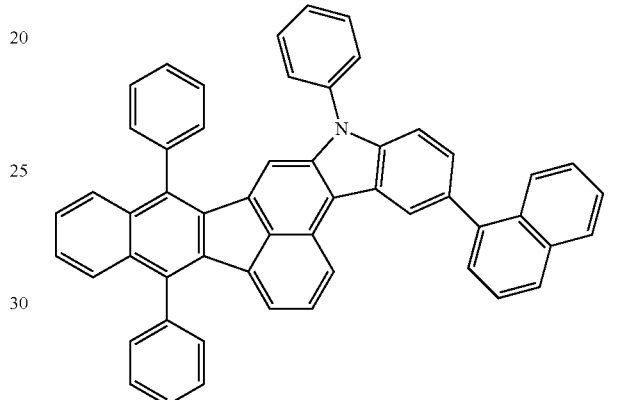
Compound 16
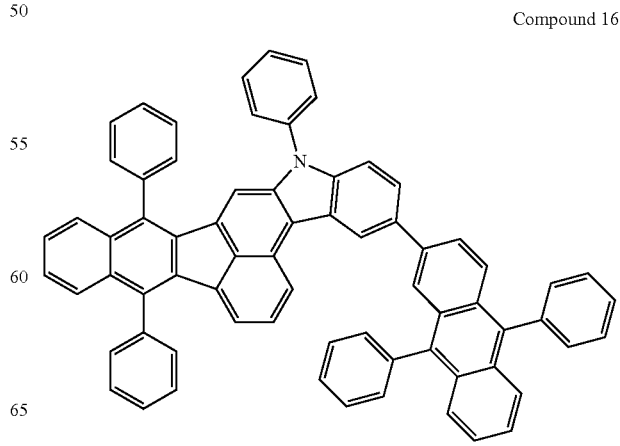

-continued

Compound 17

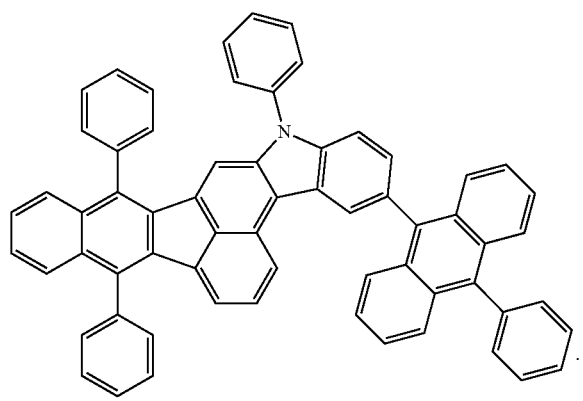

7. The organic light emitting diode of claim 5, wherein the first emitting material layer further comprise a delayed fluorescent dopant.

8. The organic light emitting diode of claim 7, wherein an excited state singlet energy level ($S_1^{TD}$) of the delayed fluorescent dopant is higher than an excited state singlet energy level ($S_1^{FD}$) of the first fluorescent dopant.

9. The organic light emitting diode of claim 7, wherein an energy level bandgap between an excited state singlet energy level ($S_1^{TD}$) and an excited state triplet energy level ($T_1^{TD}$) of the delayed fluorescent dopant is equal to or less than about 0.3 eV.

10. The organic light emitting diode of claim 7, wherein an excited state triplet energy level ($T_1^{TD}$) of the delayed fluorescent dopant is lower than an excited state triplet energy level ($T_1^H$) of the first host and higher than an excited state triplet energy level ($T_1^{FD}$) of the first fluorescent dopant.

11. The organic light emitting diode of claim 5, further comprising a second emitting material layer between the first electrode and the first emitting material layer or between the first emitting material layer and the second electrode, wherein the second emitting material layer comprises a second host and a delayed fluorescent dopant.

12. The organic light emitting diode of claim 11, wherein an excited state singlet energy level ($S_1^{TD}$) of the delayed fluorescent dopant is higher than an excited state singlet energy level ($S_1^{FD}$) of the first fluorescent dopant.

13. The organic light emitting diode of claim 11, wherein an excited state singlet energy level ($S_1^{H1}$) of the first host is higher than an excited state singlet energy level ($S_1^{FD}$) of the first fluorescent dopant, and each of an excited state singlet energy level ($S_1^{H2}$) and an excited state triplet energy level ($T_1^{H2}$) of the second host is respectively higher than an excited state singlet energy level ($S_1^{TD}$) and an excited state triplet energy level ($T_1^{TD}$) of the delayed fluorescent dopant.

14. The organic light emitting diode of claim 11, further comprising a third emitting material layer disposed oppositely to the first emitting material layer with respect to the second emitting material layer, wherein the third emitting material layer includes a third host and a second fluorescent dopant.

15. The organic light emitting diode of claim 14, wherein an excited state singlet energy level ($S_1^{TD}$) of the delayed fluorescent dopant is higher than an excited state singlet energy level ($S_1^{FD1}$) of the first fluorescent dopant and an excited state singlet energy level ($S_1^{FD2}$) of the second fluorescent dopant.

16. The organic light emitting diode of claim 14, wherein an excited state singlet energy level ($S_1^{H1}$) of the first host is higher than an excited state singlet energy level ($S_1^{FD1}$) of the first fluorescent dopant, each of an excited state singlet energy level ($S_1^{H2}$) and an excited state triplet energy level ($T_1^{H2}$) of the second host is respectively higher than an excited state singlet energy level ($S_1^{TD}$) and an excited state triplet energy level ($T_1^{TD}$) of the delayed fluorescent dopant, and an excited state singlet energy level ($S_1^{H3}$) of the third host is higher than an excited state singlet energy level ($S_1^{FD2}$) of the second fluorescent dopant.

17. The organic light emitting diode of claim 5, wherein the at least one emitting unit comprises a first emitting unit disposed between the first and second electrodes and a second emitting unit disposed between the first emitting unit and the second electrode, wherein at least one of the first and second emitting unit includes the first emitting material layer, and further comprising a charge generation layer disposed between the first and second emitting units.

18. The organic light emitting diode of claim 17, wherein one of the first and second emitting units further comprises a second emitting material layer disposed adjacently to the first emitting material layer.

19. The organic light emitting diode of claim 18, wherein one of the first and second emitting units further comprises a third emitting material layer disposed oppositely to the first emitting material layer with respect to the second emitting material layer.

20. An organic light emitting device, comprising:
a substrate; and
the organic light emitting diode according to claim 5 disposed on the substrate.

21. The organic light emitting device of claim 20, wherein the organic compound comprises an organic compound having the following structure of Chemical Formula 2:

Chemical Formula 2

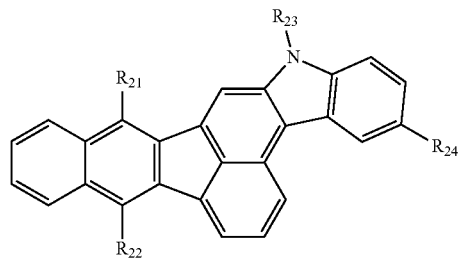

wherein each of $R_{21}$ to $R_{23}$ is independently $C_5$~$C_{30}$ aryl group unsubstituted or substituted with linear or branched $C_1$~$C_{10}$ alkyl group; $R_{24}$ is selected from the group consisting of phenyl, naphthyl, anthracenyl and pyridyl, wherein each of the phenyl, naphthyl, anthracenyl and pyridyl is independently unsubstituted or substituted with at least one of linear or branched $C_1$~$C_{10}$ alkyl group and $C_5$~$C_{30}$ aryl group.

22. The organic light emitting diode of claim 5, wherein the organic compound comprises an organic compound having the following structure of Chemical Formula 2:

Chemical Formula 2

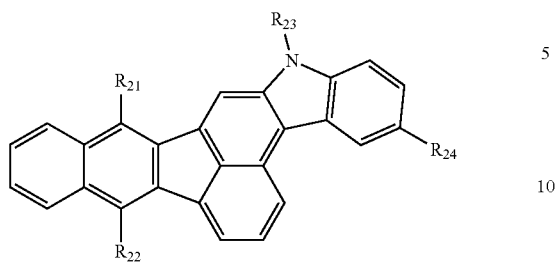

wherein each of $R_{21}$ to $R_{23}$ is independently $C_5$~$C_{30}$ aryl group unsubstituted or substituted with linear or branched $C_1$~$C_{10}$ alkyl group; $R_{24}$ is selected from the group consisting of phenyl, naphthyl, anthracenyl and pyridyl, wherein each of the phenyl, naphthyl, anthracenyl and pyridyl is independently unsubstituted or substituted with at least one of linear or branched $C_1$~$C_{10}$ alkyl group and $C_5$~$C_{30}$ aryl group.

* * * * *